US008258321B2

(12) United States Patent
Smith et al.

(10) Patent No.: US 8,258,321 B2
(45) Date of Patent: Sep. 4, 2012

(54) BETA-LACTONE COMPOUNDS

(75) Inventors: Jeffrey W. Smith, La Jolla, CA (US);
Daniel Romo, College Station, TX (US);
Gil Ma, College Station, TX (US);
Manuel Zancanella, College Station, TX (US)

(73) Assignees: Burnham Institute for Medical Research, La Jolla, CA (US); The Texas A&M University System, College Station, TX (US)

( * ) Notice: Subject to any disclaimer, the term of this patent is extended or adjusted under 35 U.S.C. 154(b) by 436 days.

(21) Appl. No.: 12/262,101

(22) Filed: Oct. 30, 2008

(65) Prior Publication Data

US 2009/0124681 A1    May 14, 2009

Related U.S. Application Data

(60) Provisional application No. 60/984,313, filed on Oct. 31, 2007.

(51) Int. Cl.
*C07D 305/12* (2006.01)
(52) U.S. Cl. ..................................................... 549/328
(58) Field of Classification Search .................... 549/328
See application file for complete search history.

(56) References Cited

U.S. PATENT DOCUMENTS

| 4,931,463 | A | * | 6/1990 | Barbier et al. | ................ | 514/422 |
| 5,175,186 | A | * | 12/1992 | Barbier et al. | ................ | 514/449 |
| 5,246,960 | A | * | 9/1993 | Barbier et al. | ................ | 514/422 |
| 6,566,553 | B2 |  | 5/2003 | Soucy et al. |  |  |
| 2003/0054020 | A1 |  | 3/2003 | Niazi |  |  |
| 2004/0024050 | A1 |  | 2/2004 | Smith et al. |  |  |

FOREIGN PATENT DOCUMENTS

| EP | 185359 | * | 6/1986 |
| EP | 0 444 482 A2 |  | 9/1991 |
| WO | WO 02/32850 A1 |  | 4/2002 |
| WO | WO 2004/065346 A1 |  | 8/2004 |

OTHER PUBLICATIONS

Biel et al. Chem.Eur.J. 2006, 12, 4121-4143.*
Pommier and Pons, "An Asymmetric Synthesis of (−)-Tetrahydrolipstatin," *Synthesis*, 1294-1300 (1994).
Barbier and Schneider, "Syntheses of Tetrahydrolipstatin and Absolute Configuration of Tetrahydrolipstatin and Lipstatin", *Helvetica Chimica Acta*, 70:196-202 (1987).
Barbier et al., "Stereoselective Syntheses of Tetrahydrolipstatin and of and Analogue, Potent Pancreatic-Lipase Inhibitors Containing a β-Lactone Moiety", *Helvetica Chimica Acta*, 70:1412-1418 (1987).

Bates et al., "The Use of π-Allyltricarbonyliron Lactone Complexes in the Synthesis of the β-Lactone Esterase Inhibitor (−)-Valilactone", *Tetrahedron*, 47(47):9929-9938 (1991).
Goese et al., "Biosynthesis of lipstatin. Incorporation of multiply deuterium-labeled (5Z,8Z)-tetradeca-5,8-dienoic acid and octanoic acid", *J. Org. Chem.*, 66(13):4673-8 (2001).
Hall and Dalbeth, "Obesity and cardiovascular risk factors in rheumatoid arthritis", *Rheumatology*, 45(6): 782-783 (2006).
Kocieński et al., "Asymmetric syntheses of panclicins A-E via [2+2] cycloaddition of alkyl(trimethylsilyl)ketenes to a β-silyloxyaldehyde", *J. Chem. Soc., Perkin Trans.*1, 8:1373-1382 (1998).
Kremer et al, "Identification and structural characterization of an unusual mycobacterial monomeromycolyl-diacylglycerol", *Mol. Microbial.*, 57(4):1113-26 (2005).
Lupu and Menendez, "Pharmacological inhibitors of Fatty Acid Synthase (FASN)—catalyzed endogenous fatty acid biogenesis: a new family of anti-cancer agents?", *Curr. Pharm. Biotechnol.*, 7(6):483-93 (2006).
Ma et al., "Total synthesis and comparative analysis of orlistat, valilactone, and a transposed orlistat derivative: Inhibitors of fatty acid synthase", *Org. Lett.*, 8(20):4497-500 (2006).
Ma et al., "Total synthesis and comparative analysis of orlistat, valilactone, and a transposed orlistat derivative: Inhibitors of fatty acid synthase", *Org. Lett.*, 8(20):S1-S31 (2006).
Mutoh et al., "Panclicins, novel pancreatic lipase inhibitors. I. Taxonomy, fermentation, isolation and biological activity", *J. Antibiot.* (Tokyo)., 47(12):1369-75 (1994).
Schuhr et al., "Biosynthetic precursors of the lipase inhibitor lipstatin", *J. Org. Chem.*, 67(7):2257-62 (2002).
Wedler et al., "Synthesis of Enantiomerically Pure β-Lactones by the Tandem Aldol-Lactonization. A Highly Efficient Access to (3S,4S)-3-Hexyl-4-[(2S)-2-hydroxytridecyl]oxetan-2-one, the Key Intermediate for the Enzyme Inhibitors Tetrahydrolipstatin and Tetrahydroesterastin", *J. Org. Chem.*, 64(14):5301-5303 (1999).
Wu and Sun, "An expeditious enantioselective total synthesis of valilactone", *J. Org. Chem.*, 71(15):5748-51 (2006).
European Search Report from EP 08 84 5661, Sep. 27, 2011.

* cited by examiner

*Primary Examiner* — Nizal Chandrakumar
(74) *Attorney, Agent, or Firm* — DLA Piper LLP (US)

(57) ABSTRACT

The present invention provides compounds having the general structure A, or a pharmaceutically acceptable derivatives thereof:

$$\begin{array}{c} O \\ \| \\ O-C \\ | \quad | \\ \underset{a}{CH}-\underset{b}{CH} \\ | \quad | \\ R_1 \quad R \end{array} \quad A$$

wherein R is an alkyl group, and $R_1$ comprises at least one moiety selected from a group consisting of an alkyl, an alkenyl, an aryl, a heterocycle, hydroxyl, ester, amido, aldehyde, and a halogen.

3 Claims, No Drawings

BETA-LACTONE COMPOUNDS

CROSS-REFERENCE TO RELATED APPLICATIONS

This application claims priority under 35 U.S.C. §119(e) to U.S. Patent Application Ser. No. 60/984,313 filed Oct. 31, 2007, the contents of which is herein incorporated by reference in its entirety.

GRANT INFORMATION

This invention was made in part with government support under NIH (Grant 5R01CA106582). The United States Government has certain rights in this invention.

BACKGROUND

1. Field of the Invention

The invention relates generally to compounds useful for the inhibition of certain thioesterases, and more specifically, to new compounds that include the β-lactone moiety or a β-lactam moiety that are useful as thioesterase inhibitors.

2. Background Information

The thioesterase superfamily contains a wide variety of enzymes, which exhibit esterase activity (i.e., splitting of an ester into acid and alcohol in the presence of water) specifically at a thiol group. This family includes, among others, 4HBT which catalyses the final step in the biosynthesis of 4-hydroxybenzoate from 4-chlorobenzoate in the soil dwelling microbe Pseudomonas CBS-3. The thioesterase superfamily also includes various cytosolic long-chain acyl-CoA thioester hydrolases. Long-chain acyl-CoA hydrolases hydrolyze palmitoyl-CoA to CoA and palmitate, as well as catalyse the hydrolysis of other long chain fatty acyl-CoA thioesters.

Human fatty acid synthase is a large homodimeric multifunctional enzyme that synthesizes palmitic acid. The unique carboxyl terminal thioesterase domain of fatty acid synthase hydrolyzes the growing fatty acid chain and plays a critical role in regulating the chain length of fatty acid released. Also, the up-regulation of human fatty acid synthase in a variety of cancer makes the thioesterase a candidate target for therapeutic treatment.

Recent studies have focused on the role of the thioesterase superfamily in various diseases, disorders and pathologies. While some compounds useful as inhibitors of various members of the thioesterase superfamily have been identified and synthesized, no compounds have been reported that are capable of targeting and inhibiting thioesterases such as human fatty acid synthase thioesterase.

SUMMARY

Currently, there is a need for novel, potent, and selective agents for the treatment of various diseases, disorders and pathologies, such as tumors, as well as for the pharmaceutical compositions including such agents. Such agents can be based on inhibitors of certain thioesterases, such as human fatty acid synthase thioesterase, ybtT (irp4) or HMWP-1 (irp1).

According to embodiments of the present invention, there are provided compounds having the general structure A:

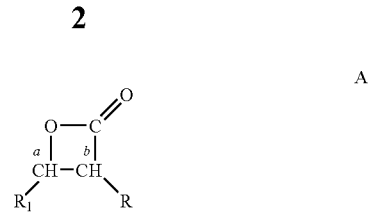

wherein R is an unsubstituted alkyl group or a substituted alkyl group, and $R_1$ comprises at least one moiety selected from the group consisting of an unsubstituted alkyl, a substituted alkyl, an unsubstituted alkenyl, a substituted alkenyl, an unsubstituted aryl, a substituted aryl, an unsubstituted heterocycle, a substituted heterocycle, hydroxyl, ester, amido, aldehyde, and a halogen. The stereochemical structure at carbons marked "a" and "b" can be either R or S.

According to other embodiments of the present invention, pharmaceutical compositions are provided for the treatment of various disorders, diseases, and pathologies, such as cancer, the compositions comprising a compound having the general structure A, and a pharmaceutically acceptable carrier therefor.

According to other embodiments of the present invention, methods for the treatment of various disorders, diseases, and pathologies, such as cancer, are provided, the methods comprising administering to a subject in need thereof a pharmacologically effective dose of a pharmaceutical composition comprising a compound having the general structure A.

DETAILED DESCRIPTION

The following definitions are used, unless otherwise described.

The term "lactone" refers a cyclic ester which is the condensation product of an alcohol group and a carboxylic acid group in the same molecule. The term beta-lactone (i.e., "β-lactone") is intended to indicate that the ring in the lactone is a four member ring.

The term "aldehyde" refers to an organic compound which incorporates a carbonyl functional group, $>C=O$, and where at least one of two remaining bonds is occupied by hydrogen.

The terms "alkyl" and "substituted alkyl" refer, respectively, to substituted and unsubstituted $C_1$-$C_{10}$ straight chain saturated aliphatic hydrocarbon groups, substituted and unsubstituted $C_2$-$C_{10}$ straight chain unsaturated aliphatic hydrocarbon groups, substituted and unsubstituted $C_4$-$C_{10}$ branched saturated aliphatic hydrocarbon groups, substituted and unsubstituted $C_4$-$C_{10}$ branched unsaturated aliphatic hydrocarbon groups, substituted and unsubstituted $C_3$-$C_8$ cyclic saturated aliphatic hydrocarbon groups, substituted and unsubstituted $C_5$-$C_8$ cyclic unsaturated aliphatic hydrocarbon groups having the specified number of carbon atoms.

The definition of "alkyl" includes, but is not limited to, any of the following: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like.

In substituted alkyls, substituents are independently selected from a group consisting of halogen, —OH, —SH, —$NH_2$, —CN, —$NO_2$, =O, =$CH_2$, trihalomethyl, carbamoyl, aryl$C_{0-10}$alkyl, heteroaryl$C_{0-10}$alkyl, $C_{1-10}$alkyloxy, aryl$C_{0-10}$alkyloxy, $C_{1-10}$alkylthio, aryl$C_{0-10}$alkylthio, $C_{1-10}$alkylamino, aryl$C_{0-10}$alkylamino, N-aryl-N—$C_{0-10}$alkylamino, $C_{1-10}$alkylcarbonyl, aryl$C_{0-10}$alkylcarbonyl, $C_{1-10}$alkylcarboxy, aryl$C_{0-10}$alkylcarboxy, $C_{1-10}$alkylcarbonylamino, aryl$C_{0-10}$alkylcarbonylamino, tetrahydrofuryl, morpholinyl, piperazinyl, hydroxypyronyl, —$C_{0-10}$alkylCOOR$_a$ and —$C_{0-10}$alkylCONR$_b$R$_c$, wherein R$_a$, R$_b$ and R$_c$ are independently selected from hydrogen, an alkyl, an aryl, or R$_b$ and R$_c$ are taken together with the nitrogen to which they are attached to form a saturated cyclic or unsaturated cyclic system containing 3 to 8 carbon atoms, with at least one substituent.

The term "aryl" refers to an unsubstituted, monosubstituted, disubstituted, or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). In substituted aruls, substituents are independently selected from the group consisting of halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_a$, and —$C_{0-10}$alkylCONR$_b$R$_c$, wherein R$_a$, R$_b$ and R$_c$ are independently selected from hydrogen, an alkyl, an aryl, or R$_b$ and R$_c$ are taken together with the nitrogen to which they are attached to form a saturated cyclic or unsaturated cyclic system containing 3 to 8 carbon atoms with at least one substituent.

The definition of "aryl" includes, but is not limited to, such specific groups as phenyl, biphenyl, naphthyl, dihydronaphthyl, tetrahydronaphthyl, indenyl, indanyl, azulenyl, anthryl, phenanthryl, fluorenyl, pyrenyl and the like.

The terms "heteroaryl", "heterocycle" or "heterocyclic" refer to a monovalent unsaturated group having a single ring or multiple condensed (also known as "fused") rings, from 1 to 8 carbon atoms and from 1 to 4 hetero atoms selected from nitrogen, sulfur or oxygen within the ring. The heteroaryl groups in this invention can be optionally substituted with 1 to 3 substituents selected from the group consisting of halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_a$, and —$C_{0-10}$alkylCONR$_b$R$_c$ wherein R$_a$, R$_b$ and R$_c$ are independently selected from hydrogen, an alkyl, an aryl, or R$_b$ and R$_c$ are taken together with the nitrogen to which they are attached to form a saturated cyclic or unsaturated cyclic system containing 3 to 8 carbon atoms with at least one substituent.

The definition of "heteroaryl" includes, but is not limited to, such specific groups as thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5]tetrazinanyl-3,6-dione, dihydro-pyrimidinyl-2,4-dione, pyrimidinyl-2,4,6-trione and the like.

The term "acyl" refers to a radical —R—C(=O)—, i.e., to a radical derived from an organic acid by the removal of the hydroxyl group of the carboxylic moiety. Typical examples of acyl groups include acetyl and benzoyl moieties.

The terms "halogen", "halide" or "halo" refer to fluorine, chlorine, bromine, and iodine.

The term "esterase" refers to any enzyme that catalyses the hydrolysis of organic esters, primarily carboxylates, but also phosphate and sulphate esters, to yield an alcohol or thiol, whatever the case may be, and acid. The term "thioesterase," which is a sub-genus of "esterase," refers to any enzyme which catalyzes the hydrolysis of thioesters, including, for example, the deacylating activity at the end of fatty acid biosynthesis leading to the release of palmitate.

The term "effective amount" of a compound refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount," yet, a suitable effective amount may be determined by one of ordinary skill in the art using commonly known techniques and methodologies.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

As used herein, the term "patient" refers to organisms to be treated by the methods of the present invention. Such organisms include, but are not limited to, humans. In the context of the invention, the term "subject" generally refers to an individual who will receive or who has received treatment for the treatment of a disease, disorder or pathology.

According to embodiments of the present invention, there are provided compounds comprising a β-lactone moiety, the compounds having the general structure A:

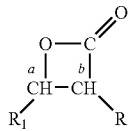

A

In the compound having the general structure A, the stereochemical structure at carbons marked "a" and "b" can be either R or S, as described below. Furthermore, in the compound having the general structure A, R is an unsubstituted alkyl group or a substituted alkyl group, such as ethyl, a propyl group, a butyl group, or a hexyl group.

Furthermore, in the compound having the general structure A, $R_1$ can be a moiety comprising a variety of functional groups, such as an unsubstituted alkyl, a substituted alkyl, an unsubstituted alkenyl, a substituted alkenyl, an unsubstituted aryl, a substituted aryl, an unsubstituted heterocycle, a substituted heterocycle, hydroxyl, ester, acyl, amido, aldehyde (including amino-substituted aldehyde such as formamide), halogen, and olefin fragments. Examples of some moieties that can represent the substitutent $R_1$ independently include any one of moieties 1-35, wherein the symbol * in moieties 1-35 signifies the point of attachment of the moiety to the carbon marked "a" the general structure A.

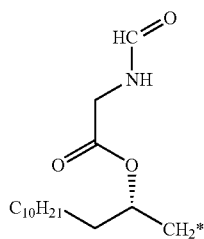

1

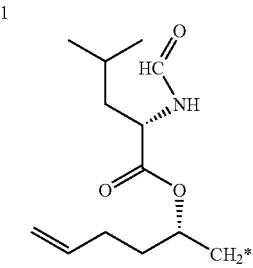

2

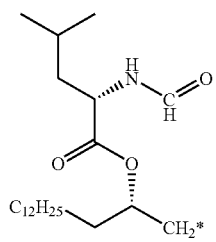

3

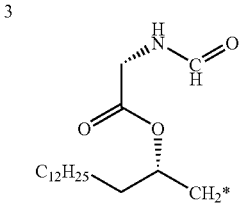

4

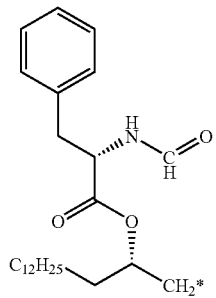

5

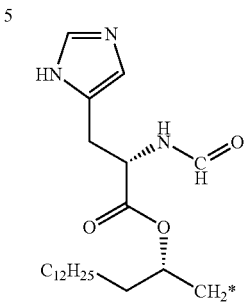

6

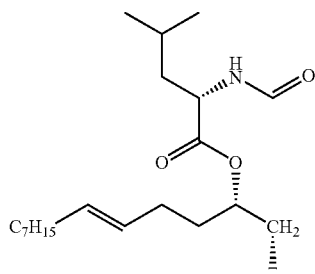

7

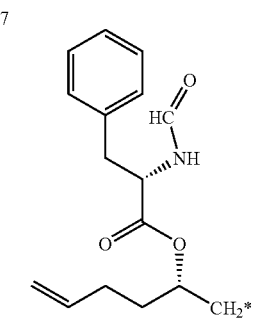

8

-continued
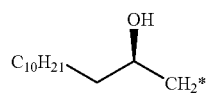
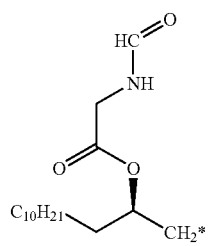
9
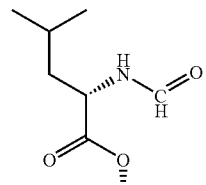
10
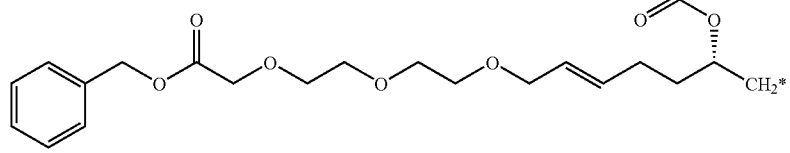
11
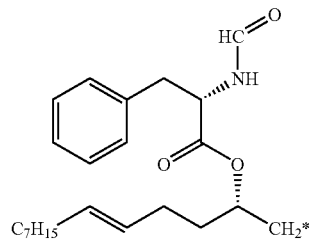
12
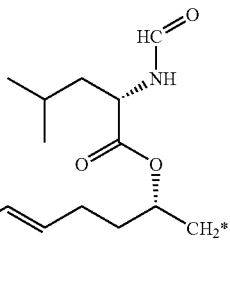
13
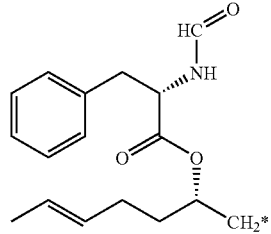
14
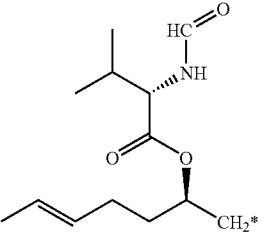
15
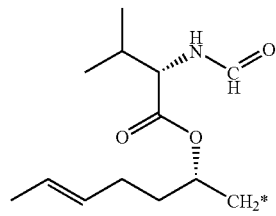
16
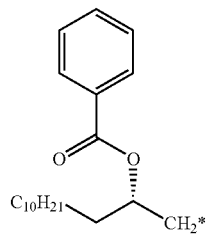
17
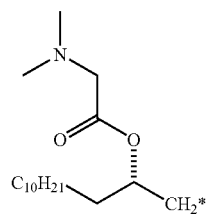
18
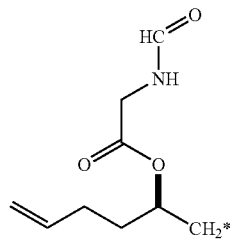
19

-continued
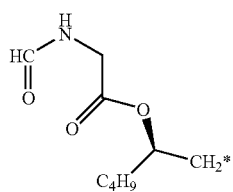
20
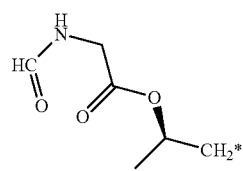
21
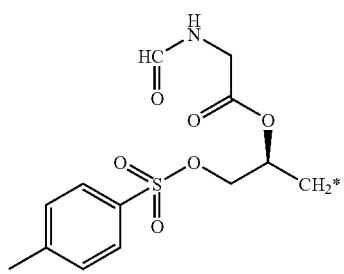
22
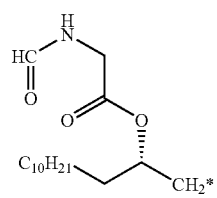
23
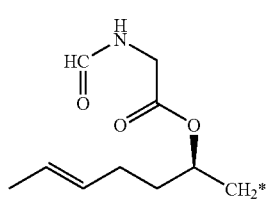
24
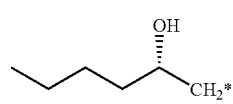
25
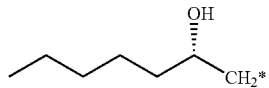
26
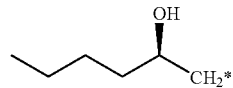
27
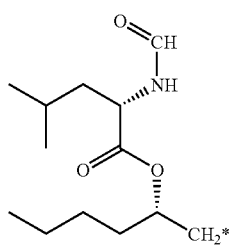
28
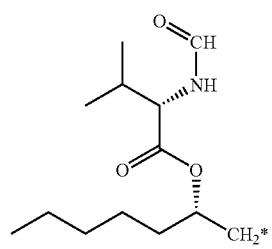
29
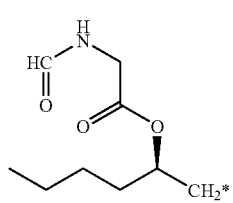
30
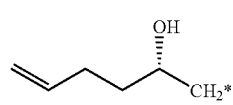
31
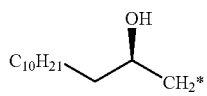
32
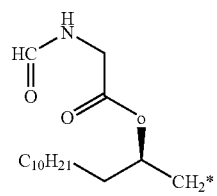
33

-continued
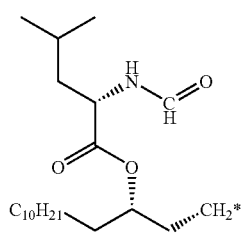
34
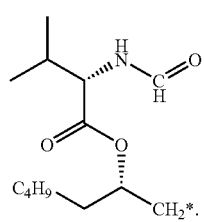
35
Examples of some specific compounds that are described by the general structure A and are within the purview of the present invention include the compounds I-XXX:
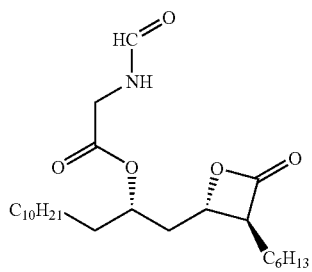
I
II
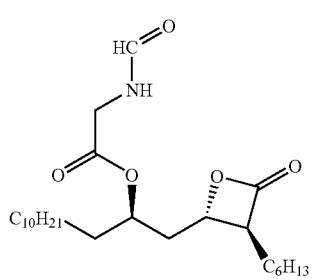
III
IV
V
VI
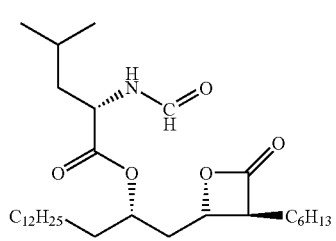
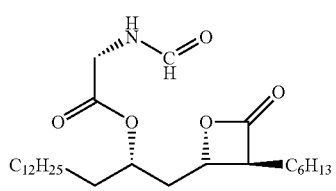
VII
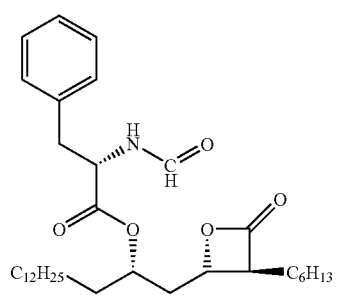
VIII -continued
IX
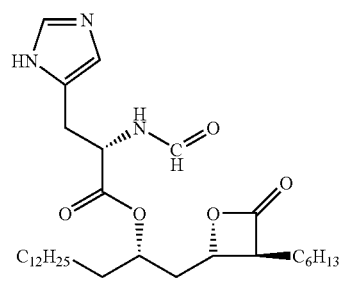
X
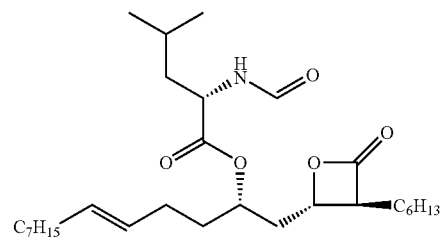
XI
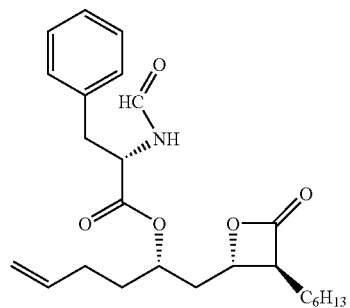
XII
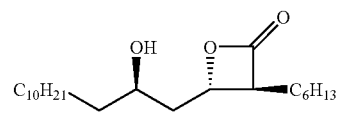
XIII
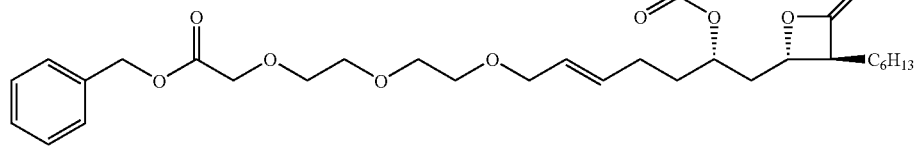
XIV
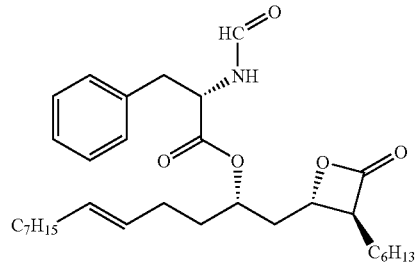
XV
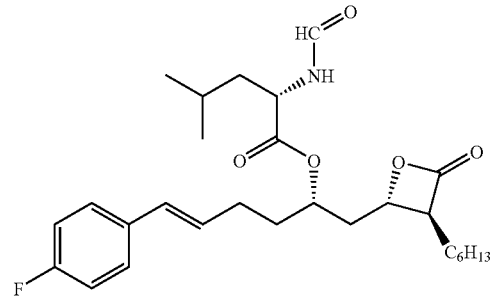
XVI
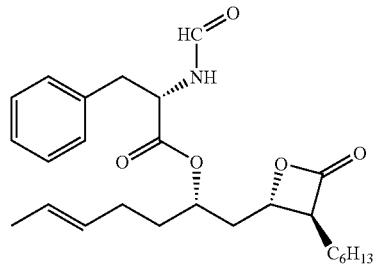
XVII
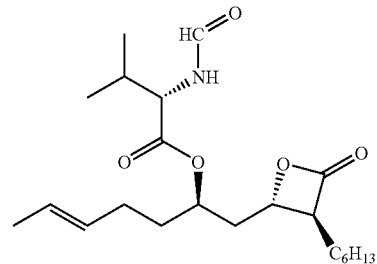

-continued
XVIII 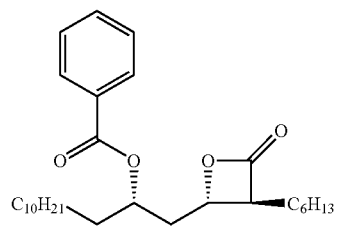
XIX 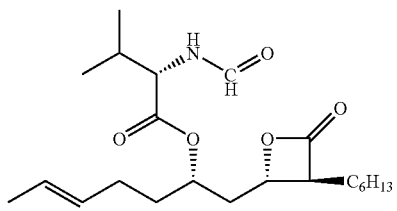
XX 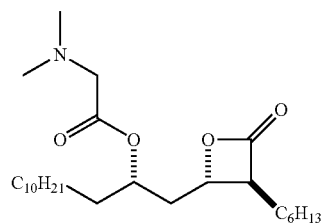
XXI 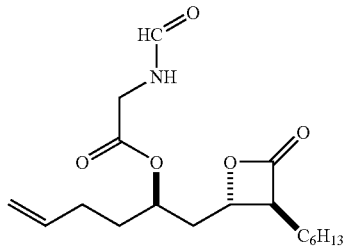
XXII 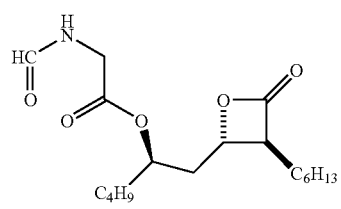
XXIII 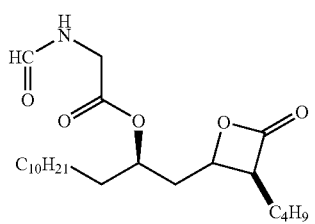
XXIV 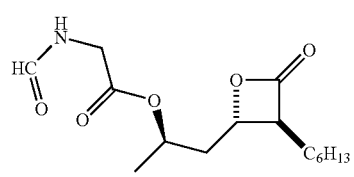
XXV 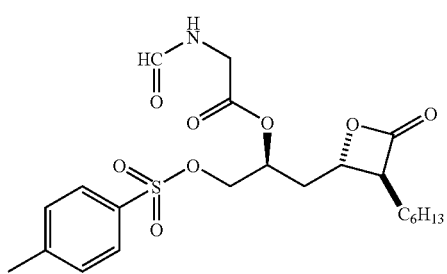
XXVI 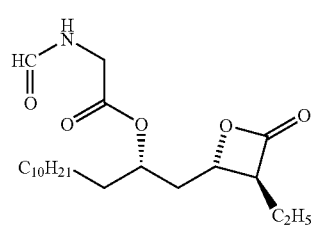
XXVII 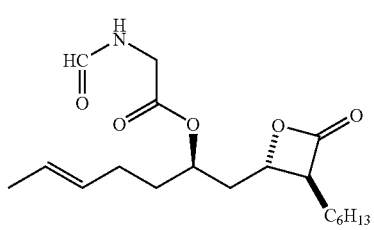
XXVIII 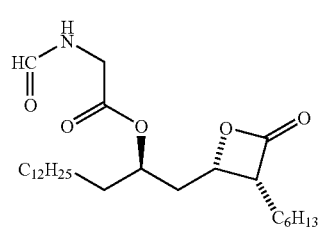
XXIX 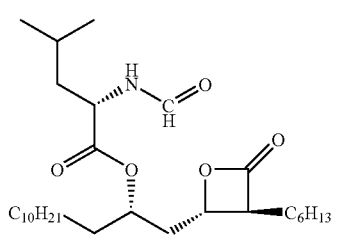

-continued

XXX

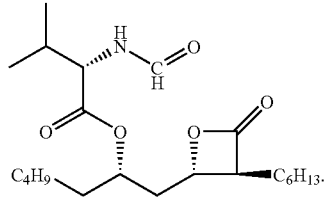

The compounds of the present invention are capable of inhibiting thioesterases, for example, human fatty acid synthase thioesterase, ybtT (irp4) or HMWP-1 (irp1), which can be utilized for the treatment of various disorders, diseases, and pathologies, such as cancer and other diseases discussed below. For example, it has been determined that certain microorganisms encode for thioesterases ybtT (irp4) and HMWP-1 (irp1). These microorganisms as well as their relation to various infections diseases and disorders are shown in Table 1.

TABLE 1

| Organism | Relates to Humans As | Note |
|---|---|---|
| E. coli CFT073 | Uropathogen | UTI infection |
| E. coli E110019 | Enteropathogen | |
| E. coli F11 | Uropathogen | Bladder infection (extra-intestinal) |
| Hahella chejuensis KCTC 2396 | None | Marine microbe |
| Photorhabdus asymbiotica subsp. asymbiotica | Pathogen | Pustulant sores on skin |
| Photorhabdus luminescens subsp. laumondii TTO1 | None | Insect pathogen |
| Pseudomonas aeruginosa 2192 | Pathogen | Opportunistic |
| Pseudomonas aeruginosa UCBPP-PA14 | Pathogen | Opportunistic, esp. burn victims |
| Pseudomonas syringae pv. phaseolicola 1448A | None | Plant pathogen |
| Pseudomonas syringae pv. tomato str. DC3000 | None | Plant pathogen |
| Yersinia enterocolitica 8081 | Pathogen | Most common human Yersinia infection |
| Yersinia pestis CO92 | Pathogen | Pneumonic plague |
| Yersinia pestis KIM | Pathogen | Responsible for $2^{nd}$ pandemic |
| Yersinia pestis biovar Medievalis str. 91001 | Pathogen | Highly similar to KIM (above) |
| Yersinia pseudotuberculosis | Pathogen | Lung lesions similar to tuberculosis |
| Yersinia pseudotuberculosis IP 32953 | Pathogen | Fully virulent form |

Accordingly, the compounds having the structure A, including the species I-XXX, or pharmaceutically acceptable salts thereof can be used for preparing pharmaceutical compositions, e.g., by combining these compounds and pharmaceutically acceptable carriers. The pharmaceutical compositions can then be used in pharmacologically effective doses for the treatment of various disorders, diseases, and pathologies.

Examples of the disorders, diseases, and pathologies that can be treated using the compounds of the present invention include, but are not limited to, hyperproliferative diseases such as cancer (including breast cancer, prostate cancer, ovarian cancer, colon cancer, non-small cell lung cancer, lung cancer, brain cancer, esophageal cancer, or liver cancer, and various types of leukemia), atherosclerosis, restenosis, inflammation, auto-immune diseases, diseases associated with angiogenesis including diabetic retinopathy, macular degeneration, arthritis, burns, and infectious diseases and disorders such as urinary tract infection, bladder infection, skin infections (e.g., pustulant skin sores), Yersinia infection, pneumonic plague, tuberculosis, and lung lesions similar to tuberculosis.

Various synthetic schemes can be designed for manufacturing the products having the structure A, including the species I-XXX. Some synthetic pathways that can be used are described in detail below, in the "Examples" portion of the application, where the starting and the final products are shown, together with conditions of the reactions and yields.

Briefly, the synthetic pathways that can be used include the synthesis of thiopyridyl ketene acetal, the synthesis of the chiral aldehyde, followed by Tandem Mukaiyama aldol-lactonization process and deprotection to deliver diastereoselective β-lactones. Amino ester side chains can be then introduced via Mitsunobu reaction or via acylation, δ-chains are extended via cross-metathesis and unsaturated Orlistat derivatives are hydrogenated to obtain the compounds that are the subject of the present invention.

Pharmaceutically acceptable salts of the compounds of the present invention may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The above-described compounds having the structure A, including the species I-XXX, can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds A, including the species I-XXX, can be determined by comparing their in vitro activity, and in vivo activity in animal models. Methods for the extrapolation of effective dosages in mice, and other animals, to humans are known to those having ordinary skill in the art.

Generally, the concentration of the compound(s) A, including the species I-XXX, in a liquid composition, such as a lotion, can be between about 0.1 and 25 mass %, such as between about 0.5 and 10 mass %. The concentration in a semi-solid or solid composition such as a gel or a powder can be between about 0.1 and 25 mass %, such as between about 0.5 and 2.5 mass %.

The amount of the compound(s) A, including the species I-XXX, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose can be in the range of between about 0.5 and 100 mg/kg, e.g., between about 10 and 75 mg/kg of body weight per day, such as between about 15 and 60 mg/kg/day. The compound(s) A, including the species I-XXX, can be conveniently administered in unit dosage form; for example, containing 5 to 1000 mg, such as 10 to 750 mg, for example, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The following examples further exemplify embodiments of the present invention, which are intended to further illustrate but not limit the invention.

EXAMPLE 1

General Synthetic Procedures

All reactions were carried out under nitrogen atmosphere in flame-dried glassware. Dichloromethane, acetonitrile, methanol, tetrahydrofuran, and ethyl ether were purified by passage through activated molecular sieves based (solvent system). Hünig's base and triethylamine were distilled from potassium hydroxide prior to use. All other commercially obtained reagents were used as received. $^1$H NMR chemical shifts are reported as δ values in ppm relative to $CDCl_3$ (7.27 ppm) and coupling constants (J) are reported in Hertz (Hz). Unless indicated otherwise, deuterochloroform ($CDCl_3$) served as an internal standard (77.23 ppm) for all $^{13}$C spectra. Flash column chromatography was performed using 60 Å

Silica Gel (Silicycle, 230-400 mesh) as a stationary phase. Mass spectra were obtained at the center for Chemical Characterization and Analysis (Texas A&M University). Thin layer chromatography (TLC) was performed using glass-backed silica gel $60_{F254}$ (Silicycle, 250 μm thickness). $^1$H and $^{13}$C NMR spectra were acquired using VARIAN spectrometers at the frequency indicated. Solvents are indicated for each compound. Chemical shifts are expressed in ppm referenced to the residual non-deuterated solvent, as an internal standard. $^1$H NMR coupling constants (J) are reported in Hertz (Hz) and multiplicities are abbreviated as follows: app=apparent, s=singlet, d=doublet, dd=doublet of doublets, t=triplet, q=quartet, m=multiplet, br=broad band signal. IR spectra were acquired using a Bruker Tensor 27 spectrometer in the solvent indicated. Vibration frequencies are expressed in $cm^{-1}$.

EXAMPLE 2

Synthesis of Thiopryridyl Ketene Acetal and of Chiral Aldehyde

The title products were synthesized as shown by the reaction scheme below. The yields for specific compounds are shown in Table 2, below.

TABLE 2

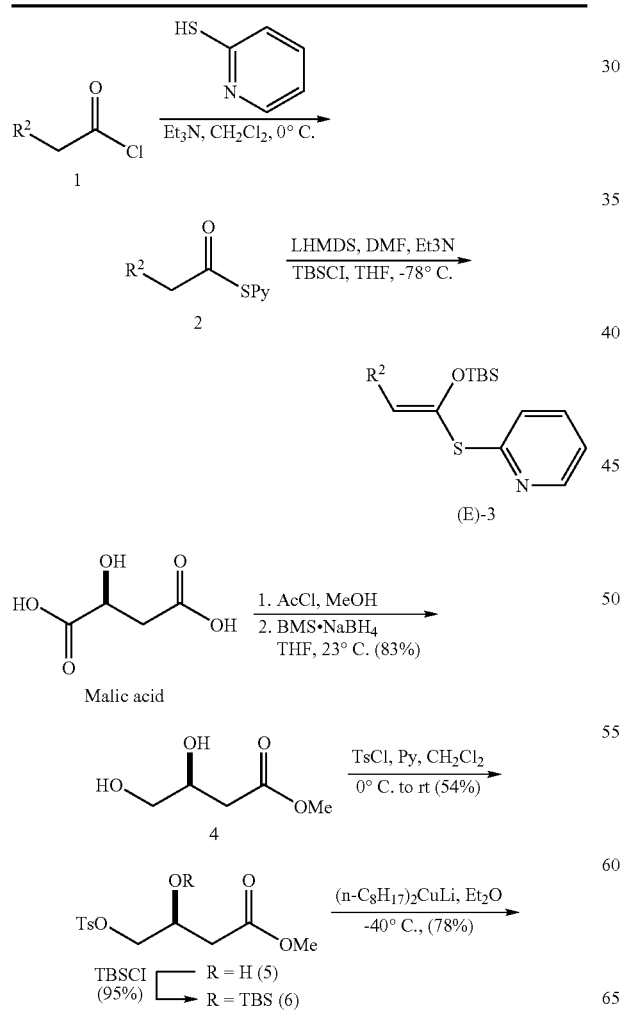

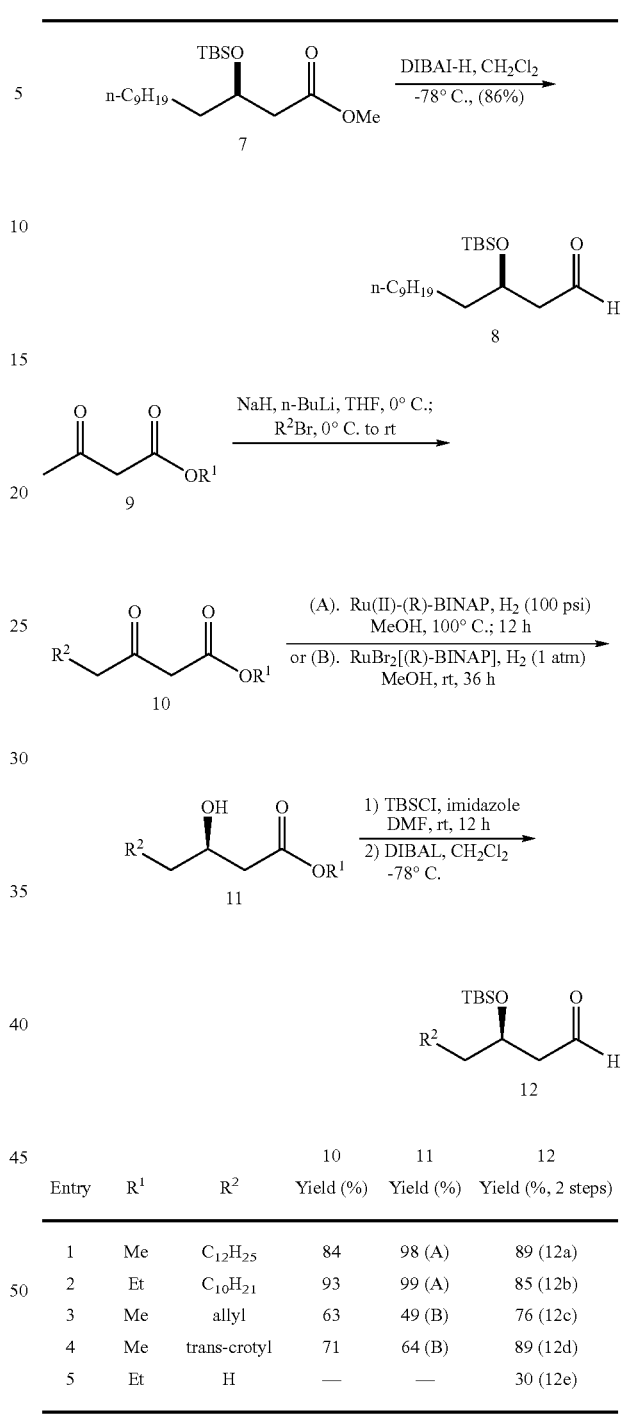

| Entry | $R^1$ | $R^2$ | 10 Yield (%) | 11 Yield (%) | 12 Yield (%, 2 steps) |
|---|---|---|---|---|---|
| 1 | Me | $C_{12}H_{25}$ | 84 | 98 (A) | 89 (12a) |
| 2 | Et | $C_{10}H_{21}$ | 93 | 99 (A) | 85 (12b) |
| 3 | Me | allyl | 63 | 49 (B) | 76 (12c) |
| 4 | Me | trans-crotyl | 71 | 64 (B) | 89 (12d) |
| 5 | Et | H | — | — | 30 (12e) |

EXAMPLE 3

Tandem Mukaiyama Aldol-Lactonization Process and Deprotection

The title process was carried out as shown by the reaction scheme below. Diastereoselective β-lactones were obtained as a result. The yields for specific compounds, and ratios are shown in Table 3, below.

TABLE 3

| Entry | $R_1$ | $R_2$ | Product (major, 13) | Ratio (13:14)[a] | Yield (%)[b] |
|---|---|---|---|---|---|
| 1 | $C_{12}H_{25}$ (12a) | $C_6H_{13}$ | | 13a:14a = 6:1 | 58 |
| 2 | $C_{12}H_{25}$ | $C_2H_5$ | | 13b:14b = 6:3:1 | 61 |
| 3 | $C_{12}H_{25}$ | $O(CH_2)_2OCH_3$ E/Z | | 13c:14c = 19:1 | 20 |
| 4 | $C_{10}H_{21}$ (12b) | $C_6H_{13}$ | | 13d:14d = 8:1 | 58 |
| 5 | $C_{10}H_{21}$ | $C_4H_9$ | | 13e:14e = 7.7:1 | 49 |
| 6 | $C_{10}H_{21}$ | $C_2H_5$ | | 13f:14f = 6:1 | 58 |
| 7 | $C_{10}H_{21}$ | Me E/Z | | 13g:14g = variable | 20 |
| 8 | $C_{10}H_{21}$ | $O(CH_2)_2OCH_3$ E/Z | | 13h:14h = 7:1 | 15 |

TABLE 3-continued

| Entry | R₁ | R₂ | Product (major, 13) | Ratio (13:14)$^a$ | Yield (%)$^b$ |
|---|---|---|---|---|---|
| 9 | C₈H₁₇ (12f) | C₈H₁₇ | | 13i:14i = 8.4:1 | 42 |
| 10 | Allyl (12c) | C₆H₁₃ | | 13j:14j = ND | 60 |
| 11 | trans-crotyl (12d) | C₆H₁₃ | | 13k:14k = 9:1 | 62 |
| 12 | H (12e) | C₆H₁₃ | | 13l:14l = 7.1:1 | 42 |
| 13 | (CH₂=CH)C₈H₁₆ (12g) | C₆H₁₃ E/Z | | 13m:14m = 1:1 | 50 |
| 14 | OTs (12h) | C₆H₁₃ | | 13n:14n = 7.7:1 | ND |
| 15 | H | C₄H₉ | | 13o:14o = 7.7:1 | ND |

EXAMPLE 4
Introduction of Amino Ester Side Chain Via Mitsunobu Reaction
The title process was carried out as shown by the reaction scheme below. The yields for specific compounds are shown in Table 4, below.
TABLE 4
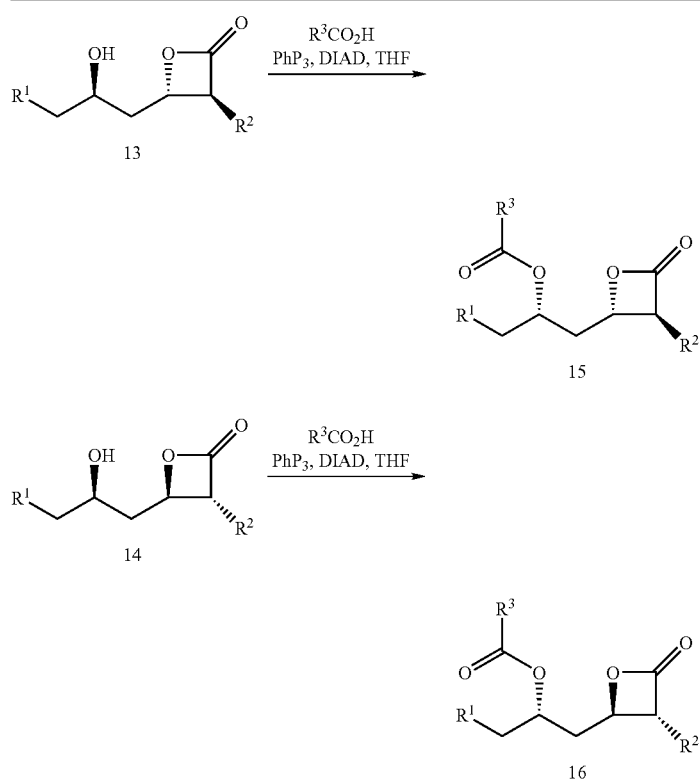
| Entry | Comp. # | Product | Yield |
|---|---|---|---|
| 1 | 15a | (structure with NHCHO, H25C12, C2H5) | ND |
| 2 | 15b | (structure with NHCHO, H25C12, C6H13) | 80 |
| 3 | 15c | (structure with NHCHO, H25C12, C6H13) | 73 |

TABLE 4-continued

| | | | |
|---|---|---|---|
| 4 | 15d | Phe-NHCHO ester, H25C12 chain, C6H13 β-lactone | 80 |
| 5 | 15e | His-NHCHO ester, H25C12 chain, C6H13 β-lactone | 17 |
| 6 | 15f | Leu-NHCHO ester, H25C12 chain, OCH2CH2OMe β-lactone | 67 |
| 7 | 15g | Leu-NHCHO ester, H21C10 chain, methyl β-lactone | ND |
| 8 | 15h | Leu-NHCHO ester, H21C10 chain, C2H5 β-lactone | 25 |
| 9 | 15i | Gly-NHCHO ester, H21C10 chain, C2H5 β-lactone | 43 |
| 10 | 15j | benzoate ester, H21C10 chain, C6H13 β-lactone | ND |
| 11 | 15k | N,N-dimethylglycine ester, H21C10 chain, C6H13 β-lactone | 73 |

TABLE 4-continued

| # | ID | Structure | Yield |
|---|---|---|---|
| 12 | 15l | [Orlistat structure: leucine-NHCHO ester on β-lactone with C₁₀H₂₁ and C₆H₁₃ chains] Orlistat | 80 |
| 13 | 15m | [glycine-NHCHO ester on β-lactone with C₁₀H₂₁ and C₆H₁₃ chains] | 87 |
| 14 | 15n | [valine-NHCHO ester on β-lactone with pentenyl and C₆H₁₃ chains] | 45 |
| 15 | 15o | [phenylalanine-NHCHO ester on β-lactone with pentenyl and C₆H₁₃ chains] | ND |
| 16 | 15p | [leucine-NHCHO ester on β-lactone with butenyl and C₆H₁₃ chains] | 68 |
| 17 | 15q | [phenylalanine-NHCHO ester on β-lactone with butenyl and C₆H₁₃ chains] | 46 |
| 18 | 15r | [leucine-NHCHO ester on β-lactone with C₈H₁₇ and C₈H₁₇ chains] | 74 |

TABLE 4-continued

| | | | |
|---|---|---|---|
| 19 | 16a | (structure: leucine NHCHO ester on β-lactone with $H_{25}C_{12}$ and $C_6H_{13}$) | 17 |
| 20 | 16b | (structure: leucine NHCHO ester on β-lactone with $H_{21}C_{10}$ and methyl) | ND |

EXAMPLE 5

Introduction of Amino Ester Side Chain Via Acylation

The title process was carried out as shown by the reaction scheme below. The yields for specific compounds are shown in Table 5, below.

TABLE 5

Reaction scheme: Compound 13 (with $R^1$, OH, $R^2$ on β-lactone) → Compound 17 (with $R^3$CO-O group) using $R_3CO_2H$, EDCl, DMAP, $CH_2Cl_2$.

| Entry | Compound # | Product | Yield (%) |
|---|---|---|---|
| 1 | 17a | (NHCHO-CH$_2$-C(O)O- on β-lactone with $H_{21}C_{10}$ and $C_2H_5$) | 99 |
| 2 | 17b | (NHCHO-CH$_2$-C(O)O- on β-lactone with $H_{21}C_{10}$ and $C_4H_9$) | 69 |
| 3 | 17c | (NHCHO-CH$_2$-C(O)O- on β-lactone with $H_{21}C_{10}$ and $C_6H_{13}$) | 97 |
| 4 | 17d | (NHCHO-CH$_2$-C(O)O- on β-lactone with methyl and $C_6H_{13}$) | 52 |
| 5 | 17e | (NHCHO-CH$_2$-C(O)O- on β-lactone with TsO-CH$_2$- and $C_6H_{13}$) | 58 |
| 6 | 17f | (NHCHO-CH$_2$-C(O)O- on β-lactone with allyl chain and $C_6H_{13}$) | 55 |

TABLE 5-continued
| | | | |
|---|---|---|---|
| 7 | 17g | 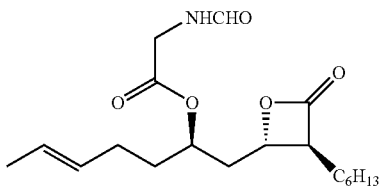 | 57 |
| 8 | 17h | 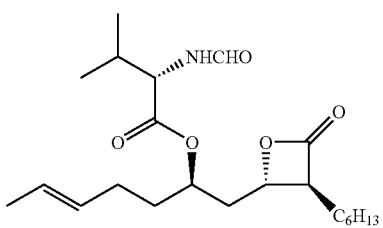 | ND |
| 9 | 17i | 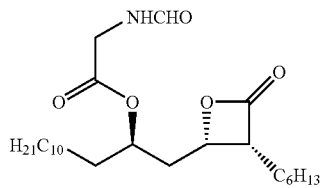 | 51 |
EXAMPLE 6
δ-Chain Extension Via Cross-Metathesis
The title process was carried out as shown by the reaction scheme below. The yields for specific compounds are shown in Table 6, below.
TABLE 6
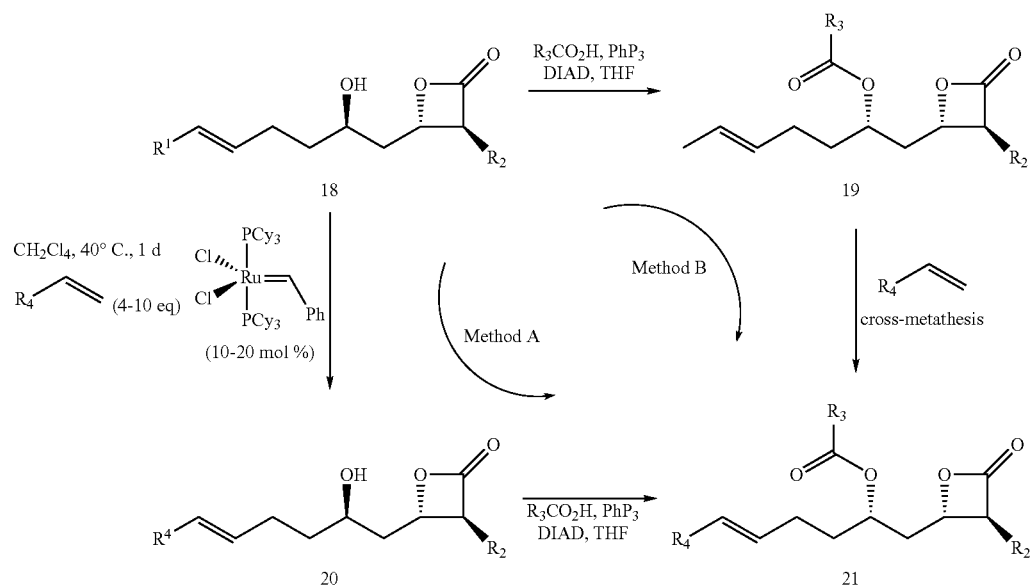
| Entry | Compound # | Product | Yield (%) |
|---|---|---|---|
| 1 | 21a | 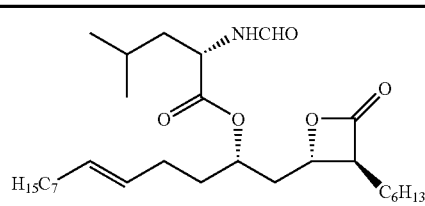 | ND |
| 2 | 21b | 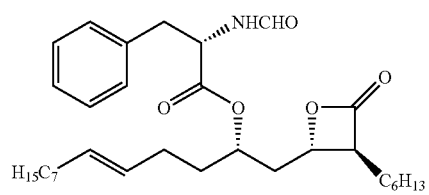 | 38 |

TABLE 6-continued
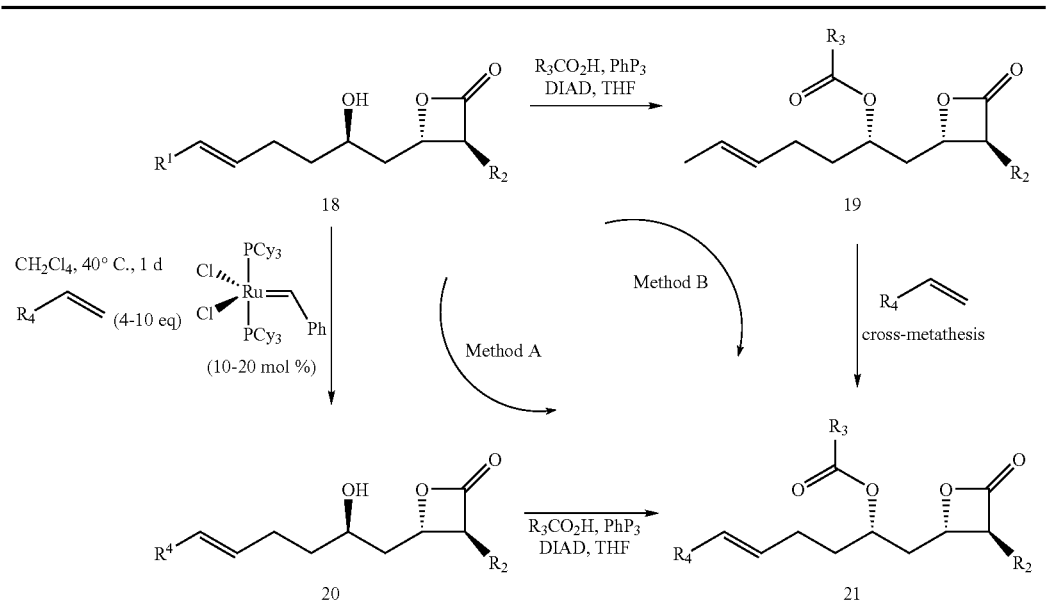
| Entry | Compound # | Product | Yield (%) |
|---|---|---|---|
| 3 | 21c | | ND |
| 4 | 21d | | ND |
| 5 | 21f | | ND |

EXAMPLE 7

Hydrogenation of Unsaturated Orlistat Derivatives

The title process was carried out as shown by the reaction scheme below. The yields for specific compounds are shown in Table 7, below.

TABLE 7

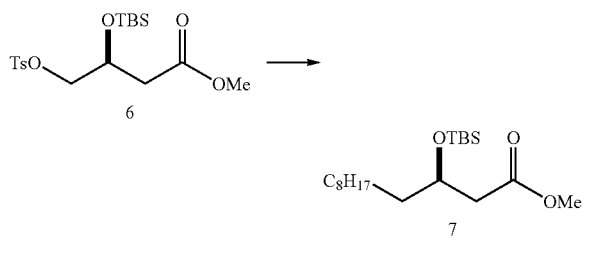

| Entry | Compound # | Product | Yield (%) |
|---|---|---|---|
| 1 | 23a | (structure with NHCHO, isopropyl, C$_6$H$_{13}$) | 95 |
| 2 | 23b | (structure with NHCHO, C$_6$H$_{13}$) | 95 |

EXAMPLE 8

Synthesis of (R)-methyl 3-(tert-butyldimethylsilyloxy)dodecanoate (7)

The title compound was synthesized by the cuprate alkylation as shown by the reaction scheme below.

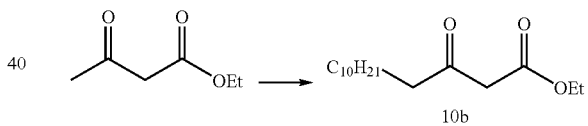

To a stirred solution of 1-iodooctane (5.5 mL, 30 mmol) in 56 mL of dry Et$_2$O cooled to −78° C., t-BuLi (35 mL, 59 mmol) was added slowly via a syringe. 5 more mL of Et$_2$O were added and the solution was stirred for 1 h at −78° C., then allowed to reach room temperature and stirred for 1 h. The solution was then re-cooled to −35° C. and transferred via a cannula to a cooled (−35° C.) suspension of CuI (2.84 g, 14.9 mmol) in 74 mL of Et$_2$O, resulting in an increasingly darker mixture. After complete addition, the dark solution was stirred at about −35° C./−45° C. for 2 h, and then a solution of tosylate 6 (1.006 g, 2.500 mmol) in 50 mL of Et$_2$O was added slowly via a syringe.

The resulting mixture was stirred at −35° C./−45° C. for 2.5 h, after which 90 mL of a saturated NH$_4$Cl solution were added. The mixture was allowed to reach room temperature, and then extracted three times with EtOAc. The combined organic layers were washed twice with saturated NaHCO$_3$ solution and twice with brine, dried over Na$_2$SO$_4$, filtered and concentrated in vacuo. Purification of the residue via silica gel chromatography (95:5 pentane/Et$_2$O) yielded the title ester 7 (671 mg, 78%) as a slightly yellow oil.

$^1$H NMR (300 MHz, CDCl$_3$) δ 4.13 (tt, J=5.7, 5.7 Hz, 1H), δ 3.67 (s, 3H), 2.44 (m, 2H), 1.42-1.53 (m, 2H), 1.27 (br. s., 14H), 0.89 (t, 3H), 0.87 (s, 9H), 0.06 (s, 3H), 0.04 (s, 3H).

EXAMPLE 9

Synthesis of (R)-3-(tert-Butyl-dimethyl-silanyloxy)-tetradecanal (12b) (Representative Procedure)

The title compound was synthesized by the sequence of synthetic steps as shown by the reaction schemes below.

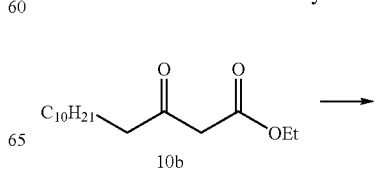

To a solution of NaH (60% in mineral oil, 3.8 g, 95 mol) in 150 mL of THF at 0° C. was added ethyl acetoacetate (9.3 mL, 86 mol) dropwise and the resulting solution was stirred at 0° C. for 10 min. To this solution was added dropwise n-BuLi (2.5 M in hexane, 38 mL, 95 mmol) and the yellow solution was stirred at 0° C. for an additional 10 min. To a solution of dianion was added a solution of iododecane (18.4 mL, 86 mmol) dropwise at 0° C. This reaction mixture was allowed to slowly warm to ambient temperature over 2 h and quenched with 1 N HCl. The aqueous layer was further extracted with ethyl ether (×3). The organic extracts were combined, washed with water until neutral, dried over Na$_2$SO$_4$ and filtered. The crude oil was purified by flash chromatography (95:5 hexanes:EtOAc) to afford the desired product 10b (21.6 g, 93%) as a colorless oil. The next synthetic step was as follows:

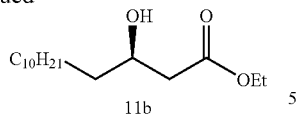

The solution of β-ketoester 10b (13.0 g, 50.7 mmol) in 30 mL of MeOH was degassed and [Ru(II)-R—BIBAP], which was prepared from RuCl$_2$(benzene)$_2$ (54 mg) and R—BINAP (75 mg), was added. An autoclave was charged with the above solution and reaction mixture was stirred under H$_2$ (100 psi) at 100° C. for 12 h. The cooled reaction mixture was concentrated under reduced pressure and the residue was purified by flash chromatography (9:1 hexanes:EtOAc) to afford the desired product 11b (13.8 g, 99%) as a white solid. The next synthetic step was as follows:

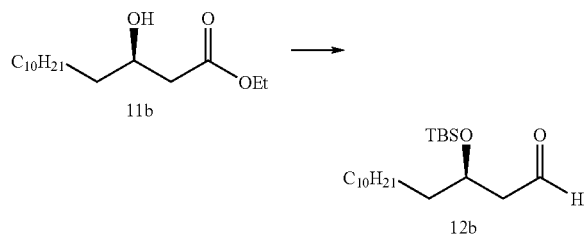

To a solution of 11b (8.00 g, 31.0 mmol) and imidazole (3.59 g, 52.7 mmol) in 35 mL of DMF was added TBSCl (6.07 g, 40.2 mmol). The mixture was stirred overnight at ambient temperature and diluted with 150 mL of ethyl ether. The organic layer was washed with brine, dried over Na$_2$SO$_4$, filtered, and concentrated. The residue was purified by chromatography on SiO$_2$ (20:1 hexane/EtOAc) to give the desired product (10.1 g, 85%) as a colorless oil.

To a stirred solution of ester (3.00 g, 7.76 mmol) in 60 ml of CH$_2$Cl$_2$ cooled to −78° C., DIBAL-H (2.87 mL, 16.1 mmol) in 10 mL of CH$_2$Cl$_2$ was added drop-wise and the mixture was stirred at −78° C. for 2 h. The reaction was then quenched by the addition of 10 mL of MeOH and the mixture was allowed to reach room temperature while stirring. 15 mL of Rochelle's salt solution were added, and the mixture was stirred vigorously for 3 h. The aqueous phase was then separated and extracted with CH$_2$Cl$_2$ (×2). The combined organic layers were dried over Na$_2$SO$_4$, filtered and concentrated in vacuo. The residue was purified by chromatography on SiO$_2$ (20:1 hexane:EtOAc) to give 12b (2.80 g, 100%) as a colorless oil. (Reference for spectral data: Pommier, A.; Pons, J.-M. *Synthesis*, 1994, 1294-1300.)

Another similar product, (S)-3-(tert-butyl-dimethyl-silanyloxy)-oct-6-enal (12d), the formula of which is shown below was also obtained using the above-described representative procedure.

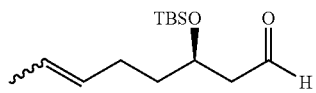

E/Z-mixture, only major peaks are assigned: IR (neat) 1728 cm$^{-1}$; $^1$H NMR (300 MHz, CDCl$_3$) δ 9.81 (t, J=2.4 Hz, 1H), 5.34-5.49 (m, 2H), 4.20 (quint, J=6.0 Hz, 1H), 2.52 (dd, J=2.4, 5.7 Hz, 2H), 1.99-2.06 (m, 2H), 1.55-1.66 (m, 5 H), 0.88 (s, 9H), 0.08 (s, 3H), 0.06 (s, 3H); $^{13}$C NMR (75 MHz, CDCl$_3$) δ 202.6, 130.6, 125.7, 68.0, 50.9, 37.8, 28.4, 26.0, 18.2, 18.1, −4.2, −4.5; LRMS (ESI) Calcd for C$_{14}$H$_{28}$O$_2$Si [M+Li] 263, Found 263.

EXAMPLE 10

Synthesis of (E)-2-(1-(tert-butyldimethylsilyloxy) but-1-enylthio)pyridine (3a)

The title compound was synthesized by the sequence of synthetic steps as shown by the reaction schemes below, including the synthesis of an intermediate thioester followed by the synthesis of the title product, a thiopyridyl ketene acetal.

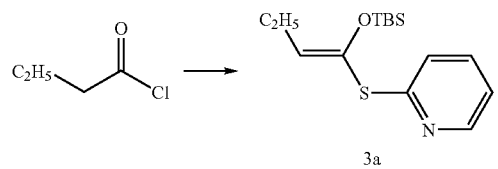

Synthesis of thioester: 2-mercaptopyridine (5.49 g, 4.93 mmol) was dissolved in 57 mL of dry dichloromethane in a round bottom flask to give a yellow solution, which was cooled to 0° C. Triethylamine (12.9 mL, 91.3 mmol) was added slowly via syringe, and subsequently butanoyl chloride (4.92 g, 46.1 mmol), dissolved in 56 mL of dichloromethane, was added slowly via cannula under nitrogen. The reaction mixture turned cloudy after the addition. The reaction was stirred for 12 h, and then concentrated in vacuo to give a bright yellow suspension. The product was taken up in pentane, washed with water (2×70 mL), and then with brine (2×70 mL), dried over MgSO$_4$, filtered and concentrated to give 8.58 g of a yellow liquid.

Synthesis of thiopyridyl ketene acetal: Lithium bis(trimethylsilylamide) (18.0 mL, 23.2 mmol) was placed in a 100 mL flask and cooled to −78° C. Dimethylformamide (3.03 mL, 39.18 mmol) was added via syringe followed by triethylamine (5.40 mL, 38.4 mmol), and then TBSCl (3.00 g, 19.9 mmol) was added as a solution in 15 mL of THF via syringe. Then S-pyridin-2-yl-butanethioate (3.50 g, 19.3 mmol) was dissolved in 30 mL of THF and added to the reaction mixture. The solution was stirred at −78° C. for 1 h, and then 50 mL of ethyl acetate were added and the mixture was allowed to warm to room temperature. The organic layer was washed with brine (3×30 mL), dried over MgSO$_4$, filtered and concentrated in vacuo. The yellow suspension was redissolved in hexane, filtered through celite and then concentrated in vacuo to obtain a yellow oil. Purification by flash chromatography (SiO$_2$, 40% EtOAc:hexanes) gave thiopyridyl ketene acetal (E)-3a (8.76 g, 92%, E/Z=>19:1) as a yellow oil: R$_f$=0.65 (40% EtOAc in hexanes).

$^1$H NMR (300 MHz, CDCl$_3$) δ 8.42 (dq, J=0.6, 4.8 Hz, 1H), 7.50 (dq, J=2.1, 8.4 Hz, 1H), 7.33 (td, J=0.9, 7.8 Hz, 1H), 7.00 (dq, J=0.9, 7.2 Hz, 1H), 5.40 (t, J=7.5 Hz, 1H), 3.34 (app q, J=7.5 Hz, 2H), 2.22 (m, 2H), 1.25 (app q, J=5.1 Hz, 3H), 0.87 (s, 9H), 0.08 (s, 6H); $^{13}$C NMR (125 MHz, CDCl$_3$) δ 160.7, 149.7, 136.8, 125.9, 121.8, 119.9, 25.9, 20.5, 18.4, 14.0, 4.2.

EXAMPLE 11

Synthesis of (E)-2-(1-(tert-butyldimethylsilyloxy) hex-1-enylthio)pyridine (3b)

The title compound was synthesized according to the reaction scheme shown below.

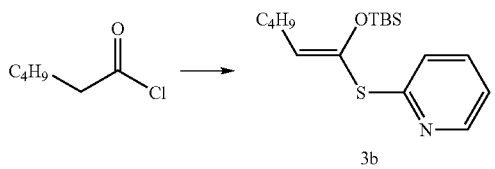

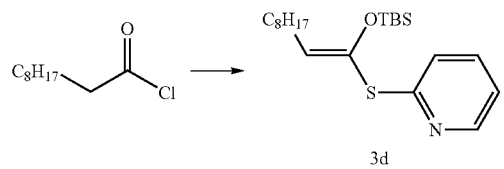

Prepared according to representative procedure described above in Example 9, using 2-mercaptopyridine (6.19 g, 55.6 mmol) dissolved in 53 mL of dry dichloromethane, triethylamine (14.5 mL, 103 mmol), and hexanoyl chloride (7.00 g, 52.0 mmol) dissolved in 50 mL of dichloromethane.

Lithium bis(trimethylsilylamide) (22.5 mL, 30.1 mmol), dimethylformamide (3.77 mL, 48.5 mmol), triethylamine (6.72 mL, 47.5 mmol), TBSCl (3.74 g, 24.6 mmol), and crude S-pyridin-2-yl hexanethioate (5.00 g, 23.9 mmol). This produced (E)-thiopyridyl ketene acetal 3b (5.1 g, 66%, E/Z=>19:1) as a yellow liquid. $^1$H NMR (500 MHz, CDCl$_3$) δ 8.42 (d, J=4.5 Hz, 1H), 7.55 (app t, J=7.0 Hz, 1H), 7.32 (d, J=8.5 Hz, 1H), 7.0 (m, 1H), 2.42-2.61 (m, 4H), 2.38 (app t, J=9.5 Hz, 2H), 2.18 (app q, J=7.0 Hz, 2H), 1.55-1.59 (m, 5H), 1.27 (br s, 3H), 0.87 (m, 6H), 0.07 (app t, J=4.5 Hz, 3H).

EXAMPLE 12

Synthesis of (E)-2-(1-(tert-butyldimethylsilyloxy) oct-1-enylthio)pyridine (3c) (Representative)

The title compound was synthesized according to the reaction scheme shown below.

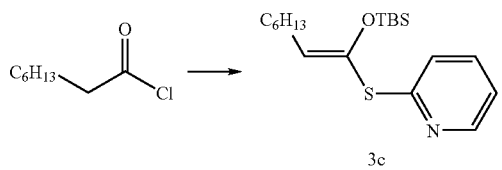

Prepared according to representative procedure described above in Example 9, using 2-mercaptopyridine (15.0 g, 135 mmol) dissolved in 150 mL of dry dichloromethane, triethylamine (35.1 mL, 250 mmol), and octanoyl chloride (20.5 g, 126 mmol) dissolved in 100 mL of dichloromethane.

Lithium bis(trimethylsilylamide) (31.7 mL, 42.4 mmol), dimethylformamide (5.32 mL, 68.4 mmol), triethylamine (9.48 mL, 67.0 mmol), TBSCl (5.28 g, 34.7 mmol), and crude S-pyridin-2-yl octanethioate (8.00 g, 19.30 mmol). This produced (E)-thiopyridyl ketene acetal 3c (9.1 g, 75%, E/Z=>19:1) as a yellow liquid: $^1$H NMR (300 MHz, CDCl$_3$) δ 8.56 (dt, J=0.9, 1.8 Hz, 1H), 7.65 (dt, J=2.1, 7.50 Hz, 1H), 7.52 (d, J=8.6 Hz, 1H), 7.21 (dq, J=0.9, 4.8 Hz, 1H), 2.89 (d, J=16.8 Hz, 2H), 2.61 (app t, J=8.4 Hz, 2H), 2.25 (app t, J=7.8 Hz, 2H), 1.55-160 (m, 5H), 1.20-1.21 (m, 11H), 0.81 (app t, J=6.9 Hz, 10H), 0.00 (s, 3H).

Another similar product, (E)-2-[1-(tert-butyl-dimethyl-silanyloxy)-dec-1-enylsulfanyl]-pyridine (3d), the formula of which is shown below was also obtained, using the representative procedure described above in Example 9.

Yet another similar product, 2-[1-(tri-Butyl-dimethyl-silanyloxy)-2-(2-methoxy-ethoxy)-vinylsulfanyl]-pyridine (3e) the formula of which is shown below was also obtained.

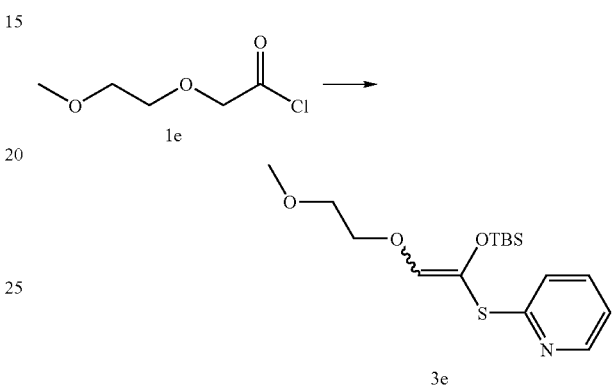

Compound (3e) was prepared according to representative procedure described above in Example 9, using 2-mercaptopyridine (1.77 g, 16.0 mmol) dissolved in 30 mL of dry dichloromethane, triethylamine (2.2 mL, 16.0 mmol), and acid chloride 1e (freshly prepared from acid; 14.5 mmol) dissolved in 10 mL of dichloromethane.

Lithium bis(trimethylsilylamide) (1M in THF; 10.6 mL, 10.6 mmol), dimethylformamide (1.36 mL, 17.6 mmol), triethylamine (2.45 mL, 17.6 mmol), TBSCl (1.37 g, 9.06 mmol), and crude ester (2.00 g, 8.80 mmol). This produced thiopyridyl ketene acetal 3e (2.17 g, 72%, E/Z, 1:1.2) as a yellow liquid.

Compound 3e-1: $^1$H NMR (300 MHz, CDCl$_3$) δ 8.40 (dd, J=0.6, 4.5 Hz, 1H), 7.52-7.55 (m, 1H), 7.42 (d, J=8.4 Hz, 1H), 6.98-7.02 (m, 1H), 6.32 (s, 1H), 3.95-3.98 (m, 2H), 3.59-3.62 (m, 2H), 3.39 (s, 3H), 0.88 (s, 9H), 0.16 (s, 6H).

Compound 3e2: $^1$H NMR (300 MHz, CDCl$_3$) δ 8.42-8.44 (m, 1H), 7.50-7.55 (m, 1H), 7.34-7.37 (m, 1H), 7.00-7.03 (m, 1H), 6.61 (s, 1H), 3.91-3.94 (m, 2H), 3.57-3.60 (m, 2H), 3.36 (s, 3H), 0.86 (s, 9H), 0.12 (s, 6H).

Another similar product, 2-[1-(triethylsilanyloxy)-propenylsulfanyl]-pyridine (3f), the formula of which is shown below was also obtained, using the representative procedure described above in Example 9.

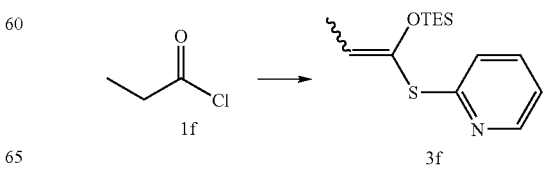

EXAMPLE 13

Synthesis of (2R,3S,4S)-3-Hexyl-4-(2-hydroxy-tridecyl)-oxetan-2-one (13d) by TMAL and Desilylation (Representative Procedure, Method A)

The title compound was synthesized according to the reaction scheme shown below.

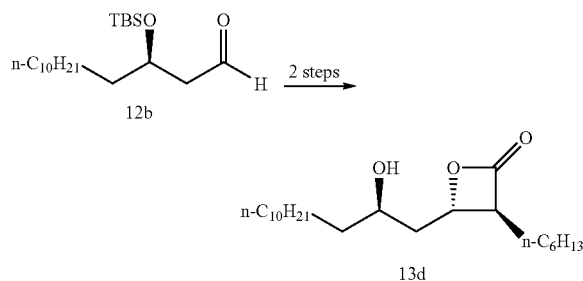

ZnCl$_2$ (398 mg, 2.92 mmol) was fused under vacuum and then allowed to cool to room temperature under a flow of nitrogen. 7.5 mL of dry CH$_2$Cl$_2$ was then added via syringe followed by a solution of 12b (500 mg, 1.46 mmol) in 2.5 mL of CH$_2$Cl$_2$ and ketene acetal 3c (719 mg, 2.04 mmol). The reaction mixture was stirred for 60 h at ambient temperature. 5 mL of pH 7 buffer were added and the mixture was stirred vigorously for 30 min, filtered through a pad of Celite, and washed with CH$_2$Cl$_2$. The organic filtrate was dried over Na$_2$SO$_4$, filtered, and concentrated. The residue was purified by flash chromatography on SiO$_2$ (10:1, hexanes:EtOAc) to provide mixture of two diastereomers (600 mg) as a pale yellow oil. Without further purification of two diastereomers, the mixture was used for the next step.

To a stirred solution of mixture of β-lactones (600 mg) in 24 mL of CH$_3$CN cooled to 0° C., 2.4 mL of HF (48%) was added dropwise. The mixture was stirred at 0° C. for 2 h, then it was allowed to warm to ambient temperature and stirred for an additional 5 h. The reaction mixture was diluted with 100 mL of Et$_2$O, quenched carefully with cold saturated NaHCO$_3$, and washed with brine. The organic layer was dried over Na$_2$SO$_4$, filtered, and concentrated. The residue was purified by flash chromatography on SiO$_2$ (10:1, hexanes:EtOAc) to provide mixture of two separable diastereomers (302 mg, 58% over 2 steps, dr 8:1) as a white solid.

13d (major): R$_f$=0.54 (20% EtOAc/hexanes); [α]$^{22}_D$=−30.9 (c 0.7, CHCl$_3$); IR (thin film) 1819 cm$^{-1}$; $^1$H NMR (500 MHz, CDCl$_3$) δ 4.51 (dt, J=4.3, 8.5 Hz, 1H), 3.79-3.86 (br m, 1H), 3.27 (ddd, J=4.0, 7.0, 8.5 Hz, 1H), 1.93 (ddd, J=3.0, 8.5, 14.5 Hz, 1H), 1.72-1.87 (m, 3H), 1.24-1.56 (m, 28H), 0.891 (t, J=6.0 Hz, 3H), 0.889 (t, J=6.0 Hz, 3H); $^{13}$C NMR (75 MHz, CDCl$_3$) δ 171.8, 75.8, 68.7, 56.8, 42.0, 38.3, 32.1, 31.7, 29.9, 29.83, 29.77 (2), 29.7, 29.6, 29.2, 27.9, 27.0, 25.6, 22.9, 22.7, 14.3, 14.2; LRMS (ESI) Calcd for C$_{22}$H$_{42}$O$_3$ [M+Li] 361, Found 361.

EXAMPLE 14

Synthesis of (2R,3S,4S)-4-(2-Hydroxy-tridecyl)-3-(2-methoxy-ethoxy)-oxetan-2-one (13h)

The title compound was synthesized according to the reaction scheme shown below.

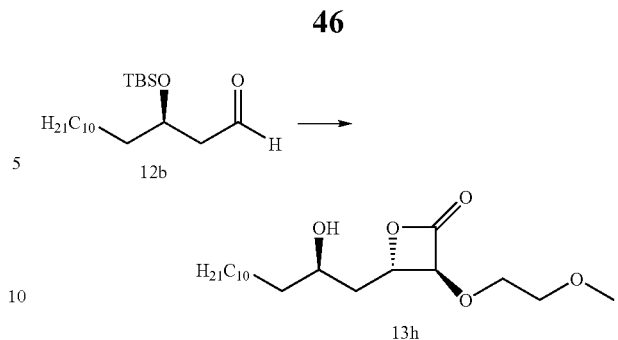

Prepared according to the representative procedure (TMAL and desilylation as discussed above, method A) using aldehyde 12b (0.200 g, 0.584 mmol), ketene acetal 3e (0.299 g, 0.876 mmol) and ZnCl$_2$ (0.159 g, 1.17 mmol) in 5 ml of CH$_2$Cl$_2$. Purification by flash chromatography on SiO$_2$ (4:1, hexanes:EtOAc) to provide mixture of two diastereomers as a pale yellow oil. Without further purification of two diastereomers, the mixture was used for the desilylation using 0.4 mL of HF pyridine in 2 mL of THF. Purification by flash chromatography on SiO$_2$ (2:1, hexanes:EtOAc) gave mixture of two separable diastereomers (29 mg, 15% over 2 steps, dr 7:1). $^1$H NMR (300 MHz, C$_6$D$_6$) δ 4.51-4.58 (m, 1H), 4.49 (d, J=3.6 Hz, 1H), 3.61 (ddd, J=3.0, 5.1, 11.1 Hz, 1H), 3.43-3.50 (m, 2H), 3.10-3.23 (m, 2H), 3.03 (s, 3H), 1.58-1.68 (m, 1H), 1.20-1.47 (m, 24H).

EXAMPLE 15

Synthesis of (2R,3S,4S)-3-Hexyl-4-(2-hydroxy-hex-5-enyl)-oxetan-2-one (13j)

The title compound was synthesized according to the reaction scheme shown below.

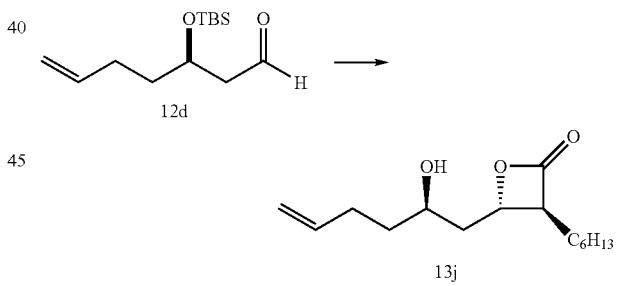

Prepared according to the representative procedure (TMAL and desilylation as discussed above, method A) using aldehyde 12d (0.500 g, 2.06 mmol), ketene acetal 3c (1.09 g, 3.09 mmol) and ZnCl$_2$ (0.562 g, 4.12 mmol) in 15 ml of CH$_2$Cl$_2$. Purification by flash chromatography on SiO$_2$ (10:1, hexanes:EtOAc) to provide mixture of two diastereomers as a pale yellow oil. Without further purification of two diastereomers, the mixture was used for the desilylation using 1.4 mL of HF (48%) in 24 mL of CH$_3$CN. Purification by flash chromatography on SiO$_2$ (10:1, hexanes:EtOAc) gave mixture of two separable diastereomers (0.314 g, 60% over 2 steps, dr ND). $^1$H NMR (300 MHz, C$_6$D$_6$) δ 5.68-5.82 (m, 1H), 4.95-5.03 (m, 2H), 4.15-4.02 (m, 1H), 3.39-3.42 (m, 1H), 2.82 (dt, J=3.9, 7.5 Hz, 1H), 1.85-1.96 (m, 2H), 1.15-1.53 (m, 14H), 0.97 (d, J=5.4 Hz, 1H), 0.88 (t, J=6.9 Hz, 3H); $^{13}$C NMR (75 MHz, C$_6$D$_6$) δ 171.7, 138.9, 115.4, 75.6, 68.1, 57.1, 42.5, 37.7, 32.2, 30.4, 29.7, 28.3, 27.4, 23.3, 14.6; LRMS (ESI) Calcd for $C_{15}H_{26}O_3$ [M+Li] 261, Found 261.

EXAMPLE 16

Synthesis of (2R,3S,4S)-3-Hexyl-4-(2-hydroxy-hept-5-enyl)-oxetan-2-one (13k)

The title compound was synthesized according to the reaction scheme shown below.

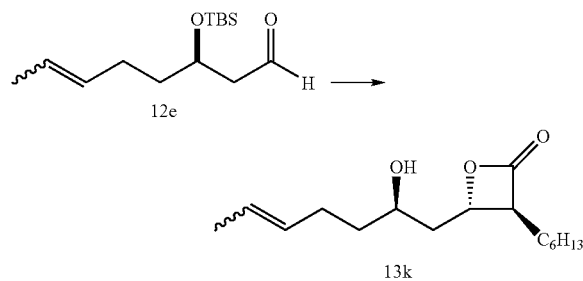

Prepared according to the representative procedure (TMAL and desilylation as discussed above, method A) using aldehyde 12e (1.00 g, 3.90 mmol), ketene acetal 3c (1.65 g, 4.68 mmol) and $ZnCl_2$ (1.06 g, 7.80 mmol) in 25 ml of $CH_2Cl_2$. Purification by flash chromatography on $SiO_2$ (10:1, hexanes:EtOAc) to provide mixture of two diastereomers as a pale yellow oil. Without further purification of two diastereomers, the mixture was used for the desilylation using 3.0 mL of HF (48%) in 50 mL of $CH_3CN$. Purification by flash chromatography on $SiO_2$ (10:1, hexanes:EtOAc) gave mixture of two separable diastereomers (646 mg, 62% over 2 steps, dr 9:1) as a waxy solid.

Spectroscopic data are reported for the major isomer 13k: $R_f$=0.41 (20% EtOAc/hexanes); IR (thin film) 3447, 1818 cm$^{-1}$; E/Z-mixture, only major peaks are assigned. $^1$H NMR (500 MHz, CDCl$_3$) δ 5.41-5.54 (m, 2H), 4.51 (dt, J=4.3, 8.5 Hz, 1H), 3.82-3.88 (m, 1H), 3.27 (dt, J=4.0, 11 Hz, 1H), 2.06-2.23 (m, 2H), 1.25-1.96 (m, 18H), 0.89 (t, J=6.8 Hz, 3H); $^{13}$C NMR (75 MHz, CDCl$_3$) δ 171.9, 130.5, 126.0, 75.8, 68.2, 56.6, 42.0, 37.7, 31.6, 29.1, 28.9, 27.8, 26.9, 22.7, 18.0, 14.2; LRMS (ESI) Calcd for $C_{16}H_{28}O_3$ [M+Li] 275, Found 275.

EXAMPLE 17

Synthesis of (2R,3S,4S)-3-ethyl-4-(2-hydroxytride-cyl)oxetan-2-one (13b) by TMAL and Desilylation (Representative Procedure, Method B)

The title compound was synthesized according to the reaction scheme shown below.

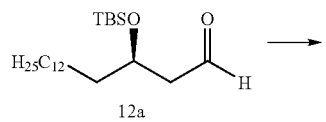

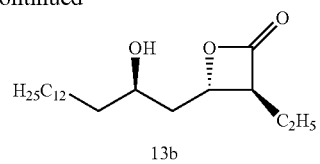

TMAL-procedure: Anhydrous $ZnCl_2$ (1.19 g, 8.76 mmol) was freshly fused under vacuum (~0.5 mm Hg) and cooled to room temperature under nitrogen, then 19 mL $CH_2Cl_2$ (appropriate volume to make the final concentration of aldehyde in $CH_2Cl_2$ ~0.15 M) was added, followed by the corresponding thiopyridylketene acetal 3a (2.16 g, 7.30 mmol), and stirred for 15 minutes before adding the aldehyde 12a (1.00 g, 2.92 mmol) neat. The suspension was stirred vigorously for 2 days. As the reaction proceeded, the bright yellow heterogeneous mixture became homogeneous with concurrent formation of white solid. The reaction was quenched by the addition of 15 mL of pH 7 buffer, the mixture was stirred vigorously for 1 hour and filtered through Celite with $CH_2Cl_2$. The organic layer was separated, dried over $Na_2SO_4$, filtered, taken up in $CH_2Cl_2$ (appropriate volume to make the final concentration ~0.15 M) and directly treated with $CuBr_2$ (3.41 g, 14.6 mmol). The resulting suspension was stirred for 2 hours, filtered through Celite and then washed with 10% aqueous $K_2CO_3$ and brine. The organic layer was dried over $Na_2SO_4$, filtered and concentrated in vacuo. The residue was purified by flash chromatography on $SiO_2$ (2% EtOAc in hexanes), affording a mixture of diastereoisomers (dr=7.7:1), as a pale yellow oil. Without further purification the product obtained was taken to the desilylation step.

Desilylation procedure: To a solution of the diastereoisomer mixture in 35 mL of dry $CH_3CN$ cooled at 0° C. was added 48% aqueous HF (0.31 mL) drop-wise. The reaction mixture was stirred at 0° C. for 2 hours and then warmed to room temperature. After 2 more hours, the reaction mixture was diluted with 15 mL of ether. The organic layer was separated, washed with a saturated solution of $NaHCO_3$, which was added slowly, (2×20 mL) and brine (2×20 mL). The residue was dried over $Na_2SO_4$, filtered and concentrated in vacuo. The solid mixture was purified by flash chromatography on $SiO_2$ (30% EtOAc in hexanes), to provide solid hydroxy β-lactone 13b (0.415 g, 48% 2 steps) as a mixture of diastereoisomers (dr=7.7:1). The diastereoisomers were partially separated via MPLC on $SiO_2$ (10% EtOAc in hexanes). Only 0.09 g of the major diastereoisomer (dr=>19:1) was separated completely. Spectroscopic data are reported for the major isomer 13b: $R_f$=0.65 (40% EtOAc/hexanes); $[α]^{22}_D$=−3.68 (c 0.38, CHCl$_3$); IR (thin film) 3443, 2926, 2854, 1822, 1459 cm$^{-1}$; $^1$H NMR (500 MHz, CDCl$_3$) δ 3.71 (app quint, J=4.5, 1H), 2.92-2.97 (m, 1H), 2.27 (app ddd, J=1.0, 4.0, 7.5 Hz, 1H), 0.66-1.02 (m, 24H), 0.49 (app t, J=12 Hz, 3H), 0.32 (app t, J=7.5 Hz, 3H); $^{13}$C NMR (125 MHz, CDCl$_3$) δ 171.7, 75.3, 68.8, 58.1, 42.0, 38.4, 32.1, 29.87, 29.85, 29.8 (2), 29.7, 29.57, 25.61, 22.9, 21.1, 14.4, 11.3, LRMS (ESI) Calcd for $C_{18}H_{34}O_3$ [M+Li] 304.87, Found 305.26.

EXAMPLE 18

Synthesis of (2R,3S,4S)-3-1Hexyl-4-(2-hydroxy-pentadecyl)-oxetan-2-one (13a)

The title compound was synthesized according to the reaction scheme shown below.

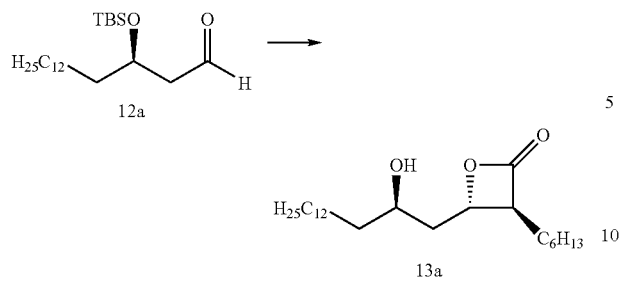

Prepared according to the representative procedure (TMAL and desilylation as discussed above, method B) using aldehyde 12a (0.500 g, 1.35 mmol), ketene acetal 3c (0.719 g, 2.04 mmol) and $ZnCl_2$ (0.398 g, 2.92 mmol) in 10 ml of $CH2Cl_2$. Purification by flash chromatography on $SiO_2$ (10:1, hexanes:EtOAc) to provide mixture of two diastereomers as a pale yellow oil. Without further purification of two diastereomers, the mixture was used for the desilylation using 1.1 mL of HF (48%) in 20 mL of $CH_3CN$. Purification by flash chromatography on $SiO_2$ (10:1, hexanes:EtOAc) gave mixture of two separable diastereomers (250 mg, 48% over 2 steps, dr 6:1) as a waxy solid. $[\alpha]^{22}_D=-30.5$ (c 1.1, $CHCl_3$).

EXAMPLE 19

Synthesis of (2R,3S,4S)-4-(2-Hydroxy-pentadecyl)-3-(2-methoxy-ethoxy)-oxetan-2-one (13c)

The title compound was synthesized according to the reaction scheme shown below.

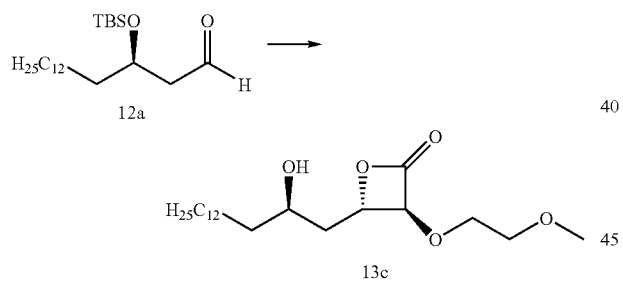

Prepared according to the representative procedure (TMAL and desilylation as discussed above, method B) using aldehyde 12a (0.250 g, 0.674 mmol), ketene acetal 3e (0.374 g, 1.10 mmol) and $ZnCl_2$ (0.250 g, 1.82 mmol) in 5 ml of $CH_2Cl_2$. Purification by flash chromatography on $SiO_2$ (4:1, hexanes:EtOAc) to provide mixture of two diastereomers as a pale yellow oil. The β-lactone was used for the desilylation using 0.4 mL of HF pyridine in 2 mL of THF. Purification by flash chromatography on $SiO_2$ (2:1, hexanes:EtOAc) gave 13c (28 mg, 11% over 2 steps, dr 19:1).

EXAMPLE 20

Synthesis of (2R,3S,4S)-3-butyl-4-(2-hydroxytridecyl)oxetan-2-one (13e)

The title compound was synthesized according to the reaction scheme shown below.

Prepared according to the representative procedure (TMAL and desilylation as discussed above, method B) using aldehyde 12b (0.40 g, 1.2 mmol), ketene acetal 3b (0.96 g, 2.9 mmol) and $ZnCl_2$ (0.49 g, 3.5 mmol) in 10 ml of $CH_2Cl_2$. The crude was purified by flash chromatography twice on $SiO_2$ eluting with 2% and 30% EtOAc in hexanes affording a mixture of diastereoisomers (dr=7.1:1). To a solution of two diastereoisomeric mixture in 30 mL of dry $CH_3CN$ cooled at 0° C. was added 48% aqueous HF (0.90 mL). The mixture was purified by flash chromatography on $SiO_2$ (2-10% EtOAc in hexanes). This produced white solid hydroxy β-lactone 13e (0.187 g, 49%) as a mixture of diastereisomers (dr=7.7:1). The diastereoisomers were partially separated via MPLC on $SiO_2$ (5% EtOAc in hexanes). Only 20 mg of the major diastereoisomer (dr=>19:1) was separated completely.

Spectroscopic data are reported for the major isomer 13e: $R_f=0.17$ (10% EtOAc/hexanes); $[\alpha]^{22}_D=-26.9$ (c 0.47, $CHCl_3$) IR (thin film) 3451, 2956, 2924, 2853, 1825, 1736, 1639 $cm^{-1}$; 1H NMR (500 MHz, $CDCl_3$) δ 4.55 (app. quint, J=4.4 Hz, 1H), 3.79-3.85 (m, 1H), 3.27 (ddd, J=4.2, 6.8, 8.3 Hz, 1H), 1.95 (ddd, J=0.9, 2.7, 9.0 Hz, 1H), 1.89 (ddd, J=0.9, 2.7, 9.0 Hz, 1H), 1.81 (ddd, J=4.9, 9.8, 14.4 Hz, 1H), 1.72-1.77 (m, 1H), 1.27-1.52 (m, 25H), 0.92 (app. t, J=7.1, 3H), 0.87 (app. t, J=6.8, 3H); $^{13}C$ NMR (125 MHz, $CDCl_3$) δ 171.87, 75.83, 68.75, 56.80, 42.06, 38.36, 32.15, 29.94, 29.87, 29.85, 29.79, 29.73, 29.58, 29.16, 27.65, 25.63, 22.92, 22.65, 14.36, 14.03; LRMS (ESI) Calcd for $C_{20}H_{38}O_3$ [M+Li] 333.51, Found 333.31.

EXAMPLE 21

Synthesis of (2R,3S,4S)-3-Ethyl-4-(2-hydroxy-tridecyl)-oxetan-2-one (13f)

The title compound was synthesized according to the reaction scheme shown below.

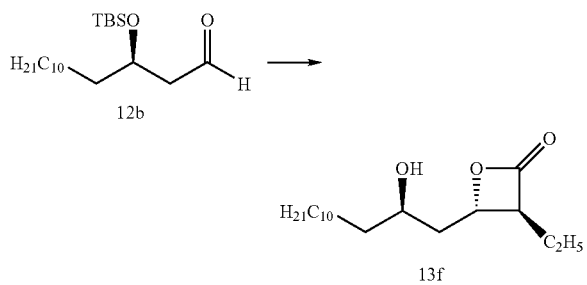

Spectroscopic data are reported for the major isomer 13f: $R_f=0.65$ (40% EtOAc/hexanes); $[\alpha]^{22}_D=-3.68$ (c 0.38, $CHCl_3$) IR (thin film) 3443, 2926, 2859, 1822, 1460 $cm^{-1}$; 1H NMR (500 MHz, $CDCl_3$) δ 3.71 (app. quint, J=4.5 Hz, 1H), 2.92-2.97 (m, 1H), 2.27 (app. ddd, J=1.0, 4.0, 7.5 Hz, 1H), 0.66-1.02 (m, 24H), 0.49 (app. t, J=12, 3H), 0.32 (app. t, J=7.5, 3H); $^{13}$C NMR (125 MHz, CDCl$_3$) δ 171.7, 75.3, 68.8, 58.1, 42.0, 38.4, 32.1, 29.87, 29.85, 29.8 (2), 29.7, 29.6, 25.6, 22.9, 21.1, 14.4, 11.3; LRMS (ESI) Calcd for C$_{18}$H$_{34}$O$_3$ [M+Li] 305, Found 305.

EXAMPLE 22

Synthesis of (2R,3S,4S)-4-(2-Hydroxy-tridecyl)-3-methyl-oxetan-2-one (13g)

The title compound was synthesized according to the reaction scheme shown below.

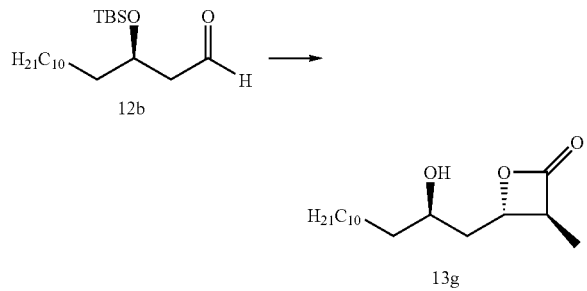

Prepared according to the representative procedure (TMAL and desilylation, as discussed above, method B) using aldehyde 12b (221 mg, 0.645 mmol), ketene acetal 3f (g, mmol) and ZnCl$_2$ (186 mg, 1.365 mmol) in 4.5 ml of CH$_2$Cl$_2$. Purification by flash chromatography on SiO$_2$ (97:3, pentane:Et$_2$O) to provide a mixture of two diastereomers as a pale yellow oil. Without further purification of two diastereomers, the mixture (77 mg, 0.193 mmol) was used for the desilylation using 0.16 mL of HF py (70%) in 4.5 mL of CH$_3$CN. Purification by flash chromatography on SiO$_2$ (5→10% EtOAc in CH$_2$Cl) gave a mixture of two inseparable diastereomers (18.5 mg, 20% over 2 steps) as a colorless solid. Major diastereomer 13g; $^1$H NMR (300 MHz, CDCl$_3$) δ 4.43 (m, 1H), 3.75-3.88 (br, 1H), 3.33 (dq, J=4.2, 7.5 Hz, 1H), 1.80-2.10 (m, 1H), 1.45-1.65 (br, 2H), 1.41 (d, J=7.5 Hz, 3H), 1.27 (br. s, 18H), 0.89 (t, J=6.9 Hz, 3H); $^{13}$C NMR (75 MHz, CDCl$_3$) δ 172.0, 77.8, 68.9, 51.7, 41.6, 38.4, 31.1, 29.83, 29.76, 29.73, 29.55, 25.7, 22.9, 14.3, 12.7.

EXAMPLE 23

Synthesis of (S)-3-octyl-(S)-4-((R)-2-tert-butyldimethylsiloxy)undecyl-oxetan-2-one (13i)

The title compound was synthesized according to the reaction scheme shown below.

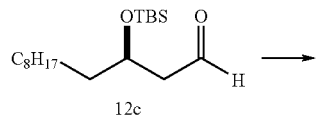

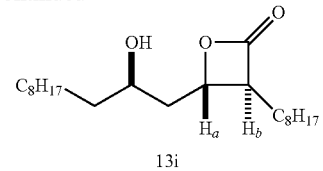

ZnCl$_2$ (229 mg, 1.68 mmol) was fused under vacuum and then allowed to cool to room temperature under a flow of nitrogen. 1.5 mL of dry DCM were then added via syringe followed by a solution of 12c (242 mg, 0.77 mmol) in 2.5 mL of DCM, and a solution of ketene acetal 3d (607 mg, 1.60 mmol) in 1.0 mL of DCM, and the mixture was stirred at room temperature.

After 69 h 3.0 mL of pH 7 buffer were added and the mixture was stirred vigorously for 15 min, filtered through Celite with DCM, and concentrated in vacuo. The residue was re-dissolved in 20 mL of DCM, 470 mg of CuBr$_2$ were added and the mixture was stirred at room temperature for 2 h. After filtration through Celite the liquid phase was washed three times with 10% aqueous K$_2$CO$_3$, and three times with brine, dried over Na$_2$SO$_4$, filtered and concentrated in vacuo. Purification of the residue via silica gel chromatography (95:5 hexane/EtOAc) yielded 272 mg of impure lactone as a slightly yellow oil.

IR (thin film) 2927, 2857, 1825, 1719, 1463, 1254, 1117, 1064, 834 cm$^{-1}$; $^1$H NMR major diastereomer (300 MHz, CDCl$_3$) δ 4.38 (ddd, J=8.4, 4.2, 4.2 Hz, 1H), 3.85 (m, 1H), 2.78 (td, J=7.3, 4.2 Hz, 1H), 1.38-1.70 (m, 4H), 1.32 (br. s, 26H), 1.22 (br., 2H), 0.99 (s, 9H), 0.36 (d, J=24 Hz, 3H), 0.12 (d, J=12 Hz, 3H); $^{13}$C NMR (75 MHz, CDCl$_3$) δ 171.9, 75.4, 68.8, 56.3, 42.1, 38.1, 32.1, 29.94, 29.84, 29.78, 29.71, 29.64, 29.33, 27.9, 27.0, 26.0, 25.7, 24.8, 22.9, 18.2, 14.3, −4.2, −4.5; LRMS (ESI$^+$) m/z [M+Li]: 475.

To a stirred solution of crude β-lactone (272 mg, 0.58 mmol) in 10 mL of MeCN cooled to 0° C., HF py (0.16 mL) was added slowly via a syringe. The mixture was stirred at 0° C. for 2 hrs, then it was allowed to warm to room temperature and stirred for an additional 10 hrs. 10.0 mL of Et$_2$O were added, and a white solid formed immediately. The mixture was washed three times with brine, dried over Na$_2$SO$_4$, filtered and concentrated in vacuo. The resulting yellow oil was re-dissolved in hexanes, washed with ice-cold 3% NaOH (2×) and brine (4×), dried over Na$_2$SO$_4$, filtered and concentrated in vacuo to afford a crystalline white solid. Purification of the crude material via silica gel chromatography (90:10 hexane/EtOAc) yielded the desired diastereomer of lactone 13i (108.8 mg, 53%), and 20.7 mg of a mixture of the two isomers.

$^1$H NMR pure isomer (300 MHz, CDCl$_3$) δ 4.50 (ddd, J=8.4, 4.2, 4.2 Hz, 1H), 3.71-3.86 (br, 1H), 3.25 (td, J=6.9, 3.9 Hz, 1H), 1.67-1.98 (m, 4H), 1.37-1.54 (br, 2H), 1.26 (br. s, 26H), 0.87 (t, J=6.9 Hz, 3H), $^{13}$C NMR (75 MHz, CDCl$_3$) δ 171.9, 75.8, 68.6, 56.7, 42.0, 38.3, 32.1, 32.0, 29.74, 29.70, 29.47, 29.36, 27.9, 27.0, 25.6, 22.8, 14.3.

EXAMPLE 24

Synthesis of (3S,4S)-3-hexyl-4-((R)-2-hydroxypropyl)oxetan-2-one (13l)

The title compound was synthesized according to the reaction scheme shown below.

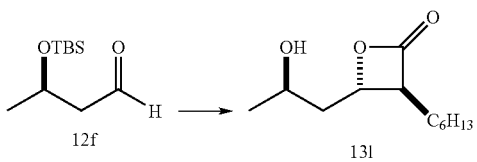

Prepared according to representative procedure described in Example 23 above, using anhydrous ZnCl$_2$ (0.510 g, 3.71 mmol), the corresponding thiopyridylketene acetal 3c (1.10 g, 3.10 mmol) and the aldehyde 12f (0.250 g, 1.24 mmol). The crude was purified by flash chromatography on SiO$_2$ eluting with 2% EtOAc in hexanes affording a mixture of diastereoisomers (dr=7.7:1). To a solution of the diastereoisomeric mixture in 36 mL of dry CH$_3$CN cooled at 0° C. was added 48% aqueous HF (0.96 mL). The mixture was purified by flash chromatography on SiO$_2$ (30% EtOAc in hexanes). This produced white solid hydroxy β-lactone 13l (0.112 g, 42%) as a mixture of diastereisomers (dr=7.7:1). The diastereoisomers were partially separated via MPLC on SiO$_2$ eluting (10% EtOAc in hexanes). Only 12 mg of the major diastereoisomer (dr=>19:1) was separated completely.

Spectroscopic data are reported for the major isomer 13l: $R_f$=0.27 (40% EtOAc/hexanes); $[\alpha]^{22}_D$=−39.80 (c 0.80, CHCl$_3$); IR (thin film) 3443, 2959, 2930, 2859, 1819 cm$^{-1}$; $^1$H NMR (500 MHz, CDCl$_3$) δ 4.07-4.10 (m, 1H), 3.44-3.47 (m, 1H), 2.71 (dddd, J=1.0, 4.0, 8.0, 12.0 Hz, 1H), 1.40-1.44 (m, 1H), 1.30-1.32 (m, 1H), 1.25 (ddd, J=1.0, 2.5, 7.6 Hz, 1H), 1.02-1.22 (m, 7H), 0.84 (dt, J=1.0, 7.50, Hz, 3H), 0.76 (dd, J=1.2, 7.3 Hz, 3H), 0.42 (br s, 2H); $^{13}$C (125 MHz, CDCl$_3$) δ 170.6, 74.7, 64.1, 56.2, 43.4, 31.7, 29.2, 27.8, 26.9, 24.1, 22.8, 14.1; LRMS (ESI) Calcd for C$_{12}$H$_{22}$O$_3$ [M+Li] 221.30, Found 221.17.

EXAMPLE 25

Synthesis of (2R,3S,4S)-3-Hexyl-4-(2-hydroxy-tridec-12-enyl)-oxetan-2-one (13m)

The title compound was synthesized according to the reaction scheme shown below.

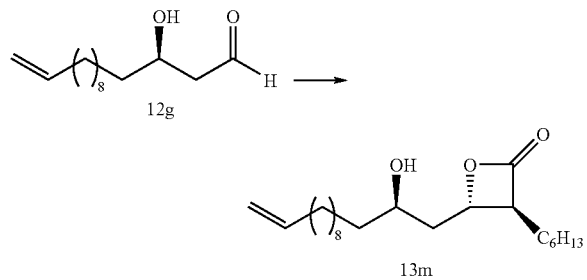

Prepared according to the representative procedure (TMAL and desilylation, as discussed above, method B) using aldehyde 12g (82 mg, 0.241 mmol), ketene acetal 3c (181 mg, 0.515 mmol) and ZnCl$_2$ (76 mg, 0.558 mmol) in 4 ml of CH$_2$Cl$_2$. Purification by flash chromatography on SiO$_2$ (97:3, pentane:Et$_2$O) to provide a mixture of two diastereomers as a pale yellow oil. Without further purification of two diastereomers, the mixture was used for the desilylation using 0.1 mL of HF py (70%) in 4 mL of CH$_3$CN. Purification by flash chromatography on SiO$_2$ (9:1, hexanes:EtOAc) gave a mixture of two partially separable diastereomers (43 mg, 50% over 2 steps, dr ~1;1; separation of the two diastereomers was not attempted) as a waxy solid.

Major diastereomer 13m; $^1$H NMR (300 MHz, C$_6$D$_6$) δ 5.81 (ddt, J=16.8, 10.2, 6.6 Hz, 1H), δ 5.10-4.99 (m, 2H), 4.27 (dt, J=4.2, 6.6 Hz, 1H), 3.33-3.45 (br, 1H), 2.91 (dt, J=3.9, 7.5 Hz, 1H), 2.03 (app. q, J=6.6 Hz, 2H), 1.00-1.70 (m, 22H), 0.89 (t, J=7.2 Hz 3H); $^{13}$C NMR (75 MHz, C$_6$D$_6$) δ 171.1, 139.6, 115.0, 75.9, 69.2, 57.2, 41.7, 38.3, 34.6, 32.2, 30.4, 30.3, 29.9, 29.71, 29.65, 28.4, 27.4, 26.2, 26.0, 23.3, 14.6.

EXAMPLE 26

Synthesis of (S)-3-((2S,3S)-3-hexyl-4-oxooxetan-2-yl)-2-hydroxypropyl 4-methylbenzenesulfonate (13n)

The title compound was synthesized according to the reaction scheme shown below.

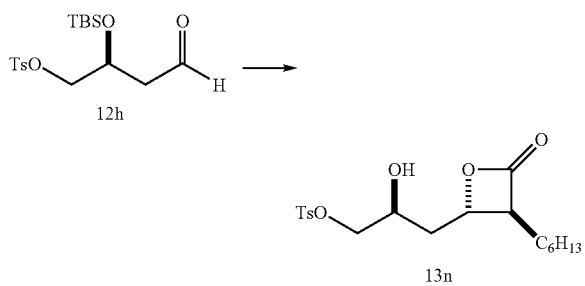

Prepared according to the representative procedure (TMAL and desilylation, as discussed above, method B) using aldehyde 12h (0.160 g, 0.429 mmol), ketene acetal 3c (0.386 g, 1.07 mmol) and ZnCl$_2$ (0.175 g, 1.29 mmol) in 5 ml of CH$_2$Cl$_2$. Purification by flash chromatography on SiO$_2$ (10:1, hexanes:EtOAc) to provide mixture of two diastereomers as a pale yellow oil. Without further purification of two diastereomers, the mixture was used for the desilylation using 0.33 mL of HF (48%) in 20 mL of CH$_3$CN. Purification by flash chromatography on SiO$_2$ (20:1, hexanes:EtOAc) gave mixture of two separable diastereomers (70 mg, 42% over 2 steps, dr 7.7:1). The diastereoisomers were partially separated via MPLC on SiO$_2$ (10% EtOAc in hexanes), only 13.4 mg of the major diastereoisomer (dr=>19:1) was separated completely.

Spectroscopic data are reported for the major isomer (13n): $R_f$=0.44 (40% EtOAc/hexanes); $[\alpha]^D_{22}$=−18.07 (c 0.4, CHCl$_3$) IR (thin film) 2956, 2929, 2858, 1822, 1726, 1685, 1599 cm$^{-1}$; 1H NMR (500 MHz, CDCl$_3$) δ 7.81 (dd, J=2.00, 8.50 Hz, 2H), 7.38 (dd, J=0.5, 8.00 Hz, 2H), 4.47 (app quint, J=4.00, Hz, 1H), 4.06 (dd, J=3.00, 11.00 Hz, 1H) 3.94 (dd, J=7.5, 11 Hz, 1H), 3.25-3.28 (m, 1H), 2.47 (s, 3H), 1.91-1.96 (m, 1H), 1.70-1.90 (m, 3H), 1.26-1.45 (m, 7H), 0.89 (app t, J=7 Hz, 4H); $^{13}$C NMR (125 MHz, CDCl$_3$) δ 171.2, 145.7, 132.6, 130.3, 128.2, 74.7, 73.7, 66.7, 56.9, 32.7, 31.7, 29.2, 27.9, 26.9, 22.7, 21.9, 14.3; LRMS (ESI) Calcd for C$_{19}$H$_{28}$O$_6$S [M+Li] 391, Found 391.

EXAMPLE 27

Synthesis of (3S,4S)-3-butyl-4-((R)-2-hydroxypropyl)oxetan-2-one (13o)

The title compound was synthesized according to the reaction scheme shown below.

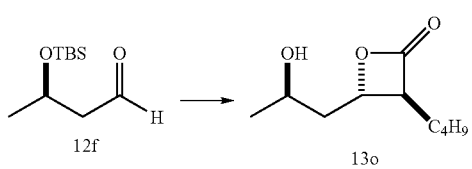

Prepared according to representative procedure described in Example 23 above, using anhydrous ZnCl$_2$ (0.51 g, 3.71 mmol), the corresponding thiopyridylketene acetal 3b (1.00 g, 3.10 mmol) and the aldehyde 12f (0.250 g, 1.24 mmol). The crude which was semi purified by flash chromatography on SiO$_2$ eluting with hexanes:EtOAc (50:1). The resulting product was a mixture of diastereoisomers (dr=7.7:1). To a solution of mixture of diastereoisomers in 36 mL of dry CH$_3$CN cooled at 0° C. was added 48% aqueous HF (0.96 mL). The white solid, mixture of diastereoisomers (dr=7.68:1) was purified by flash chromatography on SiO$_2$ eluting with hexanes:EtOAc (70:30). This produced mixture of two separable diastereomers (0.125 g, 47% over 2 steps). The diastereoisomers were partially separated via MPLC on SiO$_2$ eluting with hexanes:EtOAc (90:10), only 20.6 mg of the major diastereoisomer 13o (dr=>19:1) was separated completely.

R$_f$=0.45 (30% EtOAc/hexanes); [α]$^P_{22}$=−53.20 (c 0.92, CHCl$_3$) IR (thin film) 3444, 2961, 2931, 2860, 1819, 1739, 1647 cm$^{-1}$; $^1$H NMR (500 MHz, CDCl$_3$) δ 4.49 (app quint, J=4.0 Hz, 1H), 4.00-4.07 (m, 1H), 3.25-3.29 (m, 1H), 1.72-1.95 (m, 4H), 1.33-1.50 (m, 4H), 1.28 (d, J=6.5 Hz, 2H), 0.92 (app quint, J=7.00 Hz, 4H); $^{13}$C NMR (125 MHz, CDCl$_3$) 171.8, 75.7, 65.0, 56.8, 43.7, 29.1, 27.6, 24.6, 22.6, 14.0; LRMS (ESI) Calcd for C$_{10}$H$_{18}$O$_3$ [M+Li] 193, Found 193.

EXAMPLE 28

Synthesis of Orlistat (151) (Representative Procedure for Mitsnobu reaction)

The title compound was synthesized according to the reaction scheme shown below.

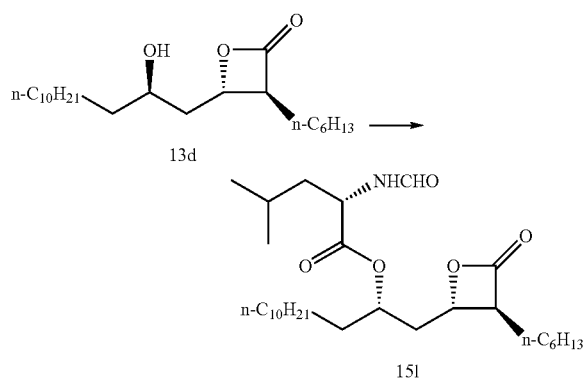

β-Lactone 13d (40.0 mg, 0.113 mmol), triphenylphosphine (77.7 mg, 0.296 mmol) and N-formyl-L-leucine (63.1 mg, 0.395 mmol) were placed in round-bottomed flask and azeotroped under vacuum with 0.5 mL of xylene for 2 h. 2 mL of dry THF was then added and the mixture was cooled to 0° C. Di-isopropyl-azo-dicarboxylate (DIAD) (57 μL, 0.30 mmol) was then added via a micro syringe and the mixture was stirred at 0° C. for 10 min, allowed to warm to room temperature and stirred for an additional 12 h. The mixture was then concentrated in vacuo and the residue was directly purified by flash chromatography on SiO$_2$ (10:1, hexanes:EtOAc) to provide Orlistat 151 (47 mg, 84%) as a white solid.

R$_f$=0.17 (20% EtOAc/hexanes); [α]$^{22}_D$=−31.2° (c 0.65, CHCl$_3$); IR (thin film) 1822, 1739, 1679 cm$^{-1}$; $^1$H NMR (500 MHz, CDCl$_3$) δ 8.23 (s, 1H), 5.90 (d, J=8.0 Hz, 1H), 5.01-5.06 (m, 1H), 4.70 (dt, J=4.5, 9.5 Hz, 1H), 4.30 (dt, J=4.5, 8.0 Hz, 1H), 3.24 (dt, J=4.0, 8.0 Hz, 1H), 2.17 (dt, J=7.5, 14.5 Hz, 1H), 2.01 (dt, J=4.5, 15.5 Hz, 1H), 1.21-1.85 (m, 33H), 0.982 (d, J=6.0 Hz, 3H), 0.977 (d, J=6.0 Hz, 3H), 0.87-0.91 (m, 6H); $^{13}$C NMR (75 MHz, CDCl$_3$) δ 172.1, 170.9, 160.8, 74.9, 72.9, 57.2, 49.8, 41.7, 38.9, 34.2, 32.1, 31.7, 29.8, 29.7, 29.6, 29.52, 29.49, 29.2, 27.8, 26.9, 25.3, 25.1, 23.1, 22.9, 22.7, 21.9, 14.3, 14.2; LRMS (ESI) Calcd for C$_{29}$H$_{53}$NO$_5$ [M+Li] 502, Found 502.

EXAMPLE 29

Synthesis of (S)-2-Formylamino-4-methyl-pentanoic Acid 1-((2S,3S,4S)-3-ethyl-4-oxo-oxetan-2-ylmethyl)-tetradecyl Ester (15a)

The title compound was synthesized according to the reaction scheme shown below.

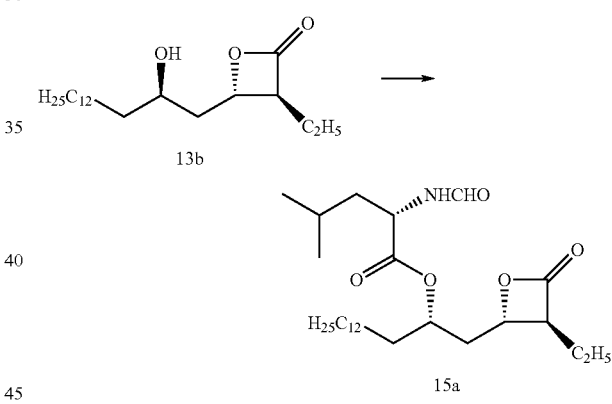

EXAMPLE 30

Synthesis of (S)-2-Formylamino-4-methyl-pentanoic Acid 1-((2S,3S,4S)-3-hexyl-4-oxo-oxetan-2-ylmethyl)-tetradecyl Ester (15b)

The title compound was synthesized according to the reaction scheme shown below.

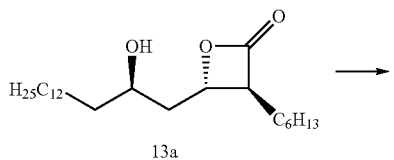

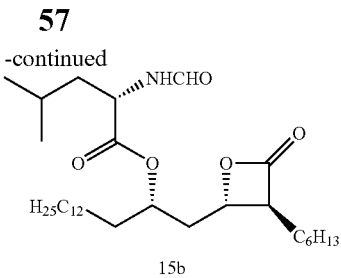

Prepared according to representative procedure described in Example 28 above (i.e., Mitsnobu reaction) using β-lactone 13a (30.0 mg, 0.0784 mmol), triphenylphosphine (66.6 mg, 0.254 mmol), N-formyl-L-leucin (47.3 mg, 0.296 mmol), and DIAD (49 μL, 0.25 mmol) in 1 mL of THF. Purification by flash chromatography on SiO$_2$ (4:1, hexanes:EtbAc) gave a desired β-lactone 15b (33 mg, 80%). $^1$H NMR (300 MHz, CDCl$_3$) δ 8.22 (s, 1H), 5.97 (d, J=8.1 Hz, 1H), 4.99-5.07 (m, 1H), 4.69 (dt, J=5.1, 9.0 Hz, 1H), 4.30 (quint, J=4.5 Hz, 1H), 3.22 (dt, J=4.2, 7.8 Hz, 1H), 2.17 (dt, J=7.8, 14.7 Hz, 1H), 2.00 (dt, J=4.8, 14.7 Hz, 1H), 1.25-1.82 (m, 37H), 0.86-0.98 (m, 12H); $^{13}$C NMR (75 MHz, CDCl$_3$) δ 172.2, 171.0, 160.8, 75.0, 73.0, 57.2, 49.8, 41.8, 38.9, 34.3, 32.1, 31.7, 29.89, 29.86 (3), 29.7, 29.64, 29.56, 29.5, 29.2, 27.8, 26.9, 25.3, 25.1, 23.1, 22.9, 22.7, 22.0, 14.3, 14.2; LRMS (ESI) Calcd for C$_{31}$H$_{57}$NO$_5$ [M+Li] 530, Found 530.

EXAMPLE 31

Synthesis of (2S,3S,4S)-Formylamino-acetic Acid 1-(3-hexyl-4-oxo-oxetan-2-ylmethyl)-tetradecyl Ester (15c)

The title compound was synthesized according to the reaction scheme shown below.

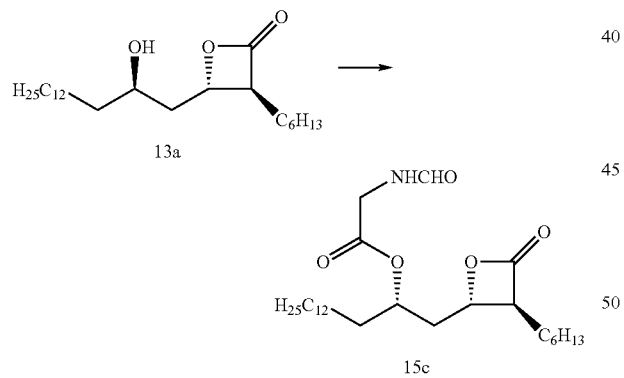

Prepared according to representative procedure described in Example 28 above (i.e., Mitsnobu reaction) using β-lactone 13a (20.0 mg, 0.0523 mmol), triphenylphosphine (44.4 mg, 0.169 mmol), N-formylglycine (20.4 mg, 0.197 mmol), and DIAD (33 μL, 0.169 mmol) in 0.7 mL of THF. Purification by flash chromatography on SiO$_2$ (4:1, hexanes:EtOAc) gave a desired β-lactone 15c (17.8 mg, 73%).

$^1$H NMR (300 MHz, C$_6$D$_6$) δ 7.72 (s, 1H), 5.16 (br, 1H), 4.94-5.01 (m, 1H), 4.06 (dt, J=4.8, 7.5 Hz, 1H), 3.78 (dd, J=6.0, 18.0 Hz, 1H), 3.69 (dd, J=5.7, 18.0 Hz, 1H), 2.74 (dt, J=4.2, 7.5 Hz, 1H), 1.72 (dt, J=8.1, 15.0 Hz, 1H), 1.15-1.47 (m, 35H), 0.88-0.94 (m, 6H); $^{13}$C NMR (75 MHz, C$_6$D$_6$) δ 170.7, 169.6, 160.9, 74.8, 72.8, 57.6, 40.5, 39.2, 34.8, 32.7, 32.2, 30.53 (2), 30.51, 30.5, 30.4, 30.3, 30.2, 30.1, 29.7, 28.1, 27.3, 25.9, 23.5, 23.3, 14.7, 14.6.

EXAMPLE 32

Synthesis of (S)-2-Formylamino-3-phenyl-propionic Acid 1-((2S,3S,4S)-3-hexyl-4-oxo-oxetan-2-ylmethyl)-tetradecyl Ester (15d)

The title compound was synthesized according to the reaction scheme shown below.

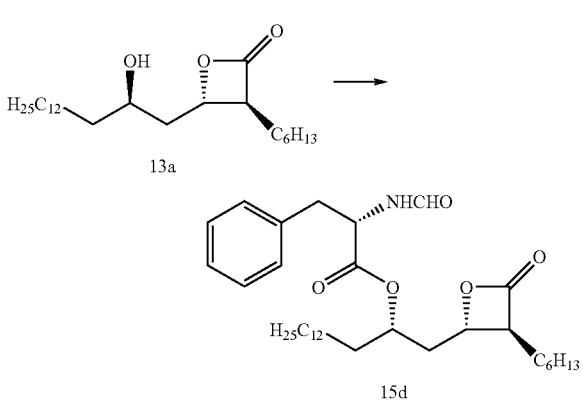

Prepared according to representative procedure described in Example 28 above (i.e., Mitsnobu reaction) using β-lactone 13a (20.0 mg, 0.0523 mmol), triphenylphosphine (44.4 mg, 0.169 mmol), N-formyl-L-leucin (47.3 mg, 0.296 mmol), and DIAD (49 μL, 0.25 mmol) in 1 mL of THF. Purification by flash chromatography on SiO$_2$ (4:1, hexanes:EtOAc) gave a desired β-lactone 15d (33 mg, 80%).

$^1$H NMR (300 MHz, C$_6$D$_6$) δ 7.57 (s, 1H), 6.96-7.12 (m, 5H), 5.08 (d, J=8.1 Hz, 1H), 4.92-4.98 (m, 1H), 4.87 (q, J=7.5 Hz, 1H), 3.93-3.99 (m, 1H), 3.01 (dd, J=6.3, 14.1 Hz, 1H), 2.84 (dd, J=7.2, 14.1 Hz, 1H), 2.70 (dt, J=4.2, 7.8 Hz, 1H), 1.73 (dt, J=7.5, 15.0 Hz, 1H), 1.14-1.54 (m, 35H), 0.88-0.95 (m, 6H); LRMS (ESI) Calcd for C$_{34}$H$_{55}$NO$_5$ [M+Li] 564, Found 564.

EXAMPLE 33

Synthesis of (S)-2-Formylamino-3-(3H-imidazol-4-yl)-propionic Acid 1-((2S,3S,4S)-3-hexyl-4-oxo-oxetan-2-ylmethyl)-tetradecyl Ester (15e)

The title compound was synthesized according to the reaction scheme shown below.

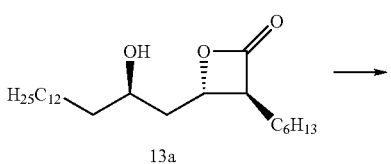

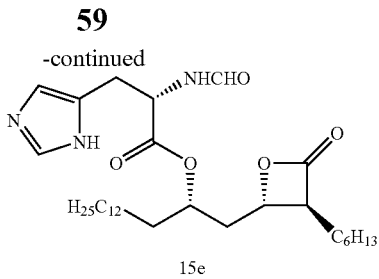

15e

Prepared according to representative procedure described in Example 28 above (i.e., Mitsnobu reaction) using β-lactone 13a (40.0 mg, 0.105 mmol), triphenylphosphine (88.9 mg, 0.339 mmol), N-formyl-L-histidine (72.3 mg, 0.395 mmol), and DIAD (66 μL, 0.34 mmol) in 3 mL of THF. Purification by flash chromatography on $SiO_2$ (2:1, hexanes:EtOAc) gave a desired β-lactone 15e (10 mg, 17%). $^1$H NMR (300 MHz, $C_6D_6$) δ 7.91 (s, 1H), 7.78 (s, 1H), 6.97 (s, 1H), 6.82 (d, J=7.5 Hz, 1H), 4.93-4.99 (m, 2H), 4.82 (quint, J=6.6 Hz, 1H), 4.22 (dt, J=3.9, 6.3 Hz, 1H), 2.99 (dd, J=5.1, 14.1 Hz, 1H), 2.86 (dd, J=5.4, 15.0 Hz, 1H), 2.78-2.82 (m, 1H), 1.88 (dt, J=6.9, 14.7 Hz, 1H), 1.16-1.63 (m, 31H), 0.87-0.96 (m, 100H).

EXAMPLE 34

Synthesis of (S)-2-Formylamino-4-methyl-pentanoic Acid 1-[(2S,3S,4s)-3-(2-methoxy-ethoxy)-4-oxo-oxetan-2-ylmethyl]-tetradecyl Ester (15f)

The title compound was synthesized according to the reaction scheme shown below.

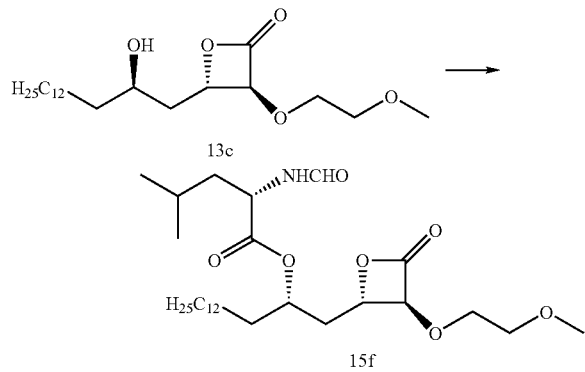

Prepared according to representative procedure described in Example 28 above (i.e., Mitsnobu reaction) using β-lactone 13c (27.0 mg, 0.0725 mmol), triphenylphosphine (63.5 mg, 0.242 mmol), N-formylleucin (45.2 mg, 0.283 mmol), and DIAD (47 μL, 0.24 mmol) in 2 mL of THF. Purification by flash chromatography on $SiO_2$ (2:1, hexanes:EtOAc) gave a desired β-lactone 15f (25 mg, 67%).

$^1$H NMR (300 MHz, $C_6D_6$) δ 7.88 (s, 1H), 5.45 (d, J=8.4 Hz, 1H), 4.97-5.05 (m, 1H), 4.83 (dt, J=4.5, 9.3 Hz, 1H), 4.42 (ddd, J=3.9, 5.1, 8.7 Hz, 1H), 4.31 (d, J=3.6 Hz, 1H), 3.62 (ddd, J=3.0, 5.4, 11.1 Hz, 1H), 3.41 (ddd, J=2.7, 6.3, 10.8 Hz, 1H), 3.08-3.21 (m, 2H), 3.02 (s, 3H), 1.21-1.69 (m, 29H), 0.84-0.94 (m, 9H); $^{13}$C NMR (75 MHz, $C_6D_6$) δ 172.5, 168.0, 160.8, 88.0, 76.4, 72.34, 72.28, 70.2, 58.9, 50.0, 41.6, 37.3, 34.7, 32.7, 30.54, 30.51 (3), 3.4, 30.3, 30.2, 30.1, 25.7, 23.5, 22.0, 14.7.

EXAMPLE 35

Synthesis of (S)-2-Formylamino-4-methyl-pentanoic Acid 1-((2S,3S,4S)-3-methyl-4-oxo-oxetan-2-ylmethyl)-dodecyl Ester (15g)

The title compound was synthesized according to the reaction scheme shown below.

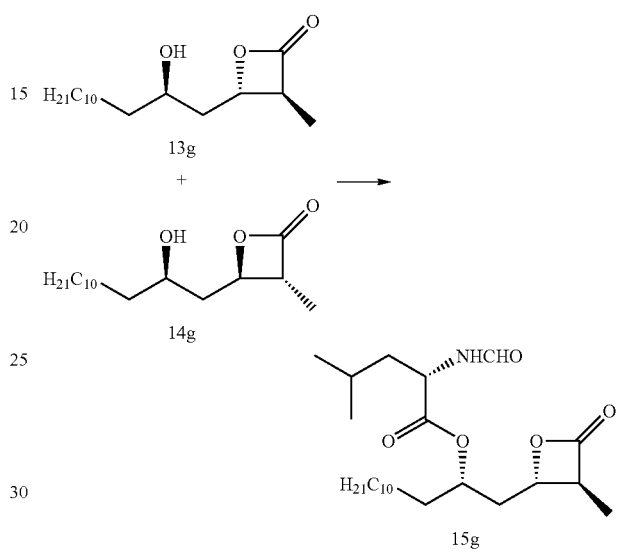

Prepared according to representative procedure described in Example 28 above (i.e., Mitsnobu reaction) using the mixture of β-lactones 13g and 14g (110.9 mg, 0.0418 mmol), triphenylphosphine (32.8 mg, 0.125 mmol), N-formylleucine (23.2 mg, 0.146 mmol), and DIAD (25 L, 0.13 mmol) in 1 mL of THF. Purification by flash chromatography on $SiO_2$ (3:2, hexanes:EtOAc) followed by a second purification by flash chromatography on $SiO_2$ (0.4:1:3 THF:CHCl$_3$:hexanes) gave the desired β-lactone as a mixture of diastereomers. The two diastereomers could be separated by MPLC (65:35, hexanes: EtOAc) affording desired product 15g (6.8 mg, 38%), and the β-Lactone diastereomer 16b (4.4 mg, 24%).

Major diastereomer (15g); $^1$H NMR (300 MHz, CDCl$_3$) δ 8.23 (s, 1H), 5.92 (d, J=8.7 Hz, 1H), 4.98-5.10 (m, 1H), 4.69 (td, J=4.8, 8.4, 1H), 4.23 (ddd, J=8.4, 4.2, 4.2 Hz, 1H), 3.28 (dq, J=4.2, 7.8 Hz, 1H), 1.96-2.26 (m, 2H), 1.51-1.75 (m, 5H), 1.40 (d, J=7.8 Hz, 3H), 1.26 (br. s, 18H), 0.98 (d, J=6.0 Hz, 6H), 0.89 (t, J=6.6 Hz, 3H); $^{13}$C NMR (75 MHz, CDCl$_3$) δ 172.2, 171.4, 160.8, 76.5, 72.8, 51.8, 49.9, 41.8, 38.7, 34.4, 32.1, 29.92, 29.83, 29.75, 29.65, 29.56, 29.51, 25.3, 25.1, 23.1, 22.9, 22.0, 14.3, 12.6.

EXAMPLE 36

Synthesis of (S)—((R)-1-((2S,3S)-3-ethyl-4-oxoox-etan-2-yl)tridecan-2-yl) 2-methanamido-4-methyl-pentanoate (15h)

The title compound was synthesized according to the reaction scheme shown below.

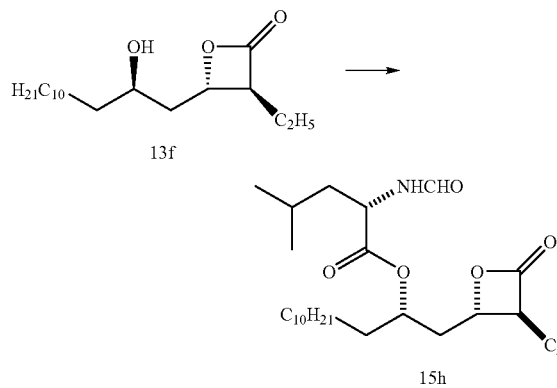

Hydroxy β-lactone 13f (17.7 mg, 0.0594 mmol), N-formylleucine (33.4 mg, 0.209 mmol), and triphenylphosphine (53.4 mg, 0.203 mmol) were placed in a 10 mL round bottom flask; 0.5 mL of xylene were added and the mixture was azeotroped in vacuo for 1.0 h. THF (1.4 mL) was then added under N₂ and the solution was cooled to 0° C. DIAD (37.9 μL, 0.1947 mmol) was added and the reaction mixture was stirred at 0° C. for 10 minutes, then it was allowed to warm to room temperature and stirred overnight. The mixture was concentrated in vacuo, and purified twice by chromatography (SiO₂, 10 to 30% EtOAc:hexanes) to afford β-lactone 2b (6 mg, 25%).

$R_f$=0.26 (30% EtOAc/hexanes); $[\alpha]^{22}_D$=−3.68 (c 0.4, CHCl₃), IR (thin film) 2926, 2856, 1828, 1740, 1671 cm⁻¹; ¹H NMR (500 MHz, CDCl₃) δ 8.23 (br s, 1H), 5.90 (d, J=8.5 Hz, 1H), 5.04 (app quint, J=5.5 Hz, 1H), 4.69 (ddd, J=5.0, 8.5, 13.0 Hz, 1H), 4.30-4.33 (m, 1H), 3.18-3.22 (m, 1H), 2.19 (app quint, J=7.0 Hz, 1H), 2.00 (dt, J=4.5, 19.0 Hz, 1H), 1.64-1.70 (m, 2H), 1.54-1.60 (m, 19H) 1.22-1.32 (m, 6H), 1.042 (dppt, J=7.5 Hz, 3H) 0.97 (dd, J=1.5, 4.5 Hz, 4H), 0.90 (appt, J=7.5 Hz, 3H); ¹³C NMR (125 HMz, CDCl₃) δ 172.2, 160.9, 77.0, 76.9, 74.4, 72.9, 58.6, 49.9, 46.8, 38.6, 34.3, 32.1, 29.84, 29.8, 29.77, 29.66, 29.5, 25.3, 25.1, 23.1, 22.9, 22.0, 21.0, 14.4, 11.2; LRMS (ESI) Calcd for C₂₅H₄₅NO₅ [M+Li] 446.63, Found 446.35.

EXAMPLE 37

Synthesis of (R)-1-((2S,3S)-3-ethyl-4-oxooxetan-2-yl)tridecan-2-yl 2-methanamidoethanoate (15i)

The title compound was synthesized according to the reaction scheme shown below.

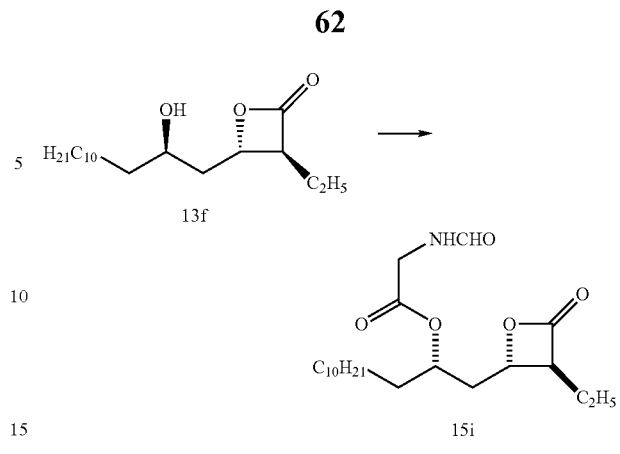

Prepared according to the procedure described in Example 36, above. Hydroxy β-lactone 13f (10 mg, 0.033 mmol), N-formylglycine (12.0 mg, 0.120 mmol), triphenylphosphine (26.6 mg, 0.099 mmol), and 0.5 mL of xylene were combined and the mixture was azeotroped in vacuo for 1.0 h. THF (1.4 mL) was then added followed by DIAD (21.0 μL, 0.108 mmol). After 12 hours the mixture was concentrated in vacuo, and purified by chromatography (SiO₂, 10 to 30% EtOAc: hexanes) to afford β-lactone 15i (5.5 mg, 43%).

$R_f$=0.23 (40% EtOAc/hexanes); $[\alpha]^{22}_D$=−11.0 (c 0.7, CHCl₃), IR (thin film) 2926, 2854, 1822, 1743, 1685 cm⁻¹; ¹H NMR (500 MHz, CDCl₃) δ 8.19 (br s, 1H), 5.98 (br s, 1H), 5.04-5.09 (m, 1H) 4.28 (app quint, J=4.5 Hz, 1H), 3.12 (ddd, J=3.5, 7.0, 11.5 Hz, 1H), 2.06-2.12 (m, 1H), 1.93-1.97 (m, 1H), 1.69-1.81 (m, 2H), 1.18-1.23 (m, 22H), 0.97 (app t, J=7.0 Hz, 3H), 0.81 (app t, J=7.0, 3H); ¹³C NMR (125 HMz, CDCl₃) δ 169.5, 161.2, 74.7, 73.3, 58.6, 40.4, 39.1, 34.4, 32.2, 30.0, 29.9, 29.8, 29.7, 29.6, 29.5, 25.4, 25.3, 22.9, 21.0, 14.4, 11.3; LRMS (ESI) Calcd for C₂₁H₃₇NO₅ [M+H] 384.52, Found 384.28.

EXAMPLE 38

Synthesis of (2S,3S,4S)-Benzoic Acid 1-(3-hexyl-4-oxo-oxetan-2-ylmethyl)-dodecyl Ester (15j)

The title compound was synthesized according to the reaction scheme shown below.

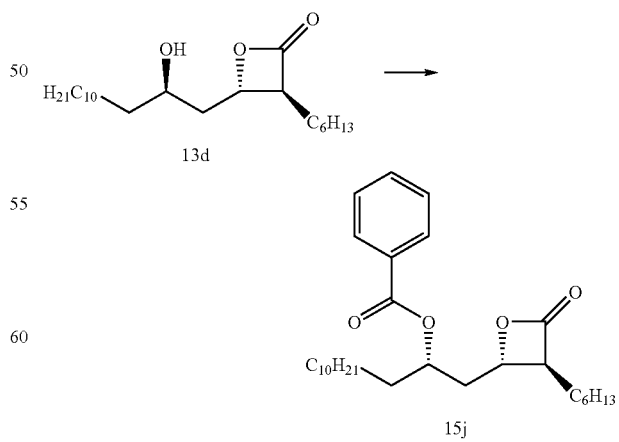

Prepared according to representative procedure described in Example 28 above (i.e., Mitsnobu reaction) using β-lactone 13d (15.0 mg, 0.0423 mmol), triphenylphosphine (15.5 mg, 0.0592 mmol), benzoic acid (60.3 mg, 0.0846 mmol), and DIAD (11 µL, 0.059 mmol) in 1.5 mL of THF. Purification by flash chromatography on $SiO_2$ (25:1, hexanes:EtOAc) gave a desired β-lactone 15j (Yield is not determined).

$^1$H NMR (300 MHz, $CDCl_3$) δ 7.44-8.06 (m, 5H), 5.22-5.26 (m, 1H), 4.41 (dt, J=3.9, 6.9 Hz, 1H), 3.25 (dt, J=4.2, 7.8 Hz, 1H), 2.30-2.37 (m, 1H), 2.09-2.16 (m, 1H), 1.71-1.82 (m, 4H), 1.25 (br. m, 26H), 0.84-0.91 (m, 6H); LRMS (ESI) Calcd for $C_{29}H_{46}O_4$ [M+Li] 465, Found 465.

EXAMPLE 39

Synthesis of (S)-1-((2S,3S)-3-hexyl-4-oxooxetan-2-yl)tridecan-2-yl 2-(dimethylamino)ethanoate (15k)

The title compound was synthesized according to the reaction scheme shown below.

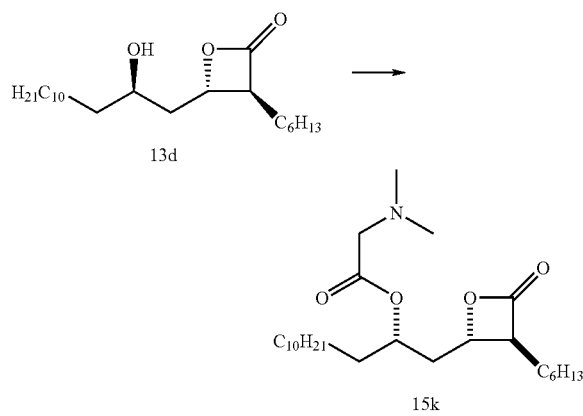

Prepared according to representative procedure described in Example 28 above (i.e., Mitsnobu reaction) using hydroxy β-lactone 13d (26.0 mg, 0.085 mmol), N,N-dimethylglycine (30.6 mg, 0.297 mmol), triphenylphosphine (75.7 mg, 0.289 mmol), and 0.5 mL of xylene were combined and the mixture was azeotroped in vacuo for 1 h. THF (7 mL) was then added followed by DIAD (54.0 µL, 0.108 mmol). After 12 hours the mixture was concentrated in vacuo, and purified by chromatography ($SiO_2$, 30% EtOAc:hexanes) to afford 27.3 mg (73.1%) of β-lactone 15k.

$R_f$=0.24 (40% EtOAc/hexanes); $[α]^{22}_D$=−5.72 (1.2, $CHCl_3$); IR (thin film) 2925, 2854, 1827, 1743, 1461 $cm^{-1}$; $^1$H NMR (500 MHz, $CDCl_3$) δ 5.07-5.12 (m, 1H), 4.32 (ddd, J=4.0, 5.5, 7.5, Hz, 1H), 3.20 (ddd, J=4.0, 8.0, 12.0 Hz, 1H), 3.19 (s, 3H), 2.37 (s, 6H), 2.18 (app. t, J=8.0 Hz, 1H), 2.15 (app. t, J=8.0 Hz, 1H), 2.00 (dd, J=3.0, 5.0 Hz, 1H), 1.97 (dd, J=3.5, 5.5 Hz, 1H), 1.69-1.82 (m, 4H), 1.52-1.68 (m, 4H), 1.24-1.44 (m, 21H), 0.88 (dt, J=1.5, 6.5 Hz, 24H); $^{13}$C NMR (125 MHz, $CDCl_3$) δ 171.3 (2), 75.2, 71.6, 60.0, 57.2, 45.5, 39.2, 34.5, 32.1, 31.7, 29.85 (2), 29.76, 29.7, 29.6, 29.5 29.2, 27.9, 27.0, 25.5, 22.9 (2), 22.8, 14.4 (2); LRMS (ESI) Calcd for $C_{26}H_{49}NO_4$ [M+H] 440.67, Found 440.38.

EXAMPLE 40

Synthesis of (2S,3S,4S)-Formylamino-acetic Acid 1-(3-hexyl-4-oxo-oxetan-2-ylmethyl)-dodecyl Ester (15m)

The title compound was synthesized according to the reaction scheme shown below.

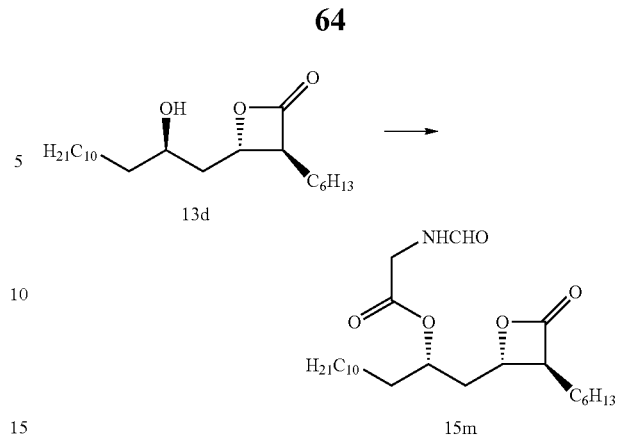

Prepared according to representative procedure described in Example 28 above (i.e., Mitsnobu reaction) using β-lactone 13d (40.0 mg, 0.113 mmol), triphenylphosphine (74.1 mg, 0.283 mmol), N-formylglycine (40.7 mg, 0.395 mmol), and DIAD (55 µL, 0.28 mmol) in 2 mL of THF. Purification by flash chromatography on $SiO_2$ (4:1, hexanes:EtOAc) gave a desired β-lactone 15m (43 mg, 87%).

$^1$H NMR (300 MHz, $C_6D_6$) δ 7.79 (s, 1H), 5.45 (br, 1H), 4.95-5.02 (m, 1H), 4.08 (dt, J=5.1, 7.2 Hz, 1H), 3.81 (dd, J=5.7, 18.0 Hz, 1H), 3.73 (dd, J=5.7, 18.3 Hz, 1H), 2.78 (dt, J=4.2, 7.8 Hz, 1H), 1.75 (dt, J=8.1, 15.0 Hz, 1H), 1.17-1.52 (m, 31H), 0.87-0.94 (m, 6H); $^{13}$C NMR (75 MHz, $C_6D_6$) δ 170.8, 169.7, 161.1, 74.9, 72.8, 57.6, 40.6, 39.2, 34.8, 32.7, 32.2, 30.47, 30.45, 30.40, 30.3, 30.2, 30.1, 29.7, 28.2, 27.4, 25.9, 23.5, 23.3, 14.7, 14.6.

EXAMPLE 41

Synthesis of 2-Formylamino-3-methyl-butyric Acid (2S,2R,3S,4S)-1-(3-hexyl-4-oxo-oxetan-2-ylmethyl)-hex-4-enyl Ester (15n)

The title compound was synthesized according to the reaction scheme shown below.

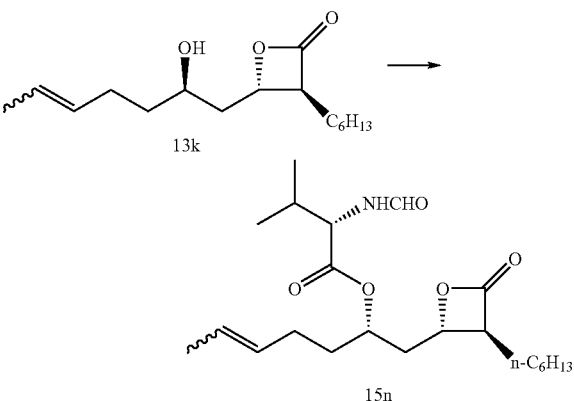

Prepared according to representative procedure described in Example 28 above (i.e., Mitsnobu reaction) using β-lactone 13k (20.0 mg, 0.0745 mmol), triphenylphosphine (27.4 mg, 0.104 mmol), N-formyl-L-valine (21.6 mg, 0.149 mmol), DIAD (20 µL, 0.10 mmol) in 1 mL of THF. Purification by flash chromatography on $SiO_2$ (9:1, hexanes:EtOAc) gave a desired β-lactone 15n (13.3 mg, 45%) as a colorless oil. E/Z-mixture, only major peaks are assigned.

$R_f$=0.24 (30% EtOAc/hexanes); [α]$^{22}_D$ −7.95 (0.9, CHCl$_3$); IR (thin film) 1823, 1737, 1670 cm$^{-1}$; $^1$H NMR (500 MHz, CDCl$_3$) δ 8.28 (s, 1H), 6.05 (d, J=8.0 Hz, 1H), 5.32-5.50 (m, 2H), 5.03-5.08 (m, 1H), 4.64 (ddd, J=4.5, 7.5, 16.5 Hz, 1H), 4.30 (dt, J=4.0, 8.0 Hz, 1H), 3.23 (dt, J=4.5, 7.0 Hz, 1H), 2.06-2.26 (m, 3H), 2.02 (dt, J=5.5, 14.5 Hz, 2H), 1.64-1.85 (m, 6H), 1.28-1.48 (m, 9H), 1.01 (d, J=6.5 Hz, 3H), 0.93 (d, J=7.0 Hz, 3H), 0.89 (t, J=6.6 Hz, 3H); $^{13}$C NMR (75 MHz, CDCl$_3$) δ 171.2, 170.9, 161.0, 129.4, 126.6, 74.8, 72.5, 57.3, 56.1, 38.8, 33.9, 31.7, 31.2, 29.2, 28.4, 27.9, 26.9, 22.7, 19.5, 18.11, 17.7, 14.2; LRMS (ESI) Calcd for C$_{22}$H$_{37}$NO$_5$ [M+H] 396, Found 396.

EXAMPLE 42

Synthesis of (S)-2-Formylamino-3-phenyl-propionic Acid 1-((2S,3S,4S)-3-hexyl-4-oxo-oxetan-2-ylmethyl)-hex-4-enyl Ester (15o)

The title compound was synthesized according to the reaction scheme shown below.

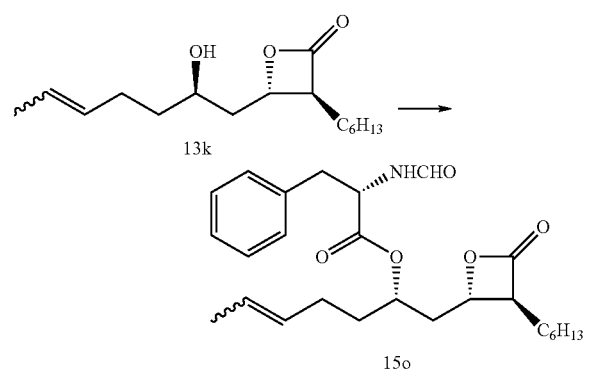

Prepared according to representative procedure described in Example 28 above (i.e., Mitsnobu reaction) using β-lactone 13k (20.0 mg, 0.0745 mmol), triphenylphosphine (27.4 mg, 0.104 mmol), N-formyl-L-phenylalanine (28.8 mg, 0.149 mmol), and DIAD (20 μL, 0.10 mmol) in 2 mL of THF. Purification by flash chromatography on SiO$_2$ (4:1, hexanes:EtOAc) gave a desired β-lactone 15o (yield is not determined).

E/Z-mixture, only major peaks are assigned. $^1$H NMR (300 MHz, CDCl$_3$) δ 8.18 (s, 1H), 7.17-7.32 (m, 5H), 5.99 (d, J=7.8 Hz, 1H) 5.30-5.47 (m, 2H), 4.97-5.05 (m, 1H), 4.91 (q, J=6.9 Hz, 1H), 4.28 (dt, J=5.1, 7.8 Hz, 1H), 3.06-3.24 (m, 3H), 1.26-2.10 (m, 19H), 0.90 (t, J=6.6 Hz, 3H); $^{13}$C NMR (125 MHz, CDCl$_3$) δ 171.0, 170.9, 160.6, 135.7, 129.5, 129.4, 128.9, 127.6, 126.5, 74.7, 72.7, 57.3, 52.3, 38.8, 38.0, 33.9, 31.7, 29.2, 28.3, 27.8, 26.9, 22.7, 18.1, 14.3; LRMS (ESI) Calcd for C$_{26}$H$_{37}$NO$_5$ [M+H] 444, Found 444.

EXAMPLE 43

Synthesis of (S)-2-Formylamino-4-methyl-pentanoic Acid 1-((2S,3S,4S)-3-hexyl-4-oxo-oxetan-2-ylmethyl)-pent-4-enyl Ester (15p)

The title compound was synthesized according to the reaction scheme shown below.

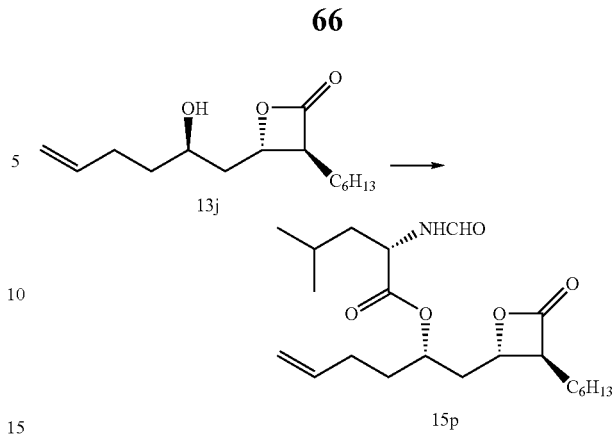

Prepared according to representative procedure described in Example 28 above (i.e., Mitsnobu reaction) using β-lactone 13j (80.0 mg, 0.315 mmol), triphenylphosphine (116 mg, 0.441 mmol), N-formylleucin (126 mg, 0.788 mmol), and DIAD (85 μL, 0.44 mmol) in 5 mL of THF. Purification by flash chromatography on SiO$_2$ (4:1, hexanes:EtOAc) gave a desired β-lactone 15p (85 mg, 68%).

$^1$H NMR (300 MHz, C$_6$D$_6$) δ 7.99 (s, 1H), 5.94 (d, J=8.1 Hz, 1H), 5.64-5.78 (m, 1H), 4.94-5.09 (m, 3H), 4.75 (dt, J=5.1, 9.6 Hz, 1H), 4.10 (dt, J=4.8, 8.1 Hz, 1H), 2.79 (dt, J=3.9, 7.5 Hz, 1H), 1.96-2.05 (m, 1H), 1.17-1.83 (m, 18H), 1.05 (d, J=6.0 Hz, 3H), 0.86-0.91 (m, 6H); $^{13}$C NMR (75 MHz, C$_6$D$_6$) δ 172.6, 170.8, 161.3, 137.9, 116.0, 74.8, 72.2, 57.6, 50.3, 41.5, 39.2, 33.9, 32.2, 30.0, 29.7, 28.1, 27.3, 25.4, 23.35, 23.27, 21.9, 14.6; LRMS (ESI) Calcd for C$_{22}$H$_{37}$NO$_5$ [M+Li] 402, Found 402.

EXAMPLE 44

Synthesis of (S)-2-Formylamino-3-phenyl-propionic Acid 1-((2S,3S,4S)-3-hexyl-4-oxo-oxetan-2-ylmethyl)-pent-4-enyl Ester (15q)

The title compound was synthesized according to the reaction scheme shown below.

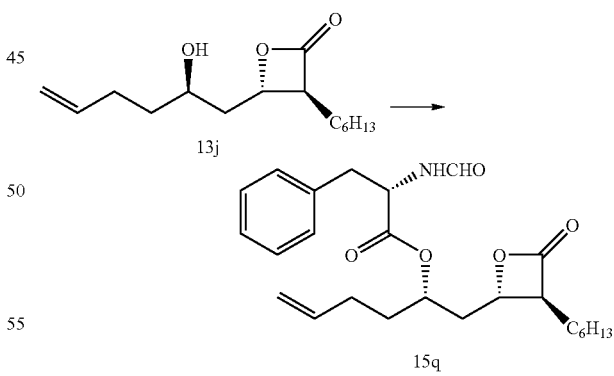

Prepared according to representative procedure described in Example 28 above (i.e., Mitsnobu reaction) using β-lactone 13j (40.0 mg, 0.157 mmol), triphenylphosphine (57.6 mg, 0.220 mmol), N-formyl-L-phenylalanine (70.0 mg, 0.362 mmol), and DIAD (43 μL, 0.22 mmol) in 3 mL of THF. Purification by flash chromatography on SiO$_2$ (4:1, hexanes: EtOAc) gave a desired β-lactone 15q (31 mg, 46%).

$^1$H NMR (300 MHz, C$_6$D6) δ 7.56 (s, 1H), 6.94-7.12 (m, 5H), 5.60-5.75 (m, 1H), 4.82-5.06 (m, 4H), 3.90-3.92 (m,

1H), 2.99 (dd, J=6.3, 14.4 Hz, 1H), 2.82 (dd, J=6.9, 14.4 Hz, 1H), 2.67 (dt, J=3.9, 7.5 Hz, 1H), 1.91 (q, J=6.9 Hz, 1H), 1.22-1.68 (m, 16H), 0.89 (t, J=6.9 Hz, 3H); $^{13}$C NMR (125 MHz, CDCl$_3$) δ 170.9 (2), 160.7, 137.1, 135.7, 129.4, 128.9, 127.6, 115.9, 74.6, 72.6, 57.3, 52.3, 38.9, 38.0, 33.2, 31.7, 29.5, 29.2, 27.8, 26.9, 22.7, 14.3.

EXAMPLE 45

Synthesis of (S)-2-Formylamino-4-methyl-pentanoic Acid 1-((2S,3S,4S)-3-octyl-4-oxo-oxetan-2-ylmethyl)-decyl Ester (15r)

The title compound was synthesized according to the reaction scheme shown below.

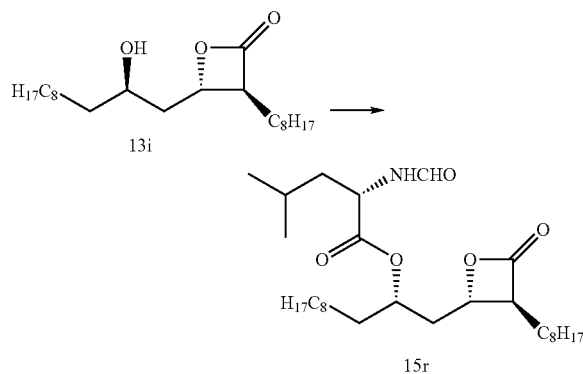

Prepared according to representative procedure described in Example 28 above (i.e., Mitsnobu reaction) using β-lactone 13i (6.0 mg, 0.017 mmol), triphenylphosphine (14.7 mg, 0.056 mmol), N-formyl-L-leucine (9.4 mg, 0.058 mmol), and DIAD (9.8 μL) in 0.5 mL of THF. Purification by flash chromatography on SiO$_2$ (0.4:1:3 THF/CHCl$_3$/hexane) gave a desired β-lactone 15r (6.2 mg, 74%).

IR (thin film) 2926, 2857, 1823, 1738, 1678 cm$^{-1}$; $^1$H NMR (300 MHz, CDCl$_3$) δ 8.23 (s, 1H), δ 5.92 (d, J=8.7 Hz, 1H), δ 5.10-4.98 (m, 1H), δ 4.70 (td, J=8.4, 4.8, 1H), δ 4.23 (ddd, J=8.4, 4.2, 3.9 Hz, 1H), δ 3.28 (td, J=7.2, 3.9 Hz, 1H), δ 2.24-1.96 (m, 2H), δ 1.85-1.53 (m, 5H), δ 1.27 (br. s., 26H), δ 0.98 (dd, J=6.3, 1.5 Hz, 6H), δ 0.89 (t, J=6.6 Hz, 3H); $^{13}$C NMR (1 d$_1$) (75 MHz, CDCl$_3$) δ 172.2, 171.0, 160.8, 75.0, 73.0, 57.3, 49.9, 41.8, 38.9, 34.3, 32.1, 32.0, 29.93, 29.71, 29.65, 29.56, 29.51, 29.49, 29.40, 27.8, 27.0, 25.3, 25.1, 23.1, 22.89, 22.86 22.0, 14.3; HRMS (ESI$^+$) Calcd for C$_{29}$H$_{53}$NO$_5$ [M+Li]: 502.4084. Found: 502.4080.

EXAMPLE 46

Synthesis of (S)-2-Formylamino-4-methyl-pentanoic Acid 1-((2S3R,4R)-3-hexyl-4-oxo-oxetan-2-ylmethyl)-tetradecyl Ester (16a)

The title compound was synthesized according to the reaction scheme shown below.

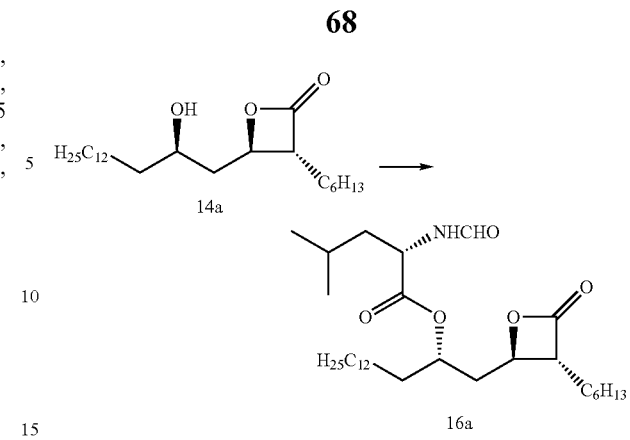

Prepared according to representative procedure described in Example 28 above (i.e., Mitsnobu reaction) using β-lactone 14a (20.0 mg, 0.0523 mmol), triphenylphosphine (44.4 mg, 0.169 mmol), N-formylluecin (31.6 mg, 0.197 mmol), DIAD (33 μL, 0.17 mmol) in 1 mL of THF. Purification by flash chromatography on SiO$_2$ (4:1, hexanes:EtOAc) gave a desired β-lactone 16a (10 mg, 17%).

$^1$H NMR (300 MHz, C$_6$D$_6$) δ 7.80 (s, 1H), 5.05-5.13 (m, 2H), 4.79 (dt, J=4.2, 8.7 Hz, 1H), 4.05 (quint, J=4.5 Hz, 1H), 2.81 (ddd, J=4.2, 4.9, 11.1 Hz, 1H), 1.12-1.71 (m, 39H), 0.83-0.92 (m, 12H); $^{13}$C NMR (75 MHz, C$_6$D$_6$) δ 172.6, 170.4, 160.7, 74.2, 72.6, 57.2, 50.1, 41.9, 39.4, 34.9, 32.7, 32.2, 30.54 (2), 30.52, 30.5, 30.4, 30.3, 30.2, 30.1, 29.7, 28.2, 27.4, 25.8, 25.3, 23.5, 23.31, 23.27, 22.0, 14.7, 14.6.

EXAMPLE 47

Synthesis of (S)-2-Formylamino-4-methyl-pentanoic Acid 1-((2S,3R,4R)-3-methyl-4-oxo-oxetan-2-ylmethyl)-dodecyl Ester (16b)

The title compound was synthesized according to the reaction scheme shown below.

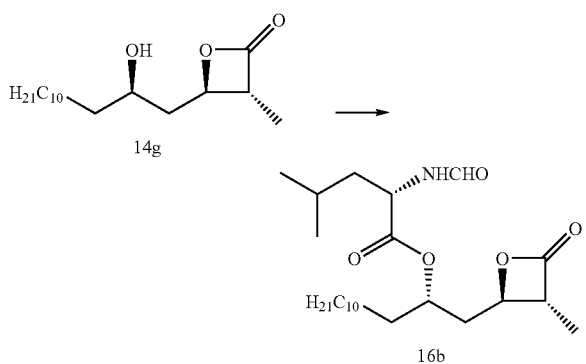

$^1$H NMR minor diastereomer (16b) (300 MHz, CDCl$_3$) δ 8.23 (s, 1H), δ 5.92 (d, J=8.7 Hz, 1H), δ 5.08-4.98 (m, 1H), δ 4.71 (td, J=8.4, 4.8, 1H), δ 4.27-4.19 (m, 1H), δ 3.29 (qd, J=7.5, 3.9 Hz, 1H), δ 2.12-2.05 (m, 2H), δ 1.75-1.50 (m, 5H), δ 1.41 (d, J=7.5 Hz, 3H), δ 1.26 (br. s., 18H), δ 0.98 (dd, J=6.3, 2.4 Hz, 6H), δ 0.89 (t, J=6.6 Hz, 3H); HRMS (ESI$^+$) Calcd for C$_{24}$H$_{43}$NO$_5$ [M+Li] 432.3301. Found: 432.3309.

EXAMPLE 48

Synthesis of (R)-1-((2S,3S)-3-ethyl-4-oxooxetan-2-yl)tridecan-2-yl 2-methanamidoethanoate (17a)

Representative Procedure for the Introduction of Amino Ester Side Chain Via Acylation The title compound was synthesized according to the reaction scheme shown below.

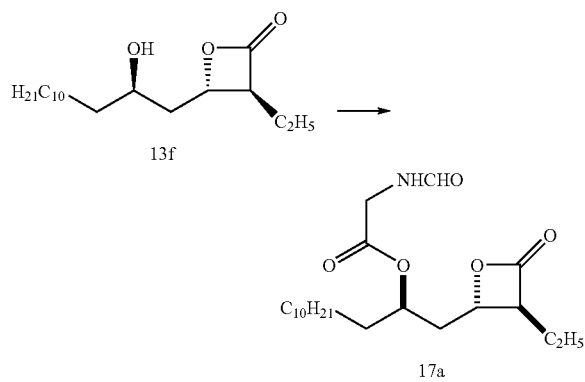

To a solution of hydroxy β-lactone 13f (11.0 mg, 0.0369 mmol), 1-ethyl-3-(3-dimethylaminopropyl)carbodiimide (9.20 mg, 0.048 mmol), 4-dimethylaminopyridine (5.45 mg, 0.044 mmol), 0.5 mL of xylene were added and the mixture was azeotroped in vacuo for 1.0 h. The residue was then dissolved in $CH_2Cl_2$ (1 mL) and N-formyl glycine (5.71 mg, 0.055 mmol) was then added. The clear reaction mixture turned orange-red. After twelve hours the mixture was extracted with water (3×1 mL) and dichloromethane. The organic phase then dried over $Na_2SO_4$, filtered and concentrated in vacuo. The residue was purified by chromatography ($SiO_2$, 20% EtOAc:hexanes) to afford β-lactone 17a (17.4 mg, 99%).

$R_f$=0.22 (50% EtOAc/hexanes); $[\alpha]^{22}{}_D$=−9.4 (c 0.4, $CHCl_3$); IR (thin film) 2926, 2855, 1823, 1738, 1651; $^1$H NMR (500 MHz, $CDCl_3$) δ 8.25 (br s, 1H), 6.22 (br s, 1H), 5.05-5.09 (m, 1H), 4.30-4.27 (m, 1H), 4.08 (d, J=5.5 Hz, 2H), 3.21 (dq, J=1.0, 4.5 Hz, 1H), 2.05-2.09 (m, 2H), 1.75-1.87 (m, 2H), 1.59-1.68 (m, 2H), 1.25-1.33 (m, 19H), 1.04 (app t, J=7.0 Hz, 3H), 0.88 (app t, J=6.5 Hz, 3H); $^{13}$C (125 MHz, $CDCl_3$) δ 171.0, 169.4, 161.3, 74.1, 73.2, 58.3, 40.4, 39.1, 34.5, 32.2, 30.0 (2), 29.9, 29.8, 29.7, 29.6, 25.4, 23.0, 21.2 (2), 14.5, 11.4; LRMS (ESI) Calcd for $C_{22}H_{38}O_5N$ [M+Li] 404.0, Found 401.29.

EXAMPLE 49

Synthesis of (R)-1-((2S,3S)-3-butyl-4-oxooxetan-2-yl)tridecan-2-yl 2-methanamidoethanoate (17b)

The title compound was synthesized according to the reaction scheme shown below.

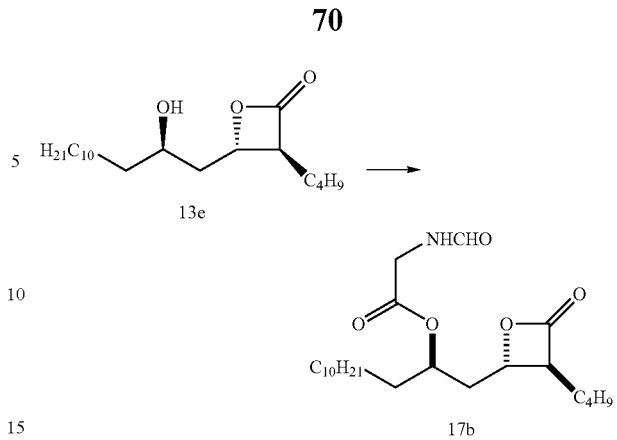

Prepared according to representative procedure described in Example 48 above (i.e., acylation). Hydroxy β-lactone 13e (8.5 mg, 0.026 mmol), 1-ethyl-3-(3-dimethylaminopropyl)carbodiimide (6.5 mg, 0.034 mmol), 4-dimethylaminopyridine (3.8 mg, 0.031 mmol), 0.5 mL of xylene were added and the mixture was azeotroped in vacuo for 1.0 h. After twelve hours the mixture was then dissolved in $CH_2Cl_2$ (1.5 mL) and the N-formyl glycine (4.0 mg, 0.039 mmol) was added. The resulting mixture was purified twice by chromatography ($SiO_2$, 40% EtOAc:hexanes) to afford β-lactone 17b (7.4 mg, 69%).

$R_f$=0.24 (40% EtOAc/hexanes); $[\alpha]^{22}{}_D$=−19.5 (c 0.8, $CHCl_3$); IR (thin film) 3386, 2926, 2855, 1825, 1745, 1681, 1519 cm$^{-1}$; $^1$H NMR (500 MHz, $CDCl_3$) δ 8.27 (br s, 1H), 6.09 (br s 1H), 5.09 (app quint, J=6.5 Hz, 1H), 4.26-4.30 (m, 1H), 4.13 (dd, J=1.0, 7.0 Hz, 1H), 4.10 (d, J=5.0 Hz, 2H), 3.22-3.26 (m, 1H), 2.07 (app t, J=6.5 Hz, 1H), 2.05 (d, J=1.00 Hz, 1H), 1.55-1.87 (m, 7H), 1.26-1.38 (m, 20H), 0.93 (app t, J=7.5 Hz, 2H), 0.89 (app t, J=7.5 Hz, 2H); $^{13}$C (125 MHz, $CDCl_3$) δ 171.0, 169.3, 161.145, 74.5, 73.1, 56.9, 40.3, 39.0, 34.4, 32.1, 29.84, 29.83, 29.75, 29.67, 29.7, 29.53 29.2, 27.6, 25.3, 22.9, 22.6, 14.4, 14.0; LRMS (ESI) Calcd for $C_{23}H_{41}NO_5$ [M+Li] 418.58, Found 418.33.

EXAMPLE 50

Synthesis of (2R,3S,4S)-Formylamino-acetic Acid 1-(3-hexyl-4-oxo-oxetan-2-ylmethyl)-dodecyl Ester (17c)

The title compound was synthesized according to the reaction scheme shown below.

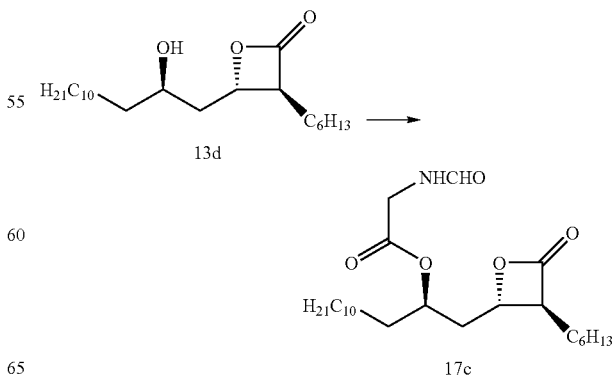

Prepared according to representative procedure described in Example 48 above (i.e., acylation) using β-lactone 13d (15.0 mg, 0.0423 mmol), N-formylglycin (4.8 mg, 0.047 mmol), 1-ethyl-3-(3-dimethylaminopropyl)carbodiimide (10.5 mg, 0.0550 mmol), and 4-dimethylaminopyridine (5.2 mg, 0.042 mmol) in 1 mL of $CH_2Cl_2$. Purification by flash chromatography on $SiO_2$ (4:1, hexanes:EtOAc) gave a desired β-lactone 17c (18 mg, 97%).

$^1$H NMR (500 MHz, $CDCl_3$) δ 8.28 (s, 1H), 6.15 (br, 1H), 5.06-5.11 (m, 1H), 4.27-4.30 (m, 1H), 4.03-4.14 (m, 2H), 3.22-3.26 (m, 1H), 2.07 (t, J=3.9 Hz, 2H), 1.26-1.85 (m, 30H), 0.87-0.91 (m, 6H); $^{13}$C NMR (125 MHz, $CDCl_3$) δ 170.9, 169.3, 161.1, 74.4, 73.0, 56.9, 40.3, 39.0, 34.4, 32.1, 31.7, 29.8 (2), 29.7, 29.6, 29.54, 29.52, 29.1, 27.9, 27.0, 25.3, 22.9, 22.7, 14.3, 14.2; LRMS (ESI) Calcd for $C_{25}H_{45}NO_5$ [M+H] 440, Found 440.

EXAMPLE 51

Synthesis of (R)-1-((2S,3S)-3-hexyl-4-oxooxetan-2-yl)propan-2-yl-2-methanamidoethanoate (17d)

The title compound was synthesized according to the reaction scheme shown below.

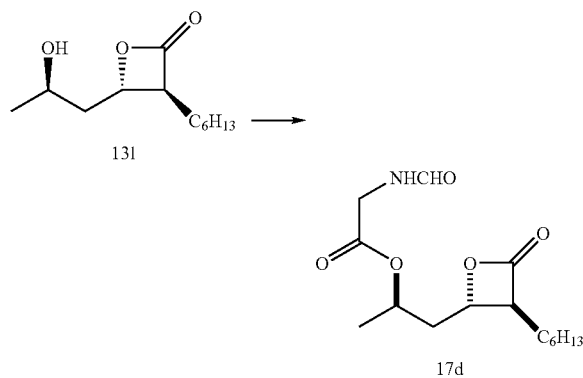

Prepared according to representative procedure described in Example 48 above (i.e., acylation) using hydroxy β-lactone 13l (10.9 mg, 0.051 mmol), 1-ethyl-3-(3-dimethylaminopropyl)carbodiimide (12.6 mg, 0.066 mmol), 4-dimethylaminopyridine (7.5 mg, 0.061 mmol), 0.5 mL of xylene azeotroped in vacuo for 1.0 h. After twelve hours the residue was then dissolved in $CH_2Cl_2$ (2 mL) and the N-formyl glycine (7.9 mg, 0.077 mmol) was added. The resulting mixture was purified by chromatography ($SiO_2$, gradient 10-40% EtOAc: hexanes) to afford β-lactone 17d (7.9 mg, 52%).

$R_f$=0.11 (40% EtOAc/hexanes); $[\alpha]^{22}_D$=−30.9 (c 0.60, $CHCl_3$); IR (thin film) 3376, 2931, 1820, 1747, 1685 cm$^{-1}$; $^1$H NMR (500 MHz, $CDCl_3$) δ 8.23 (br s, 1H), 6.07 (brs, 1H), 5.10-5.17 (m, 1H), 4.30 (app. quint, J=4.0 Hz, 1H), 4.09 (dd, J=0.5, 5.0 Hz, 1H), 3.25 (ddd, J=1.5, 4.0, 6.5 Hz, 1H), 2.10-2.15 (m, 1H), 2.01-2.06 (m, 1H), 1.80-1.87 (m, 1H), 1.70-1.77 (m, 11H), 1.30-1.47 (m, 14H), 0.89 (app. t, J=3.5 Hz, 3H); $^{13}$C (125 MHz, $CDCl_3$) δ 170.9, 169.1, 161.2, 74.3, 59.8, 57.0, 40.8, 40.3, 31.7, 29.1, 27.9, 27.0 22.7, 20.5, 14.2; LRMS (ESI) Calcd for $C_{16}H_{27}NO_5$ [M+Li] 306.39, Found 306.20.

EXAMPLE 52

Synthesis of (S)-1-((2S,3S)-3-hexyl-4-oxooxetan-2-yl)-3-(tosyloxy)propan-2-yl 2-methanamido-ethanoate (17e)

The title compound was synthesized according to the reaction scheme shown below.

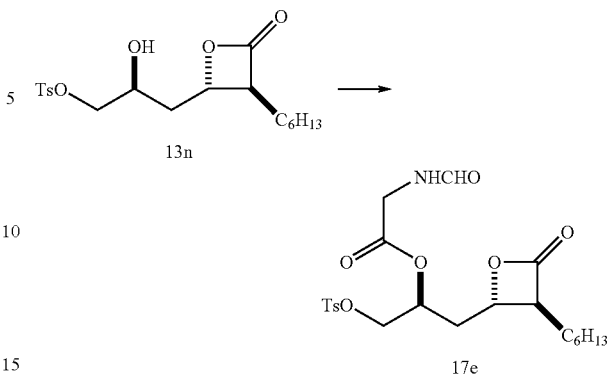

Prepared according to representative procedure described in Example 48 above (i.e., acylation). To a solution of hydroxy β-lactone 13n (13.0 mg, 0.034 mmol), 1-ethyl-3-(3-dimethylaminopropyl)carbodiimide (8.50 mg, 0.044 mmol), 4-dimethylaminopyridine (5.0 mg, 0.041 mmol), 0.5 mL of xylene were added and the mixture was azeotroped in vacuo for 1 h. The mixture was then dissolved in $CH_2Cl_2$ (2 mL) and the N-formyl glycine (5.26 mg, 0.051 mmol) was added. The resulting mixture was purified by chromatography ($SiO_2$, 20% EtOAc:hexanes) to afford β-lactone 17e (9.2 mg, 58%).

$R_f$=0.22 (40% EtOAc/hexanes); $[\alpha]^D_{22}$=−6.5 (c 0.4, $CHCl_3$); IR (thin film) 2955, 2925, 2855, 1738, 1607, 1516, 1466; $^1$H NMR (125 MHz, $CDCl_3$) δ 8.27 (br s, 1H), 7.77 (d, J=7 Hz, 2H), 7.38 (d, J=8 Hz, 2H), 6.07 (br s, 1H), 5.14-5.19 (m, 1H), 4.29 (app t, J=12 Hz, 1H), 4.05-4.16 (m, 4H), 3.23-3.27 (m, 1H), 2.47 (s, 3H), 2.26-2.31 (m, 2H), 1.99-2.05 (m, 2H), 1.72-1.86 (m, 3H); $^{13}$C NMR (125 MHz, $CDCl_3$) δ170.3, 168.3, 161.2, 145.8, 132.7, 130.3 (2), 128.12 (2), 73.7, 69.7, 57.2, 40.1, 35.6, 31.6, 29.1, 27.8, 27.0, 22.7, 21.9, 14.3; LRMS (ESI) Calcd for $C_{22}H_{31}NO_8S$ 476, Found 476.

EXAMPLE 53

Synthesis of (R)-1-((2S,3S)-3-hexyl-4-oxooxetan-2-yl)hex-5-en-2-yl 2-methanamidoethanoate (17f)

The title compound was synthesized according to the reaction scheme shown below.

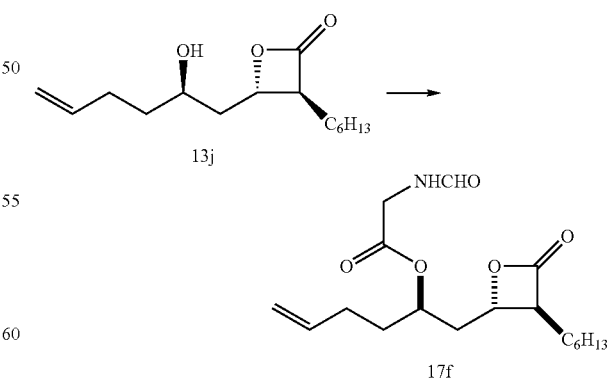

Prepared according to representative procedure described in Example 48 above (i.e., acylation) using hydroxy β-lactone 13j (15.0 mg, 0.059 mmol), 1-ethyl-3-(3-dimethylaminopropyl)carbodiimide (14.8 mg, 0.077 mmol), 4-dimethylaminopyridine (8.71 mg, 0.071 mmol), 0.5 mL of xylene were azeotroped in vacuo for 1.0 h. After twelve hours the residue was then dissolved in $CH_2Cl_2$ (1.5 mL) and N-formyl glycine (9.12 mg, 0.089 mmol) was added. The resulting mixture was purified twice by chromatography ($SiO_2$, gradient 10-40% EtOAc:hexanes) to afford β-lactone 17f (10.8 mg, 55%).

$R_f$=0.33 (40% EtOAc/hexanes); $[α]^{22}_D$=−5.1 (c 1.8, $CHCl_3$); IR (thin film) 3418, 2925, 2854, 1819, 1740, 1667 $cm^{-1}$; $^1H$ NMR (500 MHz, $CDCl_3$) δ 8.27 (br s, 1H), 6.10 (br s, 1H), 5.73-5.81 (m, 1H), 5.07-5.14 (m, 1H), 5.02 (dt, J=1.5, 10.5 Hz, 2H), 4.27-4.30 (m, 1H), 4.09 (dt, J=0.5, 5.0 Hz, 2H), 3.21-3.25 (m, 1H), 2.09 (app. t, J=7.0 Hz, 4H), 1.64-1.85 (m, 4H), 1.24-1.45 (m, 8H), 0.89 (app. t, J=7.0 Hz, 3H); $^{13}C$ (125 MHz, $CDCl_3$) δ 170.9, 169.3, 161.1, 137.0, 116.0, 74.4, 72.5, 57.0, 40.3, 39.1, 33.5, 31.7, 29.5, 29.2, 27.9, 27.0, 22.7, 14.3; LRMS (ESI) Calcd for $C_{18}H_{29}NO_5$ [M+H] 340.43, Found 340.19.

EXAMPLE 54

Synthesis of (R)-1-((2S,3S)-3-hexyl-4-oxooxetan-2-yl)hept-5-en-2-yl 2-methanamidoethanoate (17g)

The title compound was synthesized according to the reaction scheme shown below.

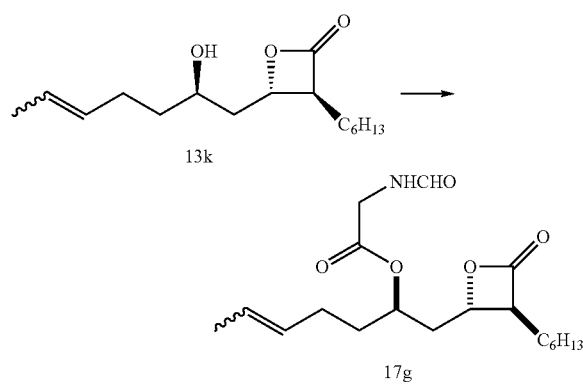

Prepared according to representative procedure described in Example 48 above (i.e., acylation) using hydroxy β-lactone 13k (15.6 mg, 0.058 mmol), 1-ethyl-3-(3-dimethylaminopropyl)carbodiimide (14.4 mg, 0.075 mmol), 4-dimethylaminopyridine (8.7 mg, 0.070 mmol), 0.5 mL of xylene were azeotroped in vacuo for 1.0 h. The residue was then dissolved in $CH_2Cl_2$ (1.5 mL) and N-formyl glycine (9.0 mg, 0.087 mmol) was added. After twelve hours resulting mixture was purified by chromatography ($SiO_2$, gradient 10-40% EtOAc: hexanes) to afford β-lactone 17g (11.7 mg, 57%).

$R_f$=0.38 (40% EtOAc/hexanes); $[α]^{22}_D$=−22 (c 1.1, $CHCl_3$); IR (thin film) 2926, 2855, 1823, 1712 $cm^{-1}$; $^1H$ NMR (500 MHz, $CDCl_3$) δ 8.27 (br s, 1H), 6.11 (br 5, 1H), 5.42-5.48 (m, 1H), 5.34-5.39 (m, 1H), 5.10 (app quint, J=5.0 Hz, 1H), 4.26-4.29 (m, 1H), 4.09 (d, J=5.5 Hz, 2H), 3.22-3.60 (m, 1H), 1.99-2.10 (m, 4H), 1.64-1.85 (m, 4H), 1.25-1.45 (m, 8H), 0.89 (app. t, J=9.0 Hz, 6H); $^{13}C$ NMR (125 MHz, $CDCl_3$) δ 170.9, 169.3, 161.1, 129.5, 126.6, 74.4, 72.5, 56.9, 40.3, 39.0, 34.2, 31.7, 29.2, 28.4, 27.0, 22.7, 18.1, 14.3; LRMS (ESI) Calcd for $C_{19}H_{31}NO_5$ [M+Li] 360.22, Found 360.24.

EXAMPLE 55

Synthesis of 2-Formylamino-3-methyl-butyric Acid (2S,2R,3S,4S)-1-(3-hexyl-4-oxo-oxetan-2-ylmethyl)-hex-4-enyl Ester (17h)

The title compound was synthesized according to the reaction scheme shown below.

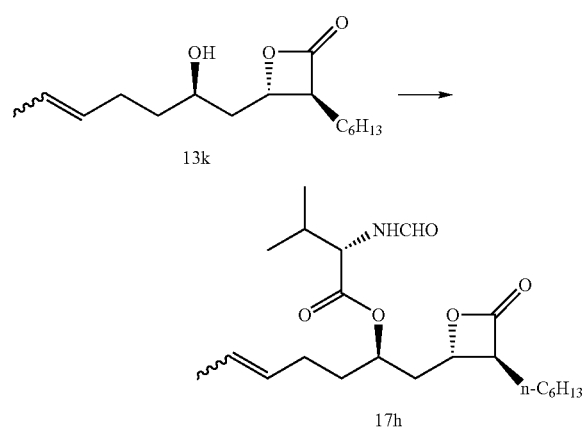

Prepared according to representative procedure described in Example 48 above (i.e., acylation) using β-lactone 13k (20.0 mg, 0.0745 mmol), N-formyl-L-valine (11.9 mg, 0.0820 mmol), 1-ethyl-3-(3-dimethylaminopropyl)carbodiimide (18.6 mg, 0.0969 mmol), and 4-dimethylaminopyridine (9.2 mg, 0.0745 mmol) in 1.5 mL of $CH_2Cl_2$. Purification by flash chromatography on $SiO_2$ (0.4:1:3 THF/$CHCl_3$/hexane) gave a desired β-lactone 17h.

E/Z-mixture, only major peaks are assigned. $^1H$ NMR (300 MHz, $CDCl_3$) δ 8.28 (s, 1H), 6.08 (br, 1H), 5.34-5.50 (m, 2H), 5.02-5.10 (m, 1H), 4.63-4.68 (m, 1H), 4.28 (dt, J=3.9, 8.1 Hz, 1H), 3.20-3.28 (m, 1H), 2.18-2.26 (m, 1H), 1.30-2.08 (m, 19H), 1.01 (d, J=6.9 Hz, 3H), 0.93 (d, J=6.9 Hz, 3H), 0.89 (t, J=6.9 Hz, 3H); $^{13}C$ NMR (75 MHz, $CDCl_3$) δ 171.3 (2), 161.1, 129.4, 126.6, 74.4, 72.3, 57.0, 55.9, 39.2, 34.3, 31.7, 31.4, 29.1, 28.3, 27.8, 27.0, 22.7, 19.4, 18.1, 17.6, 14.2.

EXAMPLE 56

Synthesis of (R)-1-((2S,3R)-3-hexyl-4-oxooxetan-2-yl)tridecan-2-yl 2-methanamidoethanoate (17i) (Representative Procedure for the Synthesis of cis-β-Lactones)

The title compound was synthesized according to the reaction scheme shown below, and the sequence of steps discussed below was followed.

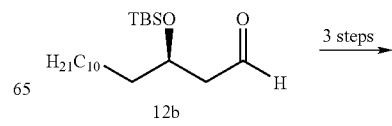

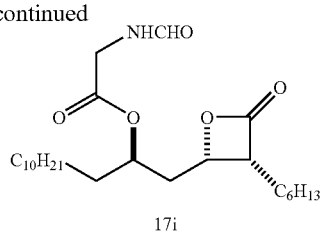

17i

The aldehyde 12b (0.189 g, 0.55 mmol) and the thiopyridyl ketene acetal 3c (0.21 g, 1.10 mmol) were dissolved in 4 mL of $CH_2Cl_2$ and cooled to −78° C. (dry ice/acetone bath). With stirring, 0.66 mL of a 1.0 M $SnCl_4$ solution (0.66 mL, 1.2 equiv) in $CH_2Cl_2$ was added via syringe pump over 2 h. After stirring for 10 h, the reaction was warmed to −50° C. and stirred for 6 more hours. The reaction was quenched with pH 7 buffer (10 mL) at −50° C.; and warmed to room temperature with vigorous stirring, then filtered through a small pad of Celite. The resulting clear solution was dried over $Na_2SO_4$, filtered and the volume of $CH_2Cl_2$ was adjusted to a final concentration of 0.15 M. $CuBr_2$ (0.26 g, 1.10 mmol) was added and the mixture was stirred for 2 h. The resulting suspension was filtered through Celite, washed with 10% aqueous $K_2CO_3$ (2×10 mL) solution and brine (2×20 mL). The organic phase was dried over $Na_2SO_4$, filtered, and concentrated in vacuo. The residue was purified by chromatography ($SiO_2$, 30% EtOAc in hexanes), affording a mixture of diastereoisomers (dr=3:1).

Desilylation procedure. To a solution of the diastereoisomeric mixture in 20 mL of dry $CH_3CN$ cooled at 0° C. was added 48% aqueous HF (0.43 mL). The reaction mixture was stirred at 0° C. for 2 hours and then warmed to room temperature. After 2 more hours, the reaction mixture was diluted with 15 mL of ether. The organic layer was separated, washed with a saturated solution of $NaHCO_3$, which was added slowly, (2×20 mL) and brine (2×20 mL). The residue was dried over $Na_2SO_4$, filtered and concentrated in vacuo. The mixture was purified by flash chromatography on $SiO_2$ (2-10% EtOAc in hexanes). The diastereoisomers were partially separated via MPLC on $SiO_2$ (10% EtOAc in hexanes). Only 12 mg of the major diastereoisomer (dr >19:1) was separated completely.

Acylation procedure. To a solution of the hydroxy β-lactone (12.0 mg, 0.032 mmol), 1-ethyl-3-(3-dimethylaminopropyl)carbodiimide (7.8 mg, 0.041 mmol), 4-dimethylamino-pyridine (54.7 mg, 0.038 mmol), 0.5 mL of xylene were added and the mixture was azeotroped in vacuo for 1 h. The residue was then dissolved in $CH_2Cl_2$ (2 mL) and N-formyl glycine (5.0 mg, 0.048 mmol) was added. After 12 h, the mixture was extracted with water (3×1 mL) and dichloromethane. The organic phase was then dried over $Na_2SO_4$, filtered and concentrated in vacuo. The residue was purified by chromatography ($SiO_2$, 20% EtOAc:hexanes) to afford β-lactone 17i (7.2 mg, 51%).

$R_f$=0.32 (40% EtOAc/hexanes); $[α]^{22}_D$=−8.8 (c 0.45, $CHCl_3$), IR (thin film) 2925, 2854, 1823, 1748, 1824, 1748 1654 $cm^{-1}$; $^1H$ NMR (500 MHz, $CDCl_3$) δ 8.27 (br s, 1H), 6.09 (br s, 1H), 5.11-5.15 (m, 1H), 4.58-4.67 (m, 1H), 4.12-4.13 (m, 2H), 3.67 (app. d, J=7.0 Hz, 1H), 1.90-2.05 (m, 2H), 1.70-1.80 (m, 8H), 1.20-1.40 (m, 25H), 0.99 (m, 7H); $^{13}C$ NMR (125 MHz, $CDCl_3$) δ 171.6, 169.3, 161.2, 73.1, 71.8, 53.2, 40.2, 34.9, 34.5, 32.1, 31.7, 29.9, 29.85 (2), 29.83, 29.77, 29.7, 29.57, 29.56, 29.2, 27.6, 25.3, 24.3, 22.9, 22.8, 14.4, 14.3; LRMS (ESI) Calcd for $C_{27}H_{49}NO_5$ [M+Li] 446.68, Found 446.35.

EXAMPLE 57

Synthesis of 2-Formylamino-3-phenyl-propionic Acid 1-(3-hexyl-4-oxo-oxetan-2-ylmethyl)-dodec-4-enyl Ester (21b) (Representative Procedure for Cross-Metathesis)

The title compound was synthesized according to the reaction scheme shown below.

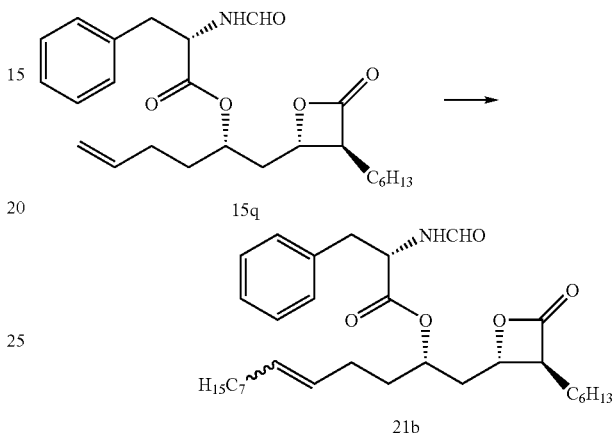

To a solution of β-lactone 15q (10 mg, 0.023 mmol) and n-nonene (20 mL, 0.12 mmol) in 0.2 mL of $CH_2Cl_2$, which was placed in a sealed tube, was added a solution of Grubb's catalyst (3.8 mg, 0.0047 mmol) in 0.1 mL of $CH_2Cl_2$ via syringe. The mixture was stirred at 45° C. for 24 h and concentrated under reduced pressure. The remained residue was directly purified by flash chromatography on $SiO_2$ (10:1, hexanes:EtOAc) to provide a desired β-lactone (5.5 mg, 45%) along with recovered β-lactone 21b (3.8 mg, 38%).

E/Z-mixture, only major peaks are assigned. $^1H$ NMR (300 MHz, $CDCl_3$) δ 8.20 (s, 1H), 7.20-7.30 (m, 5H), 6.02 (d, J=7.2 Hz, 1H), 5.30-5.50 (m, 2H), 5.00-5.08 (m, 1H), 4.94 (q, J=6.9 Hz, 1H), 4.17-4.23 (m, 1H), 3.13-3.21 (m, 4H), 1.30-2.12 (m, 27H), 0.89-0.93 (m, 6H); LRMS (ESI) Calcd for $C_{32}H_{49}NO_5$ [M+Li] 534, Found 534.

EXAMPLE 58

Synthesis of 2-Formylamino-4-methyl-pentanoic Acid 1-(3-hexyl-4-oxo-oxetan-2-ylmethyl)-dodec-4-enyl Ester (20a)

The title compound was synthesized according to the reaction scheme shown below.

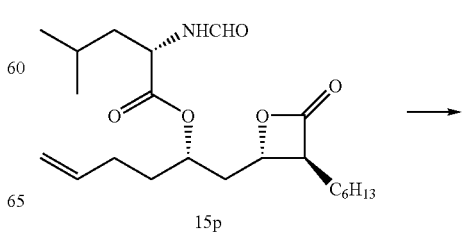

15p

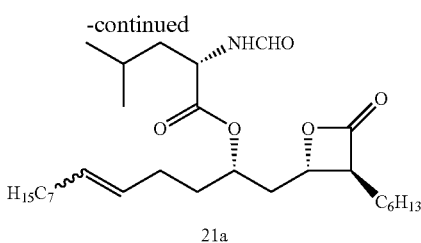

21a

Prepared according to the representative cross-metathesis described in Example 57 above, using β-lactone 15q (23.5 mg, 0.0594 mmol), Grubb's catalyst (4.9 mg, 0.00594 mmol) and n-nonene (51 mL, 0.297 mmol) in 0.3 mL of $CH_2Cl_2$. Purification by flash chromatography on $SiO_2$ (4:1, hexanes:EtOAc) gave a desired β-lactone 21a (Yield is not determined).

$^1$H NMR (500 MHz, $CDCl_3$) δ 8.23 (s, 1H), 5.90 (d, J=8.5 Hz, 1H), 5.31-5.47 (m, 2H), 5.04-5.08 (m, 1H), 4.70 (dt, J=4.0, 8.5 Hz, 1H), 4.30 (quint, J=4.5 Hz, 1H), 3.20-3.25 (m, 1H), 1.95-2.20 (m, 6H), 1.57-1.82 (m, 8H), 1.25-1.46 (m, 17H), 0.87-0.99 (m, 12H); LRMS (ESI) Calcd for $C_{29}H_{51}NO_5$ [M+Li] 500, Found 500.

EXAMPLE 59

Synthesis of 2-Formylamino-4-methyl-pentanoic Acid 5-(4-fluoro-phenyl)-1-(3-hexyl-4-oxo-oxetan-2-ylmethyl)-pent-4-enyl Ester (21c)

The title compound was synthesized according to the reaction scheme shown below.

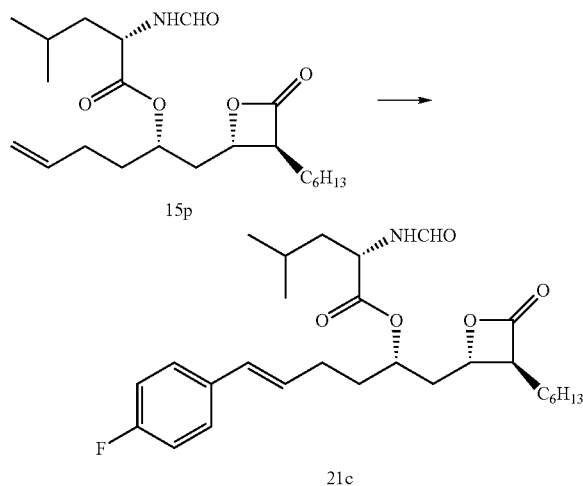

Prepared according to the representative cross-metathesis described in Example 57 above, using β-lactone 15q (15.0 mg, 0.0379 mmol), Grubb's catalyst (3.1 mg, 0.0038 mmol) and 4-fluorostyrene (18 mL, 0.15 mmol) in 0.3 mL of $CH_2Cl_2$. Purification by flash chromatography on $SiO_2$ (4:1, hexanes:EtOAc) gave a desired β-lactone 21c (Yield is not determined).

$^1$H NMR (300 MHz, $CDCl_3$) δ 8.15 (s, 1H), 7.30-7.34 (m, 2H), 6.98-7.04 (m, 2H), 6.40 (d, J=15.6 Hz, 1H), 6.10 (dt, J=6.6, 15.6 Hz, 1H), 5.90 (d, J=8.1 Hz, 1H), 5.10-5.20 (m, 1H), 4.72 (dt, J=5.1, 9.3 Hz, 1H), 4.30-4.36 (m, 1H), 3.22-3.29 (m, 1H), 1.25-2.70 (m, 19H), 0.89-1.01 (m, 9H); LRMS (ESI) Calcd for $C_{23}H_{40}FNO_5$ [M+Na] 512, Found 512.

EXAMPLE 60

Synthesis of (E,2R,3S,4S)-4-[6-(4-Bromo-phenyl)-2-hydroxy-hex-5-enyl]-3-hexyl-oxetan-2-one (20d) and 2-Formylamino-3-phenyl-propionic Acid 5-(4-bromo-phenyl)-1-(3-hexyl-4-oxo-oxetan-2-ylmethyl)-pent-4-enyl Ester (21d)

The title compound was synthesized according to the reaction scheme shown below, and the sequence of steps discusse below was followed.

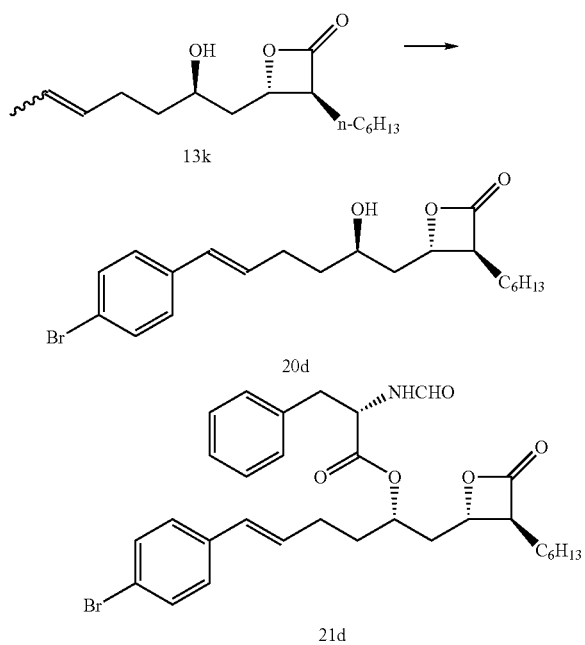

To a solution of 13k (30 mg, 0.11 mmol) and 4-bromostyrene (73 mL, 0.56 mmol) in 0.3 mL of $CH_2Cl_2$, which was placed in a sealed tube, was added a solution of Grubb's catalyst (13.8 mg, 0.017 mmol) in 0.2 mL of $CH_2Cl_2$ via syringe. The mixture was stirred at 40° C. for 48 h and concentrated under reduced pressure. The remained residue was purified by flash chromatography on $SiO_2$ (10:1, hexanes:EtOAc) to provide 20d (16 mg, 35%) as a white solid. IR (thin film) 1811 cm$^{-1}$; $^1$H NMR (500 MHz, $CDCl_3$) δ 7.42 (d, J=8.5 Hz, 2H), 7.21 (d, J=8.5 Hz, 2H), 6.38 (d, J=16 Hz, 2H), 5.22 (dt, J=7.0, 16 Hz, 1H), 4.51 (dt, J=4.5, 8.5 Hz, 1H), 3.87-3.94 (m, 1H), 3.28 (ddd, J=4.0, 7.0, 8.0 Hz, 1H), 2.28-2.42 (m, 2H), 1.67-1.98 (m, 7H), 1.26-1.48 (m, 8H), 0.89 (t, J=7.0 Hz, 3H); $^{13}$C NMR (125 MHz, $CDCl_3$) δ 171.7, 136.5, 131.8, 130.6, 129.8, 127.7, 121.0, 75.6, 68.3, 56.8, 42.1, 37.5, 31.7, 29.3, 29.2, 27.9, 27.0, 22.7, 14.3; LRMS (ESI) Calcd for $C_{21}H_{29}BrO_3$ [M+Li] 415, Found 415.

Next, the representative procedure described in Example 27 above (i.e., Mitsnobu reaction) was followed using β-lactone 20d (10.0 mg, 0.0244 mmol), triphenylphosphine (9.0 mg, 0.034 mmol), N-formyl-L-phenylalanine (9.4 mg, 0.049 mmol), DIAD (6.6 μL, 0.034 mmol) in 1 mL of THF. Purification by flash chromatography on $SiO_2$ (0.4:1:3, THF:$CHCl_3$:hexanes) gave a desired β-lactone 21d (yield ND) as a white solid.

$^1$H NMR (300 MHz, CDCl$_3$) δ 8.16 (s, 1H), 7.14-7.45 (m, 9H), 6.33 (d, J=15.6 Hz, 1H), 6.12 (dt, J=6.9, 15.6 Hz, 1H), 5.95 (d, J=7.2 Hz, 1H), 5.04-5.12 (m, 1H), 4.91 (q, J=7.5 Hz, 1H), 4.20 (quint, J=4.8 Hz, 1H), 3.05-3.24 (m, 3H), 2.20 (q, J=7.2 Hz, 2H), 2.08 (q, J=7.8 Hz, 1H), 1.94 (dt, J=4.2, 15.3 Hz, 1H), 1.69-1.88 (m, 4H), 1.24-1.36 (m, 8H), 0.89 (t, J=6.3 Hz, 3H); LRMS (ESI) Calcd for C$_{31}$H$_{38}$BrNO$_5$ [M+H] 584, Found 584.

EXAMPLE 61

Synthesis of 2-Formylamino-4-methyl-pentanoic Acid 6-[2-(2-benzyloxycarbonylmethoxy-ethoxy)-ethoxy]-1-(3-hexyl-4-oxo-oxetan-2-ylmethyl)-hex-4-enyl ester (21f)

The title compound was synthesized according to the reaction scheme shown below.

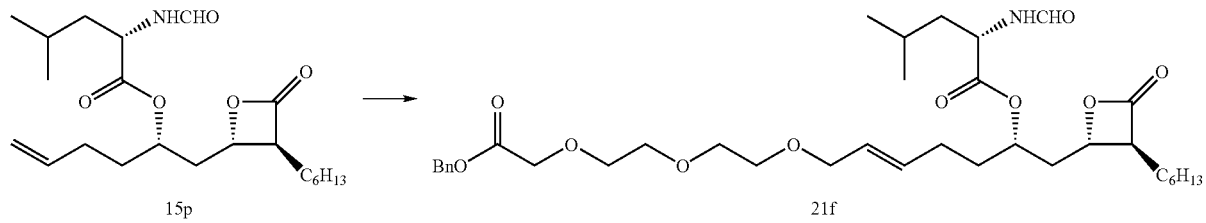

Prepared according to the representative cross-metathesis described in Example 57 above, using β-lactone 15p (30.0 mg, 0.0758 mmol), 2$^{nd}$ Grubb's catalyst (13 mg, 0.0152 mmol) and benzylester (128 mg, 0.435 mmol) in 3 mL of CH$_2$Cl$_2$. Purification by flash chromatography on SiO$_2$ (2:1: 2, hexanes:CH$_2$Cl$_2$:EtOAc) gave a desired β-lactone 21f (yield is not determined; based on $^1$H NMR, this compound is contaminated by-product (dimer of benzyl ester)). LRMS (ESI) Calcd for C$_{36}$H$_{55}$NO$_{10}$ [M+Li] 668, Found 668.

EXAMPLE 62

Synthesis of (2R,3S,4S)-3-Hexyl-4-(2-hydroxy-tridec-5-enyl)-oxetan-2-one (9)

The title compound was synthesized according to the reaction scheme shown below.

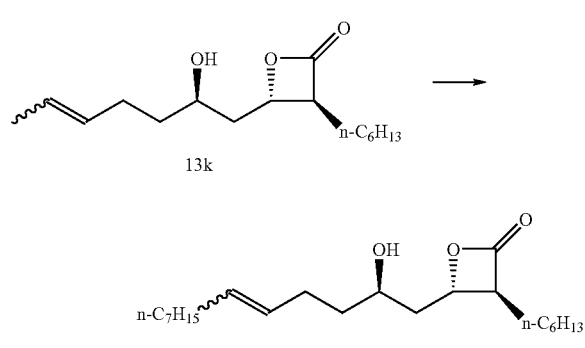

Prepared according to the representative cross-metathesis described in Example 57 above, using β-lactone 13k (35.0 mg, 0.130 mmol), Grubb's catalyst (13.8 mg, 0.0168 mmol) and n-nonene (73 mL, 0.56 mmol) in 0.5 mL of CH$_2$Cl$_2$. Purification by flash chromatography on SiO$_2$ (10:1, hexanes: EtOAc) gave 20a (9.2 mg, 20%) as a white solid along with recovered 13k (28 mg, 80%).

E/Z-mixture, only major peaks are assigned. IR (thin film) 3466, 1820 cm$^{-1}$; $^1$H NMR (500 MHz, CDCl$_3$) δ 5.35-5.52 (m, 2H), 4.50 (dt, J=4.0, 8.5 Hz, 1H), 3.82-3.88 (m, 1H), 3.25-3.29 (m, 1H), 1.70-2.22 (m, 1H), 1.24-1.58 (m, 20H), 0.89 (t, J=7.0 Hz, 6H); $^{13}$C NMR (75 MHz, CDCl$_3$) δ 171.8, 132.1, 129.3, 75.7, 68.5, 56.8, 42.1, 37.8, 32.8, 32.1, 31.7, 29.7, 29.38, 29.36, 29.2, 29.1, 27.9, 27.0, 22.9, 22.7, 14.3, 14.2; LRMS (ESI) Calcd for C$_{22}$H$_{42}$O$_3$ [M+Li] 359, Found 359.

EXAMPLE 63

Synthesis of (S)—((S)-1-((2S,3S)-3-hexyl-4-oxooxetan-2-yl)heptan-2-yl) 2-methanamido-3-methylbutanoate (23a) (Representative Procedure for the Hydrogenation of Unsaturated β-Lactones)

The title compound was synthesized according to the reaction scheme shown below.

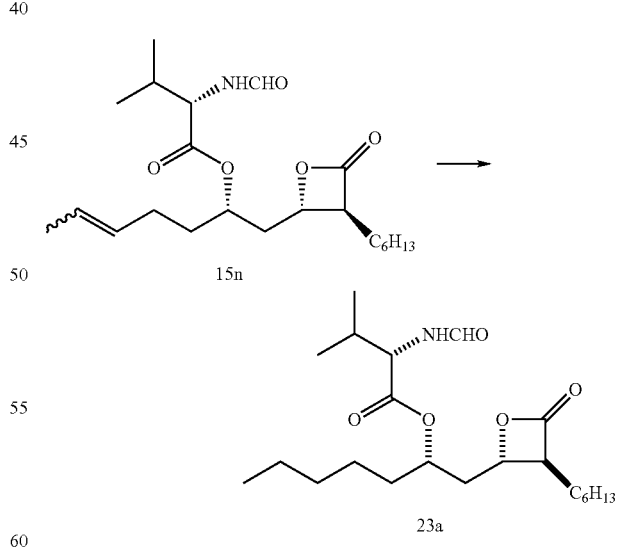

E/Z-mixture of β-lactone 15n (21 mg, 0.053 mmol) and 5 wt % palladium on carbon (15 mg) in 4 mL of CH$_2$Cl$_2$ was stirred at ambient temperature for 12 h under H$_2$ atmosphere. The reaction mixture was then filtered through a pad of Celite to remove the catalyst and washed with CH$_2$Cl$_2$ (5×2 mL). The combined organic filtrate was concentrated and purified by chromatography (SiO$_2$, 40% EtOAc:hexanes) to give the desired β-lactone 23a (20 mg, 95%).

R$_f$=0.24 (30% EtOAc/hexanes); [α]$^{22}_D$=−2.1 (c 0.3, CHCl$_3$), IR (thin film) 2958, 2923, 2851, 1822, 1728, 1684 cm$^{-1}$; $^1$H NMR (500 MHz, CDCl$_3$) δ 8.28 (br s, 1H), 6.00-6.08 (m, 1H), 5.08-5.17 (m, 1H), 4.64 (ddd, J=0.5, 5.0, 10.0 Hz, 1H), 4.27-3.32 (m, 1H), 3.21-3.25 (m, 1H), 2.16-2.25 (m, 4H), 2.03 (dt, J=0.5, 4.5 Hz, 1H), 2.00 (dt, J=0.5, 4.5 Hz, 1H), 1.55-1.81 (m, 5H), 1.25-1.34 (m, 8H), 1.00 (d, J=7.0 Hz, 4H), 0.92 (dd, J=1.5, 7.0 Hz, 4H), 0.89 (app. t, J=7.0, 6H); $^{13}$C NMR (125 MHz, CDCl$_3$) δ 171.2, 170.9, 161.0, 74.9, 73.1, 57.3, 56.1, 38.9, 34.1, 31.7, 31.3, 29.9(2), 29.2, 27.9, 26.9, 25.0, 22.7, 19.5, 17.6, 14.3, 14.2; LRMS (ESI) Calcd for C$_{22}$H$_{39}$NO$_5$ [M+Li] 404.55, Found 404.32.

EXAMPLE 64

Synthesis of (R)-1-((2S,3S)-3-hexyl-4-oxooxetan-2-yl)hexan-2-yl 2-methanamidoethanoate (23b)

The title compound was synthesized according to the reaction scheme shown below.

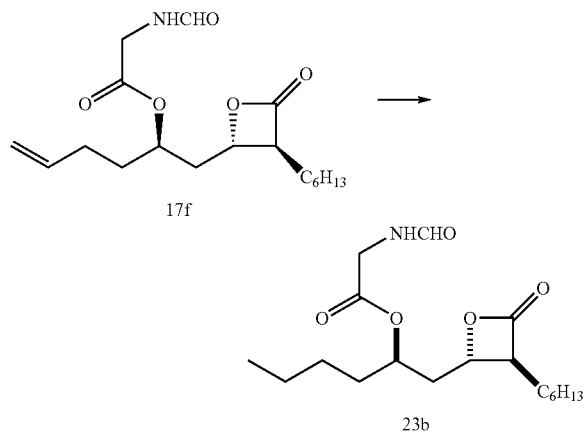

Prepared according to representative procedure described in Example 63, above. β-lactone 17f (6.2 mg, 0.018 mmol) and 5 wt % palladium on carbon (5 mg) in 2 mL of CH$_2$Cl$_2$ was stirred at ambient temperature for 12 h under H$_2$ atmosphere. Filtration and chromatography (SiO$_2$, 40% EtOAc:hexanes) gave the desired β-lactone 23b (5.8 mg, 95.1%).

R$_f$=0.24 (40% EtOAc:hexanes); [α]$^{22}_D$=−28.9 (c 0.8, CHCl$_3$); IR (thin film) 2927, 2858, 1819, 1745, 1675 cm$^{-1}$; $^1$H NMR (500 MHz, CDCl$_3$) δ 8.27 (br s, 1H), 6.09 (br s, 1H), 5.06-5.12 (m, 1H), 4.27-4.30 (m, 1H), 4.10 (dd, J=2.0, 5.0 Hz, 2H), 3.22-3.27 (m, 1H), 2.07 (dt, J=1.5, 6.5 Hz, 2H), 1.53-1.87 (m, 8H), 1.23-1.47 (m, 10H), 0.90 (dd, J=7.0, 15.0 Hz, 4H), $^{13}$C NMR (125 MHz, CDCl$_3$) δ 171.0, 169.3, 161.2, 74.5, 73.0, 56.9, 40.3, 39.0, 34.1, 31.7, 29.2, 27.9, 27.4, 27.0, 22.7, 22.6, 14.3, 14.1. LRMS (ESI) Calcd for C$_{18}$H$_{31}$NO$_5$ [M+Li]: 348.44, Found 348.23.

EXAMPLE 65

Synthesis of (2R,3S,4S)-3-Hexyl-4-(2-hydroxytridecyl)-oxetan-2-one (13d)

The title compound was synthesized according to the reaction scheme shown below.

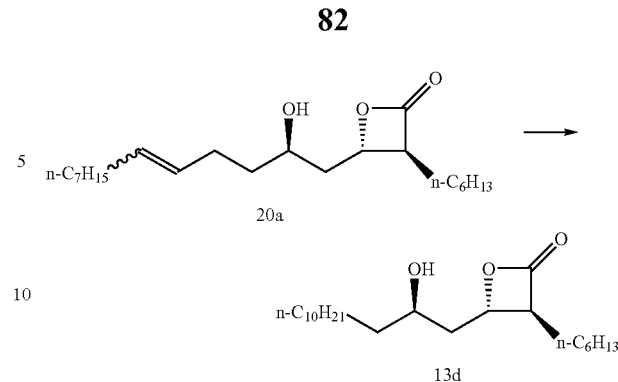

Prepared according to representative procedure described in Example 63, above. E/Z-mixture of β-lactone 20a (5.8 mg, 0.016 mmol) and 5 wt % palladium on carbon (5 mg) in 2 mL of THF was stirred at ambient temperature for 12 h under H$_2$ atmosphere. Filtration gave the desired β-lactone 13d (5.9 mg, 99%) as a white solid.

EXAMPLE 66

Esterase Inhibition by Compound of the Invention

Fluorogenic Assay for Detection of FASTE Inhibition

The synthetic fluorogenic substrate, 4-methylumbelliferyl heptanoate (4-MUH), was purchased from Sigma (St. Louis, Mo.). The reaction mixture consisted of 500 nM FAS TE in buffer (100 mM Tris-HCl, 50 mM NaCl at pH 7.4) which was pre-incubated with 2.5 µL test compounds dissolved in DMSO at final concentrations of 0.32-100M and/or 0.08-10 µM at 37° C. for 30 minutes. The reaction was initiated by addition of 5 µL of 1.25 mM 4-MUH in 1:1 DMSO:buffer A. The resulting fluorescence from liberated 4-methylumbelliferone was measured every five minutes at 350/450 nm for 40-60 minutes. 4-MUH incubated without enzyme served as a background control. Results are the average of triplicate time points.

Fluorogenic Assay for Detection of 20S Proteasome

The fluorogenic peptide substrate Suc-LLVY-AMC was purchased from Calbiochem (La Jolla, Calif.). The reaction mixture consisted of approximately 5 nM 20S proteasome in buffer (50 mM Tris-HCl, pH 7.5, 1 mM DTT, 1% v/v DMSO, 5 mM MgCl$_2$, and 0.02% SDS) and 1 µL test compounds dissolved in DMSO at final concentrations of 0.4-50 µM along with 100 µM Suc-LLVY-AMC. The resulting fluorescence from liberated AMC was measured every ten minutes at 380/460 nm for 2-3 hours. Suc-LLVY-Amc incubated without proteasome served as a background control. Results are the average of duplicate time points.

Cell Viability Assays for Determination of Test Compound Potencies

MB-MDA-435, MB-MDA-231, or human fibroblast cells were plated in 96-well plates in appropriate media and incubated overnight at 37° C. and 5% CO$_2$. Cells were treated with test compounds (0.1-100 µM) or vehicle in triplicate, with a final percentage of DMSO not exceeding 1% (v/v). At 48 h, the medium was aspirated and replaced with complete MEM, containing 333 µg/mL [3-(4,5-dimethylthiazol-2-yl)-5-(3-carboxymethoxyphenyl)-2-(4-sulfophenyl)-2H-tetrazolium (MTS) and 25 µM phenazine methosulfate (PMS), using the CellTiter 96 AQ$_{ueous}$ Non-Radioactive Cell Proliferation Assay (Promega). Plates were incubated for 2 h and absorbance was assayed at 490 nm. Background levels of formazan formation were measured in medium alone. IC$_{50}$ values were derived from dose-response curves.

The results of the inhibition tests are provided in Table 8.

TABLE 8

| Structure | avg Ki (uM) | stdev (+/−) | CLogP | avg 3 k 231 IC50 (uM) | st dev (+/−) | avg 3 k HFF IC50 (uM) | st dev (+/−) | avg 50 k HFF IC50 (uM) | st dev (+/−) | ratio |
|---|---|---|---|---|---|---|---|---|---|---|
| 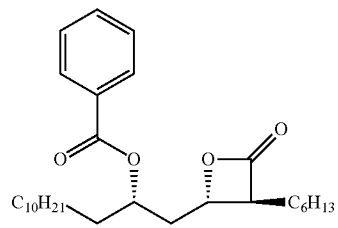 | 1.14 | 0.22 | 9.667 | >100 | n/a | >100 | n/a | >100 | n/a | 1.00 |
| 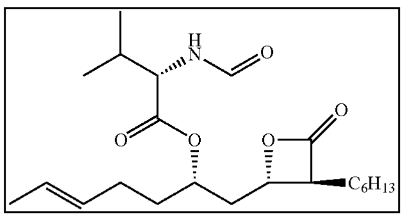 | 1.11 | 0.42 | 7.551 | 23.0 | 1.5 | 35.0 | 1.3 | 27.6 | 2.6 | 1.48 |
| 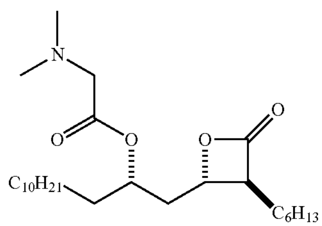 | 0.12 | 0.05 | 7.901 | 26.9 | 12.2 | 37.3 | 0.3 | 49.3 | 2.4 | 1.40 |
| 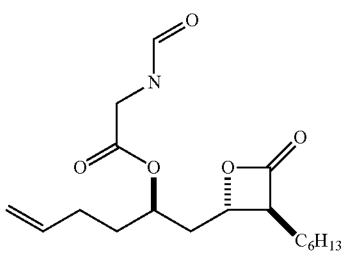 | 0.53 | 0.33 | 9.628 | >100 | n/a | >100 | n/a | >100 | n/a | 1.00 |

TABLE 8-continued

| Structure | avg Ki (uM) | stdev (+/−) | CLogP | avg 3 k 231 IC50 (uM) | st dev (+/−) | avg 3 k HFF IC50 (uM) | st dev (+/−) | avg 50 k HFF IC50 (uM) | st dev (+/−) | ratio |
|---|---|---|---|---|---|---|---|---|---|---|
| (His-containing β-lactone with C12H25 chain) | 0.17 | 0.05 | 7.227 | 37.1 | 11.8 | 15.8 | 3.4 | 28.0 | 1.6 | 0.36 |
| (Leu-containing β-lactone with C10H21 chain) | 0.14 | 0.09 | 8.609 | 20.1 | 7.6 | >100 | n/a | >100 | n/a | 5.00+ |
| (Gly-containing β-lactone with C10H21 chain) | 0.17 | 0.04 | 6.843 | 4.8 | 0.5 | 19.9 | 4.4 | 27.6 | 0.1 | 3.54 |

TABLE 8-continued

| Structure | avg Ki (uM) | stdev (+/−) | CLogP | avg 3 k 231 IC50 (uM) | st dev (+/−) | avg 3 k HFF IC50 (uM) | st dev (+/−) | avg 50 k HFF IC50 (uM) | st dev (+/−) | ratio |
|---|---|---|---|---|---|---|---|---|---|---|
| 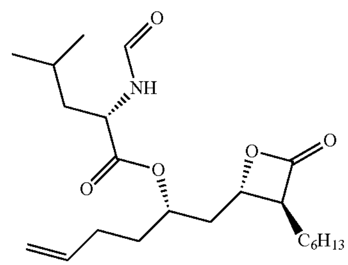 | 0.10 | 0.03 | 4.422 | 3.3 | 0.6 | 29.6 | 2.3 | 31.5 | 1.3 | 9.45 |
| 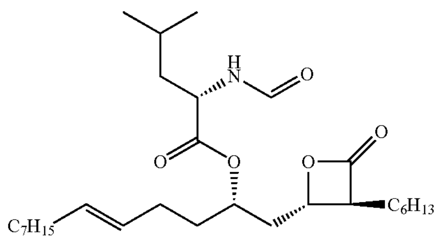 | 0.11 | 0.06 | 8.125 | 62.5 | 53.0 | 43.9 | 13.9 | 94.9 | 15.5 | 0.86 |
| 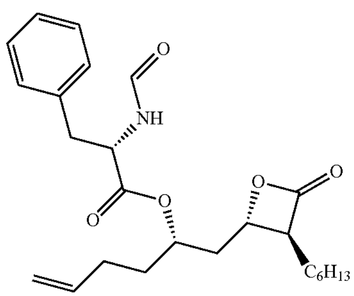 | 0.22 | 0.01 | 4.383 | 24.5 | 0.8 | 73.6 | 2.0 | 65.0 | 6.2 | 2.95 |
| 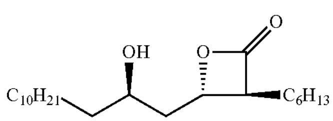 | 0.48 | 0.06 | 7.066 | 26.8 | 11.8 | 40.4 | 0.9 | 29.3 | 4.6 | 1.48 |

TABLE 8-continued

| Structure | avg Ki (uM) | stdev (+/-) | CLogP | avg 3 k 231 IC50 (uM) | st dev (+/-) | avg 3 k HFF IC50 (uM) | st dev (+/-) | avg 50 k HFF IC50 (uM) | st dev (+/-) | ratio |
|---|---|---|---|---|---|---|---|---|---|---|
| 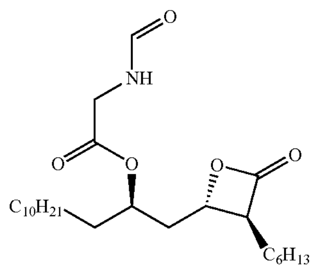 | 0.22 | 0.12 | 6.843 | 11.7 | 0.9 | 46.8 | 0.3 | 40.5 | 3.9 | 4.03 |
| 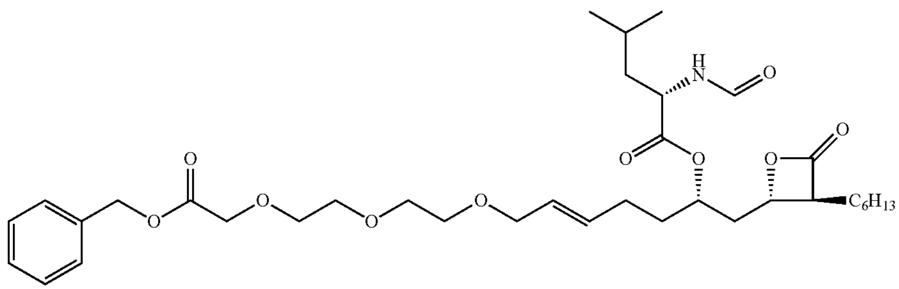 | 0.23 | 0.07 | 5.196 | 47.3 | 21.1 | 70.4 | 4.8 | >100 | n/a | 1.56 |
| 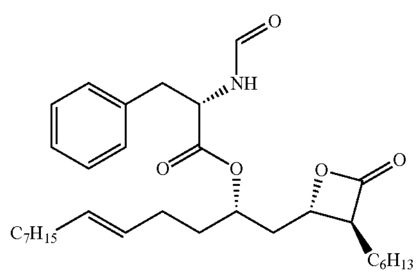 | 0.15 | 0.04 | 8.086 | >100 | n/a | 24.9 | 0.1 | 35.9 | 5.4 | 0.25 |

TABLE 8-continued
| Structure | avg Ki (uM) | stdev (+/−) | CLogP | avg 3 k 231 IC50 (uM) | st dev (+/−) | avg 3 k HFF IC50 (uM) | st dev (+/−) | avg 50 k HFF IC50 (uM) | st dev (+/−) | ratio |
|---|---|---|---|---|---|---|---|---|---|---|
| 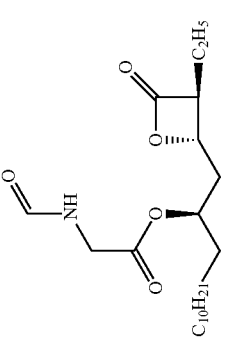 | 0.23 | 0.13 | 4.727 | 1.3 | 0.1 | 10.0 | 2.4 | 9.7 | 1.4 | 9.00 |
| 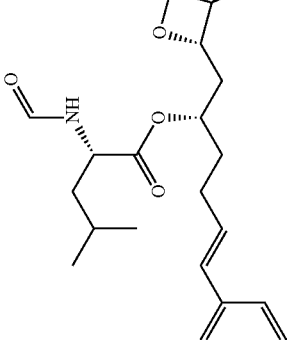 | 0.15 | 0.03 | 6.163 | 14.1 | 4.7 | 32.9 | 4.2 | 49.9 | 0.8 | 2.56 |
| 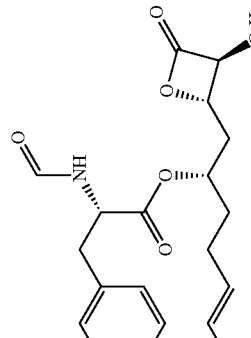 | 0.23 | n/a | 4.912 | 38.3 | 0.9 | 61.2 | 3.0 | 52.5 | 3.4 | 1.65 |
| 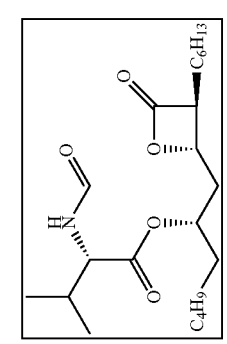 | 0.04 | 0.02 | 4.906 | 10.5 | 2.5 | >100 | n/a | >100 | n/a | 10.00+ |

TABLE 8-continued

| Structure | avg Ki (uM) | stdev (+/-) | CLogP | avg 3 k 231 IC50 (uM) | st dev (+/-) | avg 3 k HFF IC50 (uM) | st dev (+/-) | avg 50 k HFF IC50 (uM) | st dev (+/-) | ratio |
|---|---|---|---|---|---|---|---|---|---|---|
| | 0.10 | 0.04 | 4.422 | 56.9 | 19.0 | 101.2 | 12.4 | >100 | n/a | 1.93 |
| 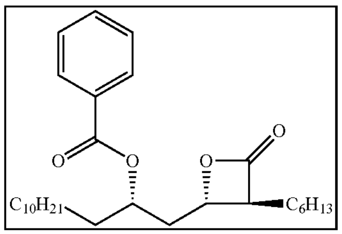 | 0.27 | 0.11 | 9.779 | >100 | n/a | >100 | n/a | >100 | n/a | 1.00 |
| | 0.10 | n/a | 4.422 | ND | ND | ND | ND | ND | ND | ND |
| 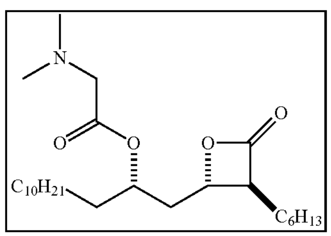 | 0.01 | 0.00 | 8.001 | 52.1 | 6.3 | 105.1 | 4.1 | 75.6 | 8.3 | 2.07 |

TABLE 8-continued
| Structure | avg Ki (uM) | stdev (+/−) | CLogP | avg 3 k 231 IC50 (uM) | st dev (+/−) | avg 3 k HFF IC50 (uM) | st dev (+/−) | avg 50 k HFF IC50 (uM) | st dev (+/−) | ratio |
|---|---|---|---|---|---|---|---|---|---|---|
| 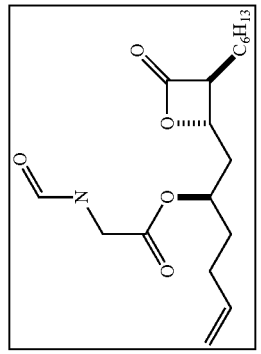 | 0.06 | 0.04 | 2.656 | 54.0 | 9.4 | >100 | n/a | >100 | n/a | 1.50+ |
| 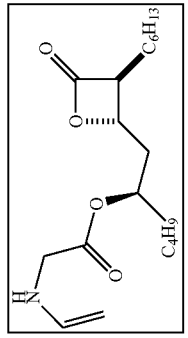 | 0.02 | 0.00 | 3.140 | 48.0 | 5.7 | 52.2 | 3.9 | 63.6 | 22.4 | 1.03 |
| 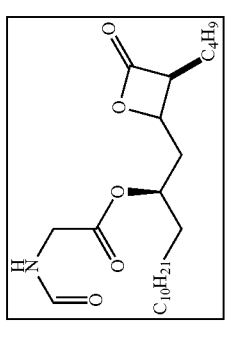 | 0.16 | 0.10 | 5.785 | 35.7 | 1.3 | 31.1 | 3.2 | 43.2 | 2.5 | 0.81 |
| 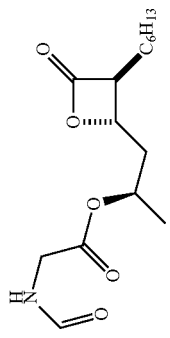 | 0.09 | 0.02 | 1.550 | >100 | n/a | >100 | n/a | >100 | n/a | 1.00 |

TABLE 8-continued
| Structure | avg Ki (uM) | stdev (+/−) | CLogP | avg 3 k 231 IC50 (uM) | st dev (+/−) | avg 3 k HFF IC50 (uM) | st dev (+/−) | avg 50 k HFF IC50 (uM) | st dev (+/−) | ratio |
|---|---|---|---|---|---|---|---|---|---|---|
| 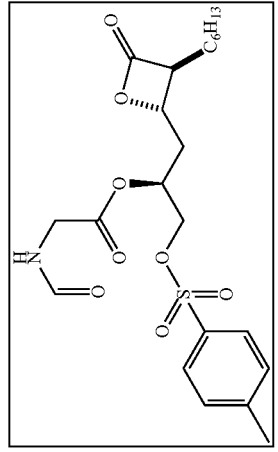 | 0.10 | 0.01 | 2.508 | >100 | n/a | >100 | n/a | >100 | n/a | 1.00 |
| 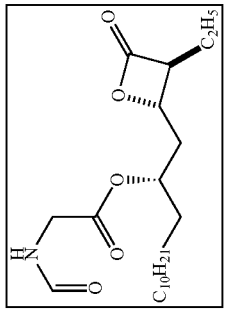 | 0.16 | 0.01 | 4.727 | 88.4 | 7.3 | >100 | n/a | >100 | n/a | 1.14 |
| 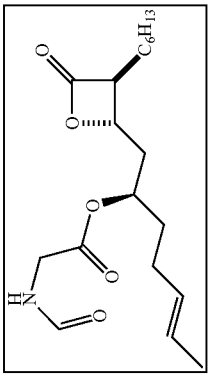 | 2.14 | 0.52 | 3.190 | 57.3 | 7.6 | 39.9 | 2.6 | 37.0 | 2.8 | 0.66 |
| 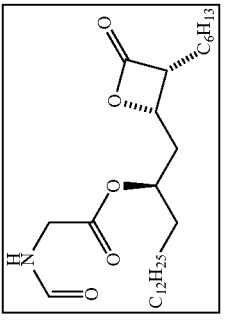 | 0.04 | 0.00 | 7.900 | >100 | n/a | >100 | n/a | >100 | n/a | 1.00 |

Although the invention has been described with reference to the above examples, it will be understood that modifications and variations are encompassed within the spirit and scope of the invention. Accordingly, the invention is limited only by the following claims.

What is claimed is:

1. A compound having formula IV, or a pharmaceutically acceptable salt thereof:

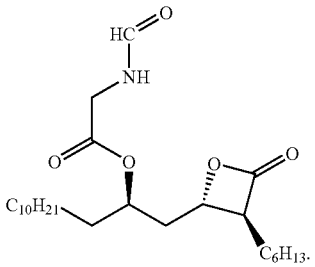

III

2. A pharmaceutical composition comprising the compound of claim 1, and a pharmaceutically acceptable carrier.

3. A kit comprising a packaging material and a pharmaceutical composition of claim 2 contained within the packaging material, wherein the packaging material comprises a label which indicates that the composition can be used for treating a disorder, disease, or pathology in a subject in need thereof.

* * * * *